(12) United States Patent
Iwama et al.

(10) Patent No.: US 7,977,512 B2
(45) Date of Patent: Jul. 12, 2011

(54) AMINE DERIVATIVE, AND PRODUCTION METHOD AND USE THEREOF

(75) Inventors: Hideki Iwama, Fukushima (JP); Junko Sudo, Fukushima (JP); Susumu Shimizu, Fukushima (JP); Masataka Katohno, Fukushima (JP); Masashi Yamamoto, Kanagawa (JP); Shigeru Suzuki, Fukushima (JP); Hiroshi Hoshino, Fukushima (JP); Nanako Kuruhara, Fukushima (JP)

(73) Assignee: Kureha Corporation, Tokyo (JP)

( * ) Notice: Subject to any disclaimer, the term of this patent is extended or adjusted under 35 U.S.C. 154(b) by 576 days.

(21) Appl. No.: 11/990,786

(22) PCT Filed: Aug. 22, 2006

(86) PCT No.: PCT/JP2006/316371
§ 371 (c)(1),
(2), (4) Date: Feb. 21, 2008

(87) PCT Pub. No.: WO2007/023788
PCT Pub. Date: Mar. 1, 2007

(65) Prior Publication Data
US 2008/0293951 A1    Nov. 27, 2008

(30) Foreign Application Priority Data
Aug. 22, 2005    (JP) .................................. 2005-239518

(51) Int. Cl.
*C07C 211/27* (2006.01)
(52) U.S. Cl. ...................................................... 564/367
(58) Field of Classification Search .................... 564/367
See application file for complete search history.

(56) References Cited

U.S. PATENT DOCUMENTS

| | | | |
|---|---|---|---|
| 2004/0092556 A1 | 5/2004 | Yamazaki et al. | |
| 2004/0157818 A1 | 8/2004 | Yanaka et al. | |
| 2004/0254221 A1 | 12/2004 | Yamazaki et al. | |
| 2005/0165063 A1 | 7/2005 | Yamazaki et al. | |
| 2007/0208007 A1* | 9/2007 | Saitou et al. | 514/218 |

FOREIGN PATENT DOCUMENTS

| | | |
|---|---|---|
| EP | 1 550 657 A1 A1 | 9/2003 |
| WO | WO 01/79168 A1 | 4/2001 |
| WO | WO 02/94261 A1 | 5/2002 |
| WO | WO 03/029218 A1 | 9/2002 |
| WO | WO 2004/024697 A1 | 9/2003 |
| WO | WO 2004/024697 * | 3/2004 |
| WO | WO 2005/085209 A1 | 3/2005 |
| WO | WO 2005/085209 * | 9/2005 |

OTHER PUBLICATIONS

International Search Report for PCT/JP2006/316371 dated Nov. 28, 2006.

* cited by examiner

*Primary Examiner* — Joseph R Kosack
(74) *Attorney, Agent, or Firm* — Reed Smith LLP

(57) ABSTRACT

Disclosed is a benzonitrile derivative which is useful as a production intermediate for benzylamine derivative represented by the general formula (5) below and s secondary amine derivative represented by the general formula (9) below. Also disclosed are a method for producing such a benzonitrile derivative and a use thereof as a bactericide. Specifically disclosed are a novel benzonitrile derivative represented by the general formula (1) below, a salt thereof, a production method thereof, and a use thereof as a pharmaceutical intermediate or a bactericide. [Chemical formula 1] (5) (In the formula, n represents an integer of 0-3, and $R^1$ represents a hydrogen, a linear or branched alkyl group having 1-6 carbon atoms or the like.) [Chemical formula 2] (9) (In the formula, n and $R^1$ are a defined above, and $R^4$ represents a hydrogen, a linear or branched alkl group having 1-6 carbon atoms or the like.) [Chemical formula 3] (1) (In the formula, n represents an integer of 0-3, and $R^1$ represents a hydrogen, a linear or branched alkyl group having 1-6 carbon atoms or the like.)

7 Claims, No Drawings

AMINE DERIVATIVE, AND PRODUCTION METHOD AND USE THEREOF

TECHNICAL FIELD

The present invention relates to a benzonitrile derivative represented by a general formula (1) and a salt thereof. The compound represented by the general formula (1) is useful as an intermediate for efficiently producing a benzylamine derivative represented by a general formula (5) or a secondary amine derivative represented by a general formula (9), and is also useful as an active component of bactericides.

The compounds represented by the general formulas (5) and (9) are important synthetic intermediates in the pharmaceutical industry, as described in Patent Documents 1 and 2.

The present invention also relates to a method of producing a benzonitrile derivative represented by the general formula (1), a method of producing a benzylamine derivative represented by the general formula (5), and a method of producing a secondary amine derivative represented by the general formula (9).

The present invention further relates to an imine derivative represented by general formula (8) which is used as an intermediate in producing a secondary amine derivative represented by the general formula (9) from a benzylamine derivative represented by the general formula (5).

BACKGROUND ART

The following methods have been known as methods for producing a benzylamine derivative represented by the general formula (5) and a secondary amine derivative represented by the general formula (9) used as pharmaceutical intermediates.

For example, Patent Documents 1 and 2 disclose methods in which a benzylamine derivative represented by the general formula (5) is produced by using a compound prepared by selectively protecting only one primary amino group of readily-available 1,4-diaminobutane with a t-butoxycarbonyl (Boc) group as a starting material, and a secondary amine derivative represented by the general formula (9) is produced from the benzylamine derivative represented by the general formula (5).

An amine derivative disclosed in Patent Documents 1 and 2, which is effective against diseases such as HIV virus infection, rheumatism, or cancer metastasis, can be easily derived from the benzylamine derivative represented by the general formula (5) using the methods disclosed in Patent Documents 1 and 2.

[Patent Document 1] WO 2004/024697
[Patent Document 2] WO 2005/085209

However, since the methods disclosed in Patent Documents 1 and 2 require multiple introduction/deblocking of an expensive protecting group t-butoxycarbonyl (Boc) in order to protect the primary amino group, an increase in the number of steps, an increase in cost, a decrease in yield, and the like are caused. Moreover, these methods are not satisfactory for industrial production of the benzylamine derivative represented by the general formula (5) and the secondary amine derivative represented by the general formula (9) due to a step using highly volatile and poisonous dichloromethane as a solvent. Since these methods require plural purification steps using silica gel chromatography, these methods undergo a complicated operation, an increase in the number of steps, an increase in cost, a decrease in yield, and the like, thus these methods were not practical.

Various bactericides have been put to practical use based on the research and development of agricultural/horticultural disease protective agents over many years. These bactericides have contributed to labor saving and an increase in productivity. On the other hand, development of a compound useful as a bactericide which has reduced toxicity to humans and animals and increased handling safety has been desired.

DISCLOSURE OF THE INVENTION

Problems to be Solved by the Invention

An object of the present invention is to provide an intermediate used to efficiently produce a benzylamine derivative represented by the general formula (5) and a secondary amine derivative represented by the general formula (9). Another object of the present invention is to provide a method of safely producing a benzylamine derivative represented by the general formula (5) or a secondary amine derivative represented by the general formula (9) which is useful as a pharmaceutical intermediate at low cost, and high yield with a reduced number of steps.

Means for Solving the Problems

The inventors of the present invention conducted extensive studies on a method of producing a benzylamine derivative represented by the general formula (5) in order to achieve the above objects. As a result, the inventors found that the benzylamine derivative can be produced at low cost and high yield with a reduced number of steps through a benzonitrile derivative represented by the general formula (1) as an intermediate. This finding led to the completion of the present invention.

The inventors also conducted extensive studies on the method of producing a secondary amine derivative represented by the general formula (9) in order to achieve the above objects. As a result, the inventors found that the secondary amine derivative can be produced at low cost and high yield with a reduced number of steps without using a benzylamine derivative represented by the general formula (5) as an intermediate. This finding led to the completion of the present invention.

The inventors conducted further studies in order to achieve the above objects. As a result, the inventors found that a novel benzonitrile derivative represented by the general formula (1) or a salt thereof has reduced toxicity to humans and animals, increased handling safety, and bactericidal activity.

Specifically, the present invention has the following constitutions.

A first aspect of the present invention relates to a benzonitrile derivative represented by the following general formula (1) and a salt thereof,

[Formula 25]

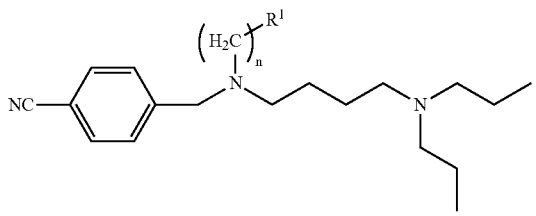

(wherein n represents an integer from 0 to 3; and R¹ represents hydrogen; a linear or branched alkyl group having 1 to 6 carbon atoms; a halogen atom; a nitro group; a cyano group; a carboxyl group; an amide group; a sulfonyl group; a hydroxyl group; a linear or branched alkoxy group having 1 to 6 carbon atoms; a linear or branched alkylcarbonyl group having 1 to 6 carbon atoms; a linear or branched alkoxycarbonyl group having 1 to 6 carbon atoms; a phenyl group; a phenyl group of which the aromatic ring is substituted by one or more of a halogen atom, a nitro group, a cyano group, a carboxyl group, an amide group, a sulfonyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a benzoyl group; a benzoyl group of which the aromatic ring is substituted by one or more of a halogen atom, a nitro group, a cyano group, a carboxyl group, an amide group, a sulfonyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a benzyloxycarbonyl group, a pyridyl group, a furyl group, an imidazolyl group, a triazolyl group, a tetrazolyl group, a naphthyl group, or a tetrahydrofuryl group, provided that, when n=0, R¹ represents hydrogen or a linear or branched alkyl group having 1 to 6 carbon atoms.)

A second aspect of the present invention relates to a benzonitrile derivative represented by the following general formula (2) and a salt thereof,

[Formula 26]

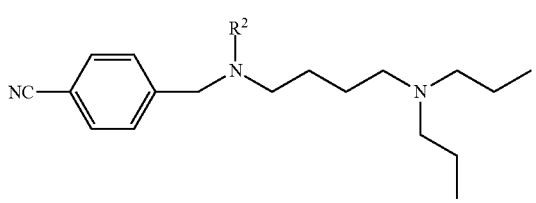

(wherein R² represents hydrogen or a methyl group.)

The present invention also relates to a method of producing a benzonitrile derivative using 4-dipropylaminobutyronitrile (3) as a raw material, the method comprising reducing the 4-dipropylaminobutyronitrile (3) to produce 4-dipropylaminobutylamine (4), and

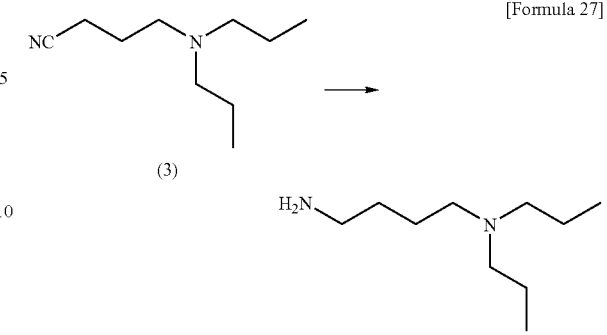

subjecting the primary amino group of the 4-dipropylaminobutylamine (4) to an alkylation reaction and a reductive alkylation reaction to produce a benzonitrile derivative represented by the general formula (1).

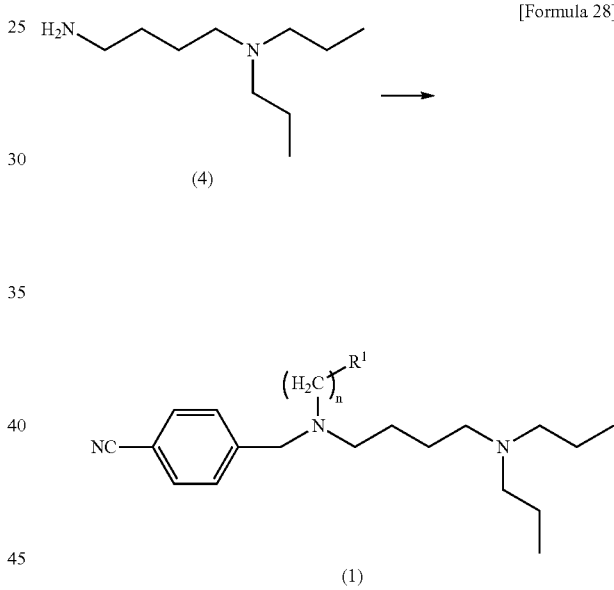

The alkylation reaction and the reductive alkylation reaction of the 4-dipropylaminobutylamine (4) to produce the benzonitrile derivative represented by the general formula (1) may be carried out in an arbitrary order. Specifically, the benzonitrile derivative represented by the general formula (1) may be synthesized by subjecting the terminal primary amino group in the formula (4) to an alkylation reaction to obtain a secondary amine and subjecting the resulting product to a reductive alkylation reaction, or may be synthesized by subjecting the terminal primary amino group in the formula (4) to a reductive alkylation reaction and subjecting the resulting product to an alkylation reaction.

The latter production method includes a method of producing the benzonitrile derivative comprising the following steps:

(1) step of producing 4-dipropylaminobutylamine (4) by subjecting 4-dipropylaminobutyronitrile (3) as a raw material to a reduction reaction,

[Formula 29]

(3)

(4)

(2) step of producing 4-[(4-dipropylaminobutyl)amino]methylbenzonitrile (2a) by subjecting the obtained 4-dipropylaminobutylamine (4) to a reductive alkylation reaction using 4-cyanobenzaldehyde, and

[Formula 30]

(4)

+

(2a)

(3) step of subjecting the 4-[(4-dipropylaminobutyl)amino]methylbenzonitrile (2a) as a raw material to an alkylation reaction,

[Formula 31]

(2a)

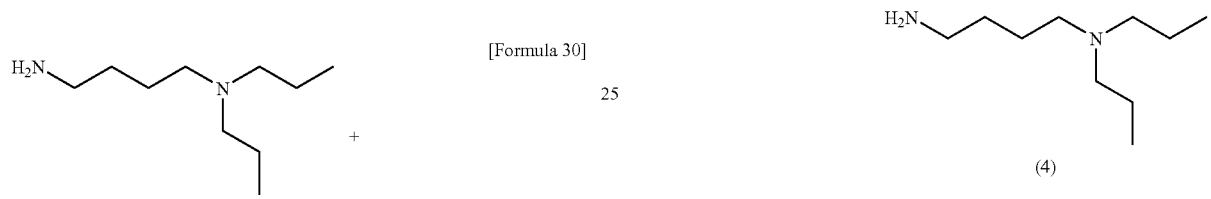

(1)

(wherein n and R¹ are the same as defined above.)

The present invention also relates to the following production methods.

A method including subjecting 4-dipropylaminobutyronitrile (3) as a raw material to a reduction reaction to produce 4-dipropylaminobutylamine (4), and subjecting the obtained 4-dipropylaminobutylamine (4) to a reductive alkylation reaction using 4-cyanobenzaldehyde to produce 4-[(4-dipropylaminobutyl)amino]methylbenzonitrile (2a).

[Formula 32]

(3)

(4)

[Formula 33]

(4)

+

(2a)

A method including subjecting 4-[(4-dipropylaminobutyl)amino]methylbenzonitrile (2a) as a raw material to an alkylation reaction to produce a benzonitrile derivative represented by the following general formula (1),

[Formula 34]

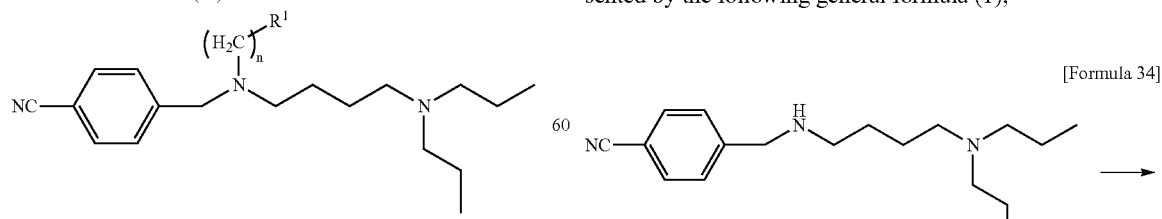

(2a)

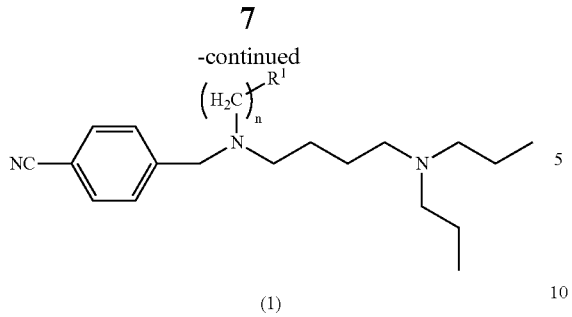

(1)

(wherein n and $R^1$ are the same as defined above.)

A method including subjecting 4-[(4-dipropylaminobutyl)amino]methylbenzonitrile (2a) to methylation to produce 4-[(4-dipropylaminobutyl)methylamino]methylbenzonitrile (2b).

[Formula 35]

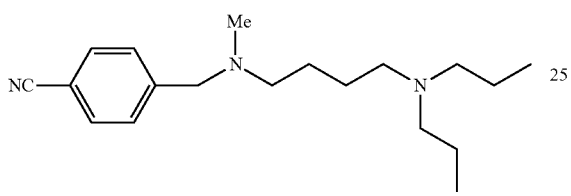

(2b)

In the above method, a method in which the alkylation reaction may be carried out using an alkylating agent such as an alkyl halide.

In the above method, a method in which the alkylation reaction is a reductive alkylation reaction using an aldehyde derivative.

As the above methylation method, a method in which 4-[(4-dipropylaminobutyl)methylamino]methylbenzonitrile (2b) is produced using a formaldehyde aqueous solution and a reducing agent.

In the above method, a method in which formic acid may be used as the reducing agent.

The present invention also relates to a pharmaceutical intermediate comprising a benzonitrile derivative represented by the general formula (1) or a salt thereof, and a bactericide comprising a benzonitrile derivative represented by the general formula (1) or a salt thereof as an active component.

The present invention also relates to a method comprising subjecting a benzonitrile derivative represented by the following general formula (1) as a raw material to a reduction reaction to produce a benzylamine derivative represented by the following general formula (5),

[Formula 36]

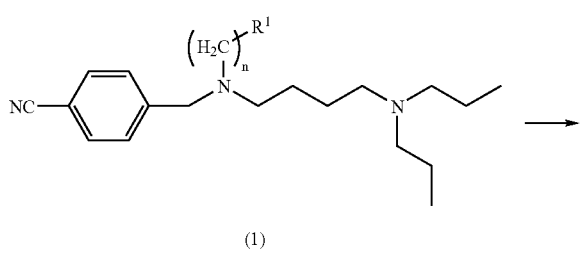

(1)

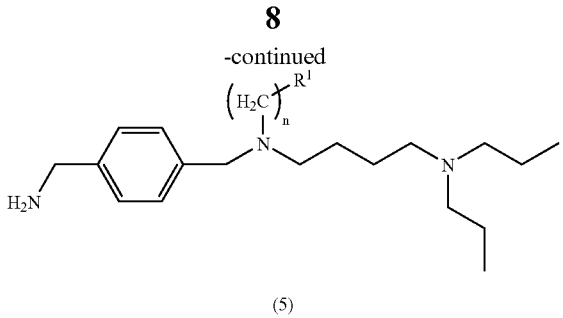

(5)

(wherein n and $R^1$ are the same as defined above.)

The present invention also includes the above method wherein the reduction reaction is carried out by a catalytic hydrogenation reduction with Raney nickel.

The present invention also relates to a method of producing a benzylamine derivative represented by the general formula (5) comprising the following steps. In this production method, a reaction equation A is a protection reaction of a terminal amino group, and a reaction equation C is a deprotection reaction.

(1) step of causing the primary amino group of 4-[(4-dipropylaminobutyl)amino]methylbenzylamine (5a) to react with an aldehyde (6) to produce an imine derivative (7) according to the following reaction equation A,

[Reaction equation A]

[Formula 37]

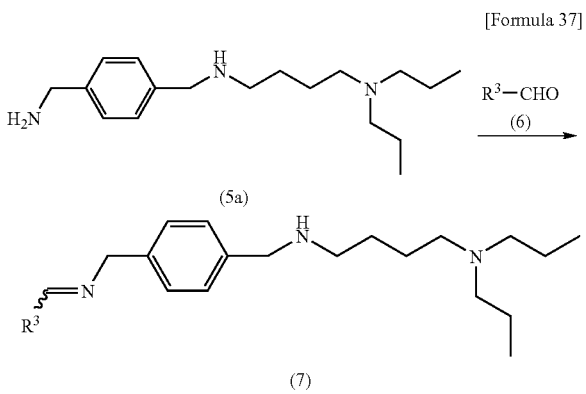

(wherein, $R^3$ represents hydrogen; a linear or branched alkyl group having 1 to 6 carbon atoms; a linear or branched alkoxy group having 1 to 6 carbon atoms; a linear or branched alkylcarbonyl group having 1 to 6 carbon atoms; a linear or branched alkoxycarbonyl group having 1 to 6 carbon atoms; a carboxyl group; a phenyl group; a phenyl group of which the aromatic ring is substituted by one or more of a halogen atom, a nitro group, a cyano group, a carboxyl group, an amide group, a sulfonyl group, a trifluoromethyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a pyridyl group; a pyridyl group of which the ring is substituted by one or more of a halogen atom, a nitro group, a cyano group, a carboxyl group, an amide group, a sulfonyl group, a trifluoromethyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a furyl group; a furyl group of which the ring is substituted by one or more of a halogen atom, a nitro group, a cyano group, a carboxyl group, an amide group, a sulfonyl group, a trifluoromethyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; an imidazolyl group; an imidazolyl group of which the ring is substituted by one or more of a halogen atom, a nitro group, a cyano group, a carboxyl group, an amide group, a sulfonyl group, a trifluoromethyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a naphthyl group; a naphthyl group of which the ring is substituted by one or more of a halogen atom, a nitro group, a cyano group, a carboxyl group, an amide group, a sulfonyl group, a trifluoromethyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a tetrahydrofuryl group; or a tetrahydrofuryl group of which the ring is substituted by one or more of a halogen atom, a nitro group, a cyano group, a carboxyl group, an amide group, a sulfonyl group, a trifluoromethyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group)

(2) step of subjecting the secondary amino group to an alkylation reaction according to the following reaction equation B,

[Reaction equation B]

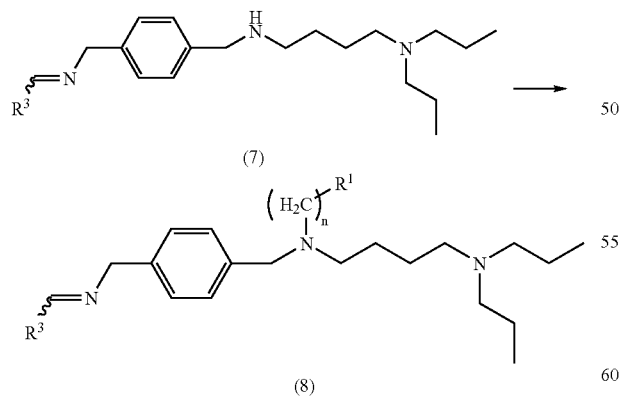

(wherein n, $R^1$, and $R^3$ are the same as defined above, provided that a case where —$(CH_2)n$-$R^1$ is hydrogen is excluded) and (3) step of decomposing the imino group using an acid according to the following reaction equation C,

[Reaction equation C]

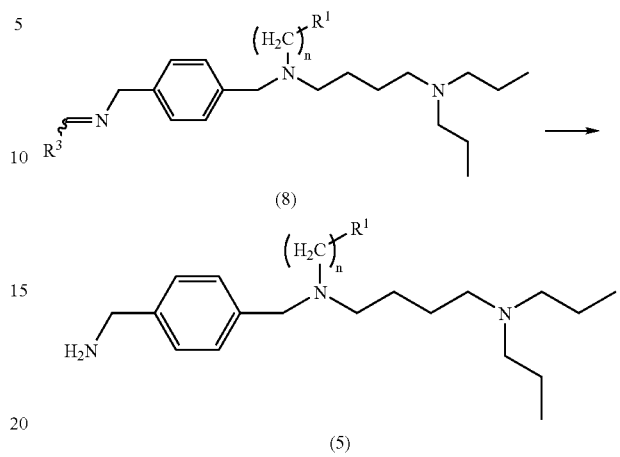

(wherein n, $R^1$ and $R^3$ are the same as defined above, provided that a case where —$(CH_2)n$-$R^1$ is hydrogen is excluded.)

The present invention further relates to a method comprising subjecting a benzylamine derivative represented by the following general formula (5) to react with an aldehyde (6) to produce an imine derivative (8), and reducing the imino group to produce a secondary amine derivative represented by the following general formula (9). In this production method, the compound of the formula (9) may be obtained using the compound of the formula (5a) as a raw material by combining with the method described in order to produce the compound (5).

[Formula 40]

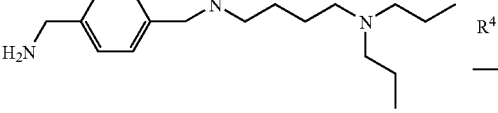

(Wherein n and $R^1$ are the same as defined above, and $R^4$ has the same definition as $R^3$ described above.)

The present invention also relates to a method of producing a secondary amine derivative represented by the general formula (9) comprising the following steps. This method provides another method for producing the compound of the formula (9) using the compound of the formula (5a) as a raw material. According to this method, the protection and deprotection reactions shown by the above reaction equations A and C respectively are unnecessary.

(1) Step of causing the primary amino group of 4-[(4-dipropylaminobutyl)amino]methylbenzylamine (5a) to react with an aldehyde (6) to produce an imine derivative (7) according to the following reaction equation A,

[Reaction equation A]

[Formula 41]

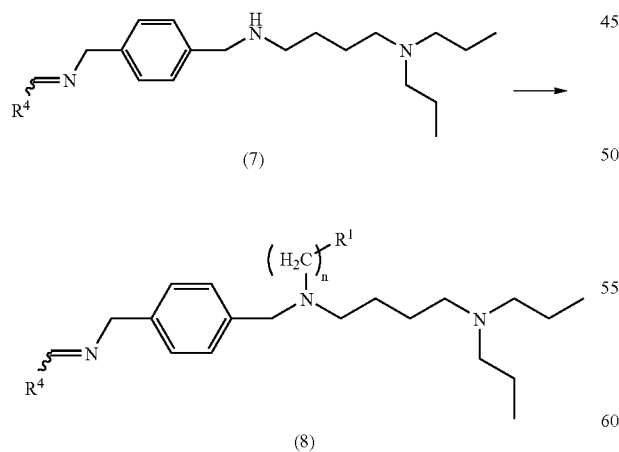

(wherein $R^4$ has the same definition as $R^3$ described above)

(2) Step of subjecting the secondary amino group to an alkylation reaction according to the following reaction equation B,

[Reaction equation B]

[Formula 42]

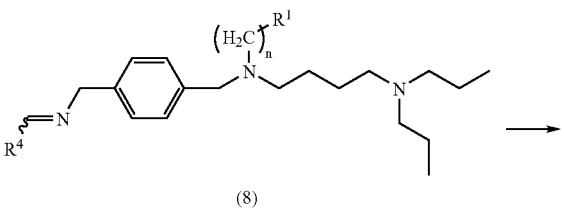

(wherein n and $R^1$ are the same as defined above, and $R^4$ has the same definition as $R^3$ described above)

(3) Step of reducing the imino group according to the following reaction equation D,

[Reaction equation D]

[Formula 43]

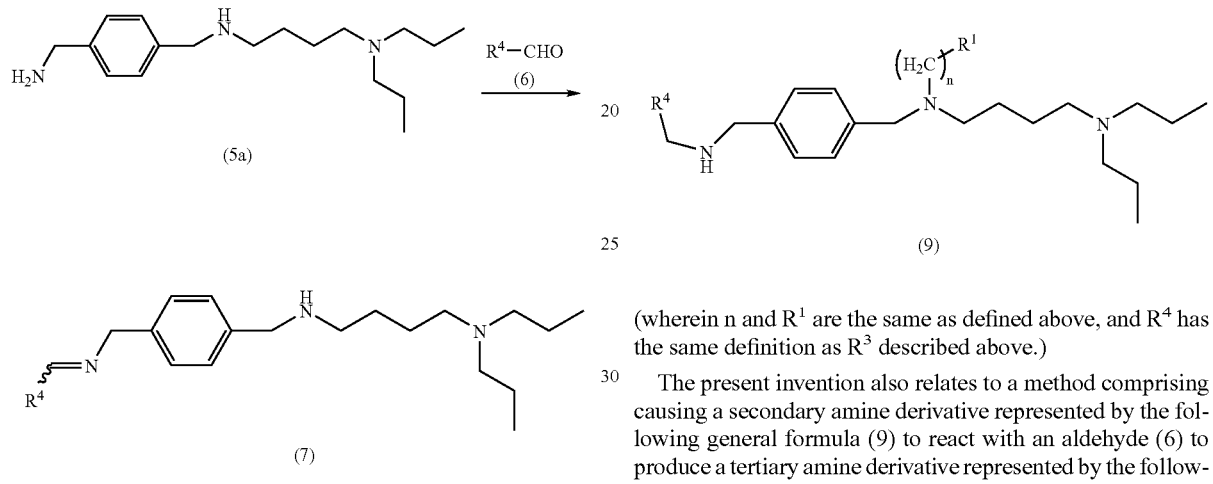

(wherein n and $R^1$ are the same as defined above, and $R^4$ has the same definition as $R^3$ described above.)

The present invention also relates to a method comprising causing a secondary amine derivative represented by the following general formula (9) to react with an aldehyde (6) to produce a tertiary amine derivative represented by the following general formula (10),

[Formula 44]

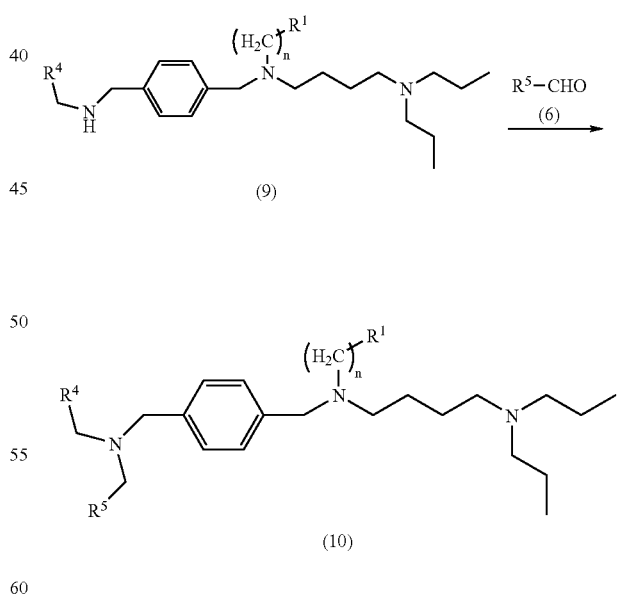

(wherein n and $R^1$ are the same as defined above, and $R^4$ and $R^5$ have the same definition as $R^3$ described above.)

$R^4$ and $R^5$ may be the same or different groups.

The present invention also relates to an imine derivative represented by the following general formula (8) obtained by the above reaction,

[Formula 45]

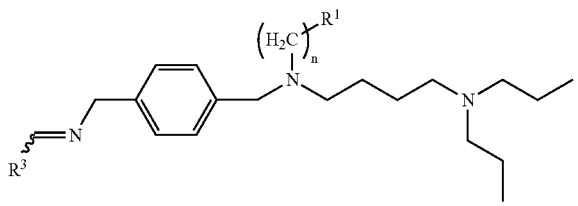

(8)

(wherein n, $R^1$ and $R^3$ are the same as defined above.)

Furthermore, the present invention also relates to a method of purifying a benzonitrile derivative represented by the following general formula (1), a benzylamine derivative represented by the general formula (5), or a secondary amine derivative represented by the general formula (9).

A method of purifying a benzonitrile derivative represented by the following general formula (1) comprising causing a crude compound of the benzonitrile derivative represented by the general formula (1) to form a salt with one or more inorganic or organic acids, and recrystallizing the resulting salt,

[Formula 46]

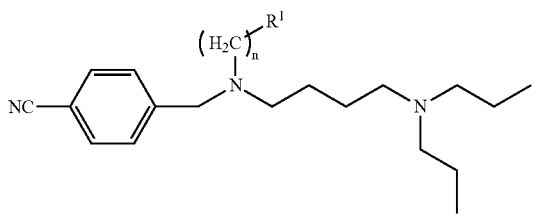

(1)

(wherein n and $R^1$ are the same as defined above.)

A method of purifying a benzylamine derivative represented by the following general formula (5) comprising causing a crude compound of the benzylamine derivative represented by the general formula (5) to form a salt with one or more inorganic or organic acids, and recrystallizing the resulting salt,

[Formula 47]

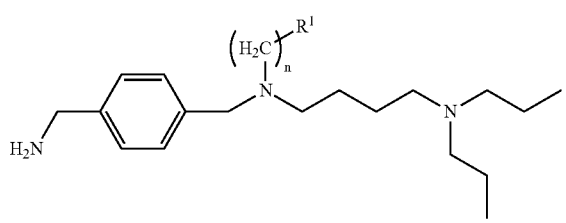

(5)

(wherein n and $R^1$ are the same as defined above.)

A method of purifying a secondary amine derivative represented by the following general formula (9) comprising causing a crude compound of the secondary amine derivative represented by the general formula (9) to form a salt with one or more inorganic or organic acids, and recrystallizing the resulting salt,

[Formula 48]

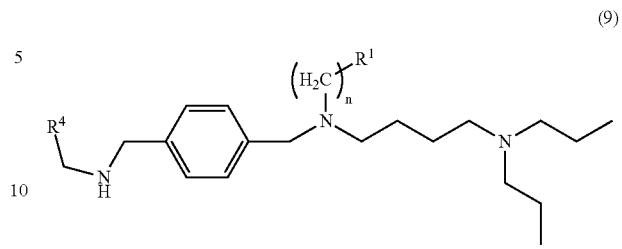

(9)

(wherein n and $R^1$ are the same as defined above, and $R^4$ has the same definition as $R^3$ described above.)

Effects of the Invention

The benzylamine derivative represented by the general formula (5) and the secondary amine derivative represented by the general formula (9) can be safely produced at a significantly increased yield and low cost with a reduced number of steps as compared with prior arts by using the novel benzonitrile derivative represented by the general formula (1) and a salt thereof according to the present invention. Therefore, the present invention has significant industrial value. A bactericide prepared using the novel benzonitrile derivative represented by the general formula (1) or a salt thereof exhibits reduced toxicity to humans and animals, increased handling safety, and high bactericidal activity.

BEST MODE FOR CARRYING OUT THE INVENTION

The present invention is described in detail below.

[Benzonitrile Derivative (1)]

The benzonitrile derivative represented by the following general formula (1) may be caused to form salts with various acids.

[Formula 49]

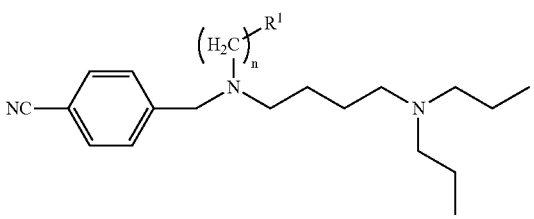

(1)

Examples of the acids used to form salts with the benzonitrile derivative include inorganic acids such as hydrochloric acid, hydrobromic acid, hydroiodic acid, sulfuric acid, nitric acid, phosphoric acid and the like, and organic acids such as formic acid, acetic acid, trifluoroacetic acid, carbonic acid, lactic acid, adipic acid, maleic acid, fumaric acid, gluconic acid, hippuric acid, malic acid, citric acid, tartaric acid, oxalic acid, malonic acid, succinic acid, propionic acid, butyric acid, glucuronic acid, camphorsulfonic acid, benzoic acid, methanesulfonic acid, benzenesulfonic acid, p-toluenesulfonic acid, terephthalic acid, oleic acid, stearic acid and the like. Of these, hydrochloric acid is particularly preferable.

Examples of agriculturally/horticulturally acceptable salts of the benzonitrile derivative (1) include a hydrochloride, an acetate, a fumarate, and the like, but not particularly limited thereto. Of these, a hydrochloride is particularly preferable.

[Benzonitrile Derivative (2)]

Among the benzonitrile derivatives represented by the general formula (1), the compounds represented by the following general formula (2) in which the substituent for N to which the methylbenzonitrile bonds is hydrogen or a methyl group are particularly useful,

[Formula 50]

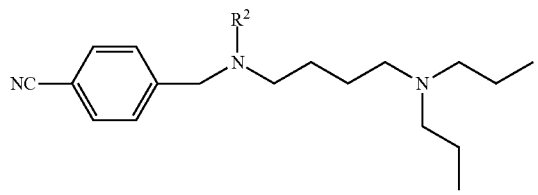

(2)

(wherein R² represents hydrogen or a methyl group.)

A compound in which R² in the general formula (2) is hydrogen is referred to as (2a), and a compound in which R² in the general formula (2) is a methyl group is referred to as (2b). These compounds may be caused to form salts with various acids.

[Formula 51]

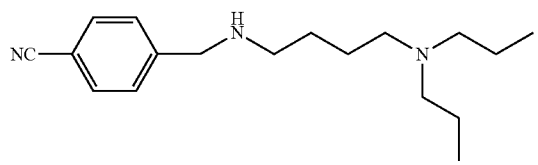

(2a)

[Formula 52]

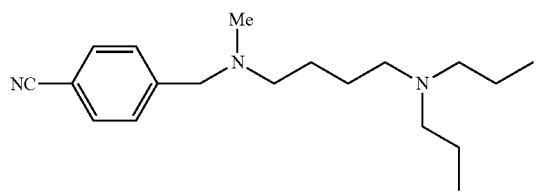

(2b)

Examples of the acids used to form salts with these compounds include inorganic acids such as hydrochloric acid, hydrobromic acid, hydroiodic acid, sulfuric acid, nitric acid, phosphoric acid and the like, formic acid, acetic acid, trifluoroacetic acid, carbonic acid, lactic acid, adipic acid, maleic acid, fumaric acid, gluconic acid, hippuric acid, malic acid, citric acid, tartaric acid, oxalic acid, malonic acid, succinic acid, propionic acid, butyric acid, glucuronic acid, camphorsulfonic acid, benzoic acid, methanesulfonic acid, benzenesulfonic acid, p-toluenesulfonic acid, terephthalic acid, oleic acid, stearic acid, and the like. Of these, hydrochloric acid is particularly preferable.

Examples of the agriculturally/horticulturally acceptable salts of the benzonitrile derivative (2) include a hydrochloride, an acetate, a fumarate, and the like, but not particularly limited thereto. Of these, a hydrochloride is particularly preferable.

[Production of 4-dipropylaminobutylamine (4)]

In this step, a easily-obtainable compound represented by the following formula (3) is reduced to produce 4-dipropylaminobutylamine (4). As the reduction method, a method using various hydride compounds or catalytic hydrogenation reduction using a metal catalyst or a noble metal catalyst may be applied. Examples of the hydride compounds include lithium aluminum hydride, sodium aluminum hydride, lithium triethylborohydride, sodium bis(2-methoxyethoxy) aluminum hydride, and the like, but not particularly limited thereto. Examples of the catalyst used for catalytic hydrogenation reduction include Raney nickel, Raney cobalt, and the like, but not particularly limited thereto. Further examples include palladium, platinum, rhodium, ruthenium, and the like. These metals may be used by supporting on a carrier such as silica gel, alumina, diatomite, activated carbon or the like or not supporting. When applying a catalytic hydrogenation reduction, the catalyst may be repeatedly used several to several tens of times. In this reaction, catalytic hydrogenation reduction using Raney nickel is particularly preferable.

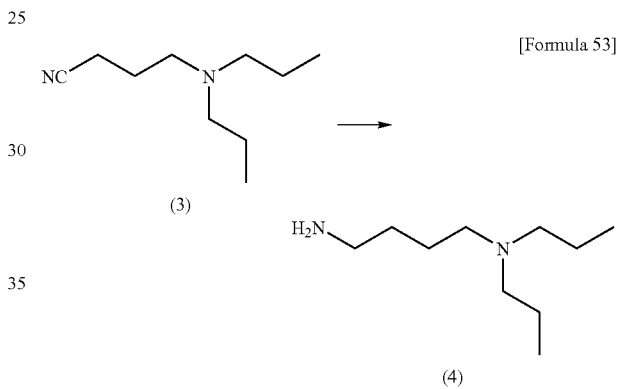

[Formula 53]

Examples of the solvent suitably used in the catalytic hydrogenation reduction using Raney nickel include water, methanol, ethanol, isopropanol, t-butanol, toluene, and the like. These solvents may be used alone or in combination with these solvents in an arbitrary ratio. A particularly preferable solvent is methanol, ethanol, a mixed solvent of methanol and water, or a mixed solvent of ethanol and water.

Examples of the base suitably used in the catalytic hydrogenation reduction using Raney nickel include sodium hydroxide, potassium hydroxide, lithium hydroxide, sodium methoxide, potassium methoxide, sodium ethoxide, potassium ethoxide, sodium t-butoxide, potassium t-butoxide, ammonia, and the like. A particularly preferable base is sodium hydroxide, sodium methoxide, or sodium ethoxide.

The amount of catalyst used for catalytic hydrogenation reduction using Raney nickel may be arbitrarily selected in the range of 5 to 30 wt %, preferably 10 to 20 wt %.

The reaction temperature is 0 to 100° C., and preferably 10 to 50° C. The reaction time is 10 hours to 10 days, and preferably one day to five days.

Production Step of 4-[(4-dipropylaminobutyl)amino]methylbenzonitrile (2a)

In this step, 4-[(4-dipropylaminobutyl)amino]methylbenzonitrile (2a) is produced by reacting a compound represented by the following formula (4) with 4-cyanobenzaldehyde in an appropriate organic solvent to obtain an imine derivative, and adding an appropriate reducing agent thereto.

In this reaction, sodium borohydride is particularly preferable as the reducing agent, but not particularly limited thereto. 4-[(4-dipropylaminobutyl)amino]methylbenzonitrile (2a) may also be obtained by catalytic reduction in a hydrogen atmosphere. Examples of the catalyst used for catalytic hydrogenation reduction include Raney nickel, Raney cobalt, and the like, but not particularly limited thereto. Further the examples include palladium, platinum, rhodium, ruthenium, and the like. These metals may be used by supporting on a carrier such as silica gel, alumina, diatomite, activated carbon or the like or not supporting. When applying a catalytic hydrogenation reduction, the catalyst may be repeatedly used several to several tens of times.

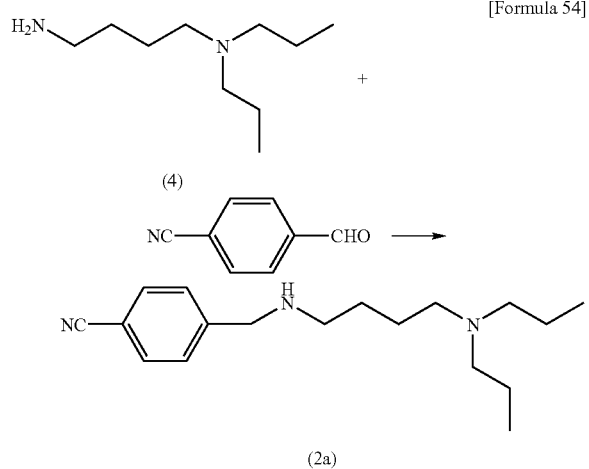

[Formula 54]

As a suitable solvent, methanol, ethanol, isopropanol, t-butanol, tetrahydrofuran, ethylene glycol dimethyl ether, diethylene glycol dimethyl ether, dimethylsulfoxide, N,N-dimethylformamide, N-methyl-2-pyrrolidinone, toluene, benzene, chloroform, and the like can be given. These solvents may be used alone or in combination with these solvents in an arbitrary ratio. Of these, methanol and ethanol are particularly preferable.

In this reaction, it is preferable to add a dehydrating agent when forming the imine derivative. Examples of the dehydrating agent include trimethyl orthoformate, triethyl orthoformate, anhydrous sodium sulfate, anhydrous magnesium sulfate, molecular sieve, and the like. A particularly preferable dehydrating agent is trimethyl orthoformate, triethyl orthoformate, or anhydrous sodium sulfate.

As the reducing agent, formic acid, sodium borohydride, sodium triacetoxyborohydride, sodium cyanoborohydride, or the like may be arbitrarily used in an amount of 1 to 5 equivalents, preferably 1 to 3 equivalents.

The amount of catalyst used for catalytic hydrogenation reduction may be arbitrarily selected in the range of 1 to 30 wt %, preferably 5 to 20 wt %. The reaction temperature is −30 to 100° C., and preferably −15 to 50° C. The reaction time is one hour to two days, and preferably three hours to one day.

The resulting unpurified 4-[(4-dipropylaminobutyl)amino]methylbenzonitrile (2a) may be caused to form a salt with various acids and purified by recrystallization. Examples of the acid include inorganic acids such as hydrochloric acid, hydrobromic acid, hydroiodic acid, sulfuric acid, nitric acid, phosphoric acid and the like, formic acid, acetic acid, trifluoroacetic acid, carbonic acid, lactic acid, adipic acid, maleic acid, fumaric acid, gluconic acid, hippuric acid, malic acid, citric acid, tartaric acid, oxalic acid, malonic acid, succinic acid, propionic acid, butyric acid, glucuronic acid, camphorsulfonic acid, benzoic acid, methanesulfonic acid, benzenesulfonic acid, p-toluenesulfonic acid, terephthalic acid, oleic acid, stearic acid, and the like. Of these, hydrochloric acid is particularly preferable.

Examples of the solvent for the recrystallization include water, methanol, ethanol, isopropanol, tetrahydrofuran, ethylene glycol dimethyl ether, ethyl acetate, hexane, toluene, chloroform, and the like. These solvents may be used alone or in combination with these solvents in an arbitrary ratio. The purity of the salt of 4-[(4-dipropylaminobutyl)amino]methylbenzonitrile (2a) can be increased to 99% or more by recrystallizing the salt of (2a) using a solvent having an appropriate solubility to the salt of (2a). A mixed solvent of isopropanol and methanol is particularly preferably used.

4-[(4-dipropylaminobutyl)amino]methylbenzonitrile (2a) with a purity of 99% or more can be obtained by neutralizing the salt of (2a) with a purity of 99% or more obtained by recrystallization using an appropriate base, extraction using an appropriate organic solvent, washing with water, and concentrating. Examples of the appropriate base include inorganic salts such as sodium hydroxide, potassium hydroxide, lithium hydroxide, sodium carbonate, potassium carbonate, sodium hydrogen carbonate, and potassium hydrogen carbonate, alkoxides such as sodium methoxide, potassium methoxide, sodium ethoxide, potassium ethoxide, sodium t-butoxide, and potassium t-butoxide, and amines such as triethylamine, tri-n-propylamine, tri-n-butylamine, and N,N-diisopropylethylamine. The particularly preferable base is sodium hydroxide, sodium carbonate, or sodium hydrogen carbonate. Examples of the organic solvent suitably used for extraction include hexane, toluene, benzene, chloroform, ethyl acetate, and the like. Of these, toluene and chloroform are particularly preferable.

[Production Step of Benzonitrile Derivative Represented by General Formula (1) by Alkylation Reaction]

In this step, a benzonitrile derivative represented by the general formula (1) is produced by alkylating a benzonitrile derivative of the following formula (2a) in an appropriate solvent. Examples of the alkylation method include a method using an alkyl halide, a dialkylsulfuric acid, an alkyl sulfonate, or the like in the presence of a base, and the like,

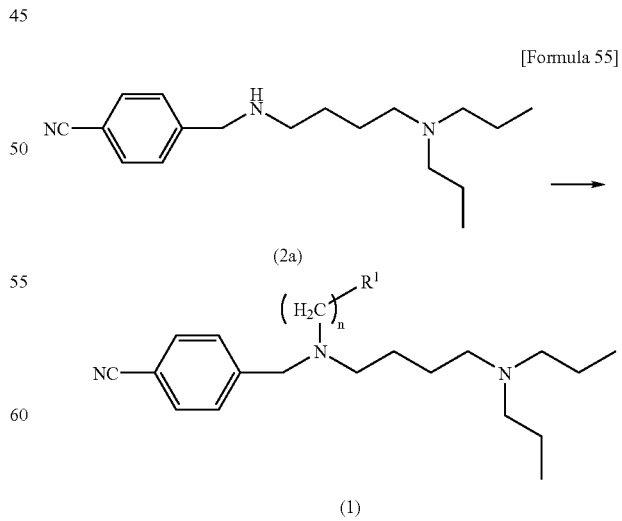

[Formula 55]

(wherein n represents an integer from 0 to 3; and $R^1$ represents hydrogen; a linear or branched alkyl group having 1 to 6 carbon atoms; a halogen atom; a nitro group; a cyano group; a carboxyl group; an amide group; a sulfonyl group; a hydroxyl group; a linear or branched alkoxy group having 1 to 6 carbon atoms; a linear or branched alkylcarbonyl group having 1 to 6 carbon atoms; a linear or branched alkoxycarbonyl group having 1 to 6 carbon atoms; a phenyl group; a phenyl group of which the aromatic ring is substituted by one or more of a halogen atom, a nitro group, a cyano group, a carboxyl group, an amide group, a sulfonyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a benzoyl group; a benzoyl group of which the aromatic ring is substituted by one or more of a halogen atom, a nitro group, a cyano group, a carboxyl group, an amide group, a sulfonyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a benzyloxycarbonyl group, a pyridyl group, a furyl group, an imidazolyl group, a triazolyl group, a tetrazolyl group, a naphthyl group, or a tetrahydrofuryl group, provided that, when n=0, $R^1$ represents hydrogen or a linear or branched alkyl group having 1 to 6 carbon atoms.)

Examples of the solvent suitably used for the alkylation reaction include water, methanol, ethanol, isopropanol, t-butanol, tetrahydrofuran, 1,4-dioxane, cyclopentyl methyl ether, ethylene glycol dimethyl ether, diethylene glycol dimethyl ether, dimethylsulfoxide, N,N-dimethylformamide, N-methyl-2-pyrrolidinone, toluene, benzene, chloroform, and the like. These solvents may be used alone or in combination with these solvents in an arbitrary ratio. Of these, tetrahydrofuran, cyclopentyl methyl ether, N,N-dimethylformamide, and N-methyl-2-pyrrolidinone are particularly preferable.

Examples of the base suitably used for the alkylation reaction include inorganic salts such as sodium hydroxide, potassium hydroxide, lithium hydroxide, sodium carbonate, potassium carbonate, sodium hydrogen carbonate, and potassium hydrogen carbonate, alkoxides such as sodium methoxide, potassium methoxide, sodium ethoxide, potassium ethoxide, sodium t-butoxide, and potassium t-butoxide, and amines such as diisopropylamine, triethylamine, tri-n-propylamine, tri-n-butylamine, N,N-diisopropylethylamine, DMAP (4-dimethylaminopyridine), DBU (1,8-diazabicyclo[5.4.0]undeca-7-ene), DBN (1,5-diazabicyclo[4.3.0]nona-5-ene), and DABCO (1,4-diazabicyclo[2.2.2]octane). Sodium hydride, potassium hydride, or the like may also be used. A particularly preferable base is sodium carbonate, potassium carbonate, diisopropylamine, or N,N-diisopropylethylamine.

In the alkylation reaction, the reaction temperature is 0 to 150° C., and preferably 30 to 100° C. The reaction time is 30 minutes to one day, and preferably two hours to 12 hours.

[Production Step of Benzonitrile Derivative Represented by General Formula (1) by Reductive Alkylation Reaction]

In this step, a benzonitrile derivative represented by the general formula (1) is produced by mixing a benzonitrile derivative of the following formula (2a) with various aldehyde derivative in an appropriate organic solvent, and subjecting the benzonitrile derivative to a reductive alkylation reaction using an appropriate reducing agent. In this reaction, sodium borohydride and sodium triacetoxyborohydride are particularly preferable, but not particularly limited thereto. The benzonitrile derivative represented by the general formula (1) may also be obtained by catalytic reduction in a hydrogen atmosphere. Examples of the catalyst used for the catalytic hydrogenation reduction include Raney nickel, Raney cobalt, and the like, but not particularly limited thereto. Further examples include palladium, platinum, rhodium, ruthenium, and the like. These metals may be used by supporting or not supporting on a carrier such as silica gel, alumina, diatomite, or activated carbon. When applying a catalytic hydrogenation reduction, the catalyst may be repeatedly used several to several tens of times.

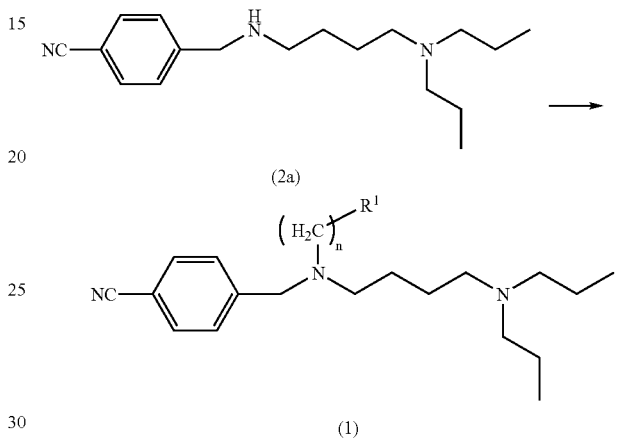

[Formula 56]

(Wherein n and $R^1$ are the same as defined above.)

Examples of the solvent suitably used for the reductive alkylation reaction include methanol, ethanol, isopropanol, t-butanol, tetrahydrofuran, ethylene glycol dimethyl ether, diethylene glycol dimethyl ether, dimethylsulfoxide, N,N-dimethylformamide, N-methyl-2-pyrrolidinone, toluene, benzene, chloroform, and the like. These solvents may be used alone or in combination with these solvents in an arbitrary ratio. Of these, methanol and ethanol are particularly preferable.

As the reducing agent used for the reductive alkylation reaction, formic acid, sodium borohydride, sodium triacetoxyborohydride, sodium cyanoborohydride, or the like may be given. The amount of the reducing agent may be appropriately selected in the range of 1 to 10 equivalents, preferably 1 to 5 equivalents. The amount of the reducing agent is.

The amount of catalyst used for catalytic hydrogenation reduction may be arbitrarily selected in the range of 1 to 30 wt %, preferably 5 to 20 wt %.

The reductive alkylation reaction temperature is −30 to 150° C., and preferably −10 to 100° C. The reaction time is 10 minutes to two days, and preferably 30 minutes to one day.

Production Step of 4-[(4-dipropylaminobutyl)methylamino]methylbenzonitrile(2b)

In this step, 4-[(4-dipropylaminobutyl)methylamino]methylbenzonitrile(2b) is produced by methylating a compound represented by the following formula (2a) in an appropriate organic solvent. Examples of the methylation method include a method using a methyl halide, a dimethylsulfuric acid, a methyl ester of various sulfonic acids, or the like in the presence of a base, and a method of using various reducing agent in 35% formaldehyde aqueous solution. Examples of the reducing agent include formic acid, sodium borohydride, sodium triacetoxyborohydride, sodium cyanoborohydride, and the like. In this reaction, it is preferable to use the various reducing agent in the 35% formaldehyde aqueous solution. In particular, a method of using formic acid in the 35% formaldehyde aqueous solution is preferable.

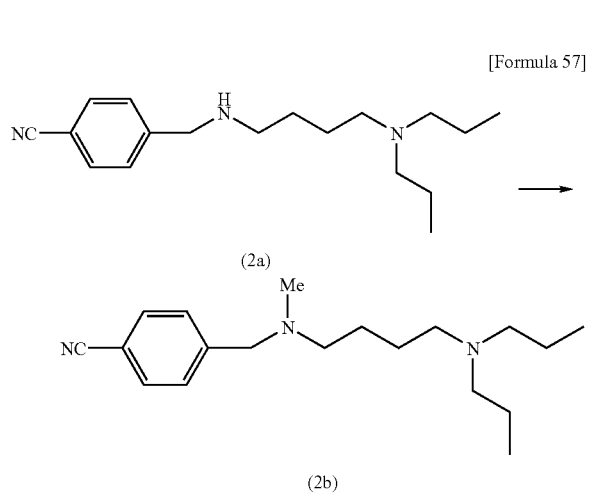

[Formula 57]

(2a)

(2b)

Examples of the solvent suitably used in the method using formic acid include methanol, ethanol, isopropanol, t-butanol, tetrahydrofuran, ethylene glycol dimethyl ether, diethylene glycol dimethyl ether, dimethylsulfoxide, N,N-dimethylformamide, N-methyl-2-pyrrolidinone, toluene, benzene, chloroform, and the like. These solvents may be used alone or in combination with these solvents in an arbitrary ratio. Of these, methanol and ethanol are particularly preferable.

In the method using formic acid, the amount of formic acid may be appropriately selected in the range of 1 to 10 equivalents, preferably 4 to 6 equivalents.

The amount of the 35% formaldehyde aqueous solution may be appropriately selected in the range of 1 to 5 equivalents, preferably 1 to 3 equivalents.

In the method using formic acid, the reaction temperature is 20 to 150° C., and preferably 50 to 100° C. The reaction time is 10 minutes to six hours, and preferably 30 minutes to three hours.

[Production Step of Benzylamine Derivative Represented by General Formula (5)]

In this step, the benzylamine derivative of the following general formula (5) is produced by reducing the benzonitrile derivative represented by the following general formula (1). As the reduction method, a method using various hydride compounds or catalytic hydrogenation reduction using a metal catalyst or a noble metal catalyst may be applied. Examples of the hydride compounds include lithium aluminum hydride, sodium aluminum hydride, lithium triethylborohydride, sodium bis(2-methoxyethoxy)aluminum hydride, and the like, but not particularly limited thereto.

Examples of the catalyst used for catalytic hydrogenation reduction include Raney nickel, Raney cobalt, and the like, but not particularly limited thereto. Further examples include palladium, platinum, rhodium, ruthenium, and the like. These metals may be used by supporting or not supporting on a carrier such as silica gel, alumina, diatomite, or activated carbon. When applying a catalytic hydrogenation reduction, the catalyst may be repeatedly used several to several tens of times. In this reaction, catalytic hydrogenation reduction using Raney nickel is particularly preferable.

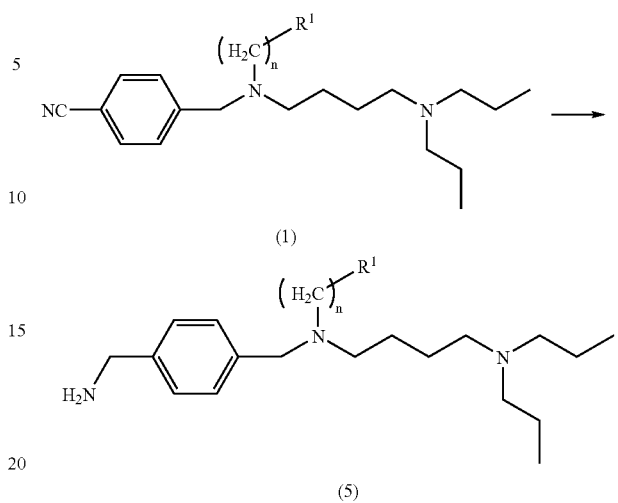

[Formula 58]

(1)

(5)

(Wherein n and $R^1$ are the same as defined above.)

Examples of the solvent suitably used in the catalytic hydrogenation reduction using Raney nickel include water, methanol, ethanol, isopropanol, t-butanol, toluene, and the like. These solvents may be used alone or in combination with these solvents in an arbitrary ratio. The particularly preferable solvent is methanol, ethanol, a mixed solvent of methanol and water, or a mixed solvent of ethanol and water.

Examples of the base suitably used in the catalytic hydrogenation reduction using Raney nickel include sodium hydroxide, potassium hydroxide, lithium hydroxide, sodium methoxide, potassium methoxide, sodium ethoxide, potassium ethoxide, sodium t-butoxide, potassium t-butoxide, ammonia, and the like. The particularly preferable base is sodium hydroxide, sodium methoxide, or sodium ethoxide.

The amount of catalyst used for catalytic hydrogenation reduction using Raney nickel may be arbitrarily selected in the range of 5 to 30 wt %, preferably 10 to 20 wt %.

The reaction temperature is 0 to 100° C., and preferably 10 to 50° C. The reaction time is one hour to five days, and preferably 10 hours to two days.

The resulting crude compound of the benzylamine derivative represented by the general formula (5) may be caused to form a salt with various acids and purified by recrystallization. Examples of the acid include inorganic acids such as hydrochloric acid, hydrobromic acid, hydroiodic acid, sulfuric acid, nitric acid, phosphoric acid and the like, formic acid, acetic acid, trifluoroacetic acid, carbonic acid, lactic acid, adipic acid, maleic acid, fumaric acid, gluconic acid, hippuric acid, malic acid, citric acid, tartaric acid, oxalic acid, malonic acid, succinic acid, propionic acid, butyric acid, glucuronic acid, camphorsulfonic acid, benzoic acid, methanesulfonic acid, benzenesulfonic acid, p-toluenesulfonic acid, terephthalic acid, oleic acid, stearic acid, and the like. Of these, hydrochloric acid is particularly preferable.

Examples of the solvent for the recrystallization include water, methanol, ethanol, isopropanol, tetrahydrofuran, ethylene glycol dimethyl ether, ethyl acetate, hexane, toluene, chloroform, and the like. The solvents may be used either alone or in combination thereof. The purity of the salt of the benzylamine derivative represented by the general formula (5) can be increased to 99% or more by recrystallizing the salt of (5) using a solvent having an appropriate solubility to the salt of (5). A mixed solvent of isopropanol and methanol is particularly preferably used.

The benzylamine derivative represented by the general formula (5) with a purity of 99% or more can be obtained by neutralizing the salt of (5) with a purity of 99% or more obtained by recrystallization using an appropriate base, extracting using an appropriate organic solvent, washing with water, and concentrating. Examples of the appropriate base include inorganic salts such as sodium hydroxide, potassium hydroxide, lithium hydroxide, sodium carbonate, potassium carbonate, sodium hydrogen carbonate, and potassium hydrogen carbonate, alkoxides such as sodium methoxide, potassium methoxide, sodium ethoxide, potassium ethoxide, sodium t-butoxide, and potassium t-butoxide, and amines such as triethylamine, tri-n-propylamine, tri-n-butylamine, N,N-diisopropylethylamine and the like. A particularly preferable base is sodium hydroxide, sodium carbonate, or sodium hydrogen carbonate. Examples of the solvent suitably used for extraction include hexane, toluene, benzene, chloroform, ethyl acetate, and the like. Of these, toluene and chloroform are particularly preferable.

Production Step of 4-[(4-dipropylaminobutyl)amino]methylbenzylamine (5a)

In this step, 4-[(4-dipropylaminobutyl)amino]methylbenzylamine (5a) is produced by reducing the benzonitrile derivative represented by the following general formula (2a). As the reduction method, a method using various hydride compounds or catalytic hydrogenation reduction using a metal catalyst or a noble metal catalyst may be applied. Examples of the hydride compounds include lithium aluminum hydride, sodium aluminum hydride, lithium triethylborohydride, sodium bis(2-methoxyethoxy)aluminum hydride, and the like, but not particularly limited thereto. Examples of the catalyst used for catalytic hydrogenation reduction include Raney nickel, Raney cobalt, and the like, but not particularly limited thereto. Further examples include palladium, platinum, rhodium, ruthenium, and the like. These metals may be used by supporting or not supporting on a carrier such as silica gel, alumina, diatomite, or activated carbon. When applying the catalytic hydrogenation reduction, the catalyst may be repeatedly used several to several tens of times. In this reaction, catalytic hydrogenation reduction using Raney nickel is particularly preferable.

[Formula 59]

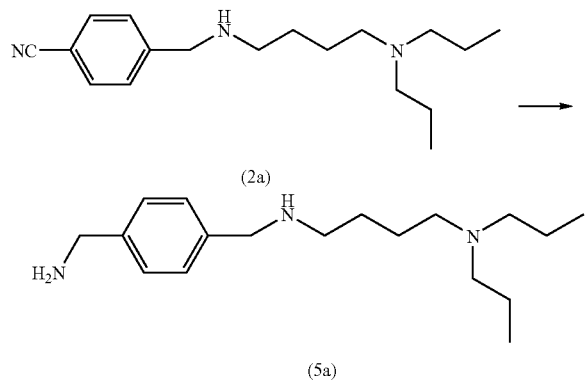

Examples of the solvent suitably used in the catalytic hydrogenation reduction using Raney nickel include water, methanol, ethanol, isopropanol, t-butanol, toluene, and the like. These solvents may be used alone or in combination with these solvents in an arbitrary ratio. The particularly preferable solvent is methanol, ethanol, a mixed solvent of methanol and water, or a mixed solvent of ethanol and water.

Examples of the base suitably used in the catalytic hydrogenation reduction with Raney nickel include sodium hydroxide, potassium hydroxide, lithium hydroxide, sodium methoxide, potassium methoxide, sodium ethoxide, potassium ethoxide, sodium t-butoxide, potassium t-butoxide, ammonia, and the like. The particularly preferable base is sodium hydroxide, sodium methoxide, or sodium ethoxide.

The amount of catalyst used for catalytic hydrogenation reduction using Raney nickel may be arbitrarily selected in the range of 5 to 30 wt %, preferably 10 to 20 wt %.

The reaction temperature is 0 to 100° C., and preferably 10 to 50° C. The reaction time is one hour to five days, and preferably 10 hours to two days.

The resulting unpurified 4-[(4-dipropylaminobutyl)amino]methylbenzylamine (5a) may be caused to form a salt with various acids and purified by recrystallization. Examples of the acid include inorganic acids such as hydrochloric acid, hydrobromic acid, hydroiodic acid, sulfuric acid, nitric acid, phosphoric acid and the like, formic acid, acetic acid, trifluoroacetic acid, carbonic acid, lactic acid, adipic acid, maleic acid, fumaric acid, gluconic acid, hippuric acid, malic acid, citric acid, tartaric acid, oxalic acid, malonic acid, succinic acid, propionic acid, butyric acid, glucuronic acid, camphorsulfonic acid, benzoic acid, methanesulfonic acid, benzenesulfonic acid, p-toluenesulfonic acid, terephthalic acid, oleic acid, stearic acid, and the like. Of these, hydrochloric acid is particularly preferable.

Examples of a recrystallization solvent include water, methanol, ethanol, isopropanol, tetrahydrofuran, ethylene glycol dimethyl ether, ethyl acetate, hexane, toluene, chloroform, and the like. The solvents may be used either alone or in combination thereof. The purity of the salt of 4-[(4-dipropylaminobutyl)amino]methylbenzylamine (5a) can be increased to 99% or more by recrystallization using a solvent having an appropriate solubility to the salt of (5a). A mixed solvent of isopropanol and methanol is particularly preferably used.

4-[(4-dipropylaminobutyl)amino]methylbenzylamine (5a) with a purity of 99% or more can be obtained by neutralizing the salt of (5a) with a purity of 99% or more obtained by recrystallization using an appropriate base, extracting using an appropriate organic solvent, washing with water, and concentrating. Examples of the base include inorganic salts such as sodium hydroxide, potassium hydroxide, lithium hydroxide, sodium carbonate, potassium carbonate, sodium hydrogen carbonate, and potassium hydrogen carbonate, alkoxides such as sodium methoxide, potassium methoxide, sodium ethoxide, potassium ethoxide, sodium t-butoxide, and potassium t-butoxide, and amines such as triethylamine, tri-n-propylamine, tri-n-butylamine, and N,N-diisopropylethylamine. A particularly preferable base is sodium hydroxide, sodium carbonate, or sodium hydrogen carbonate. Examples of a solvent suitably used for extraction include hexane, toluene, benzene, chloroform, ethyl acetate, and the like. Of these, toluene and chloroform are particularly preferable.

[Production Step of Benzylamine Derivative Represented by General Formula (5)]

In this step, 4-[(4-dipropylaminobutyl)amino]methylbenzylamine (5a) is reacted with various aldehydes to protect the primary amino group as an imine derivative, the secondary amino group is subjected to an alkylation reaction in an appropriate organic solvent under weakly acidic to basic conditions, and the imino group is then decomposed and deprotected in an acidic solvent.

[Formation Step of Imine Derivative]

In this step, an imine derivative represented by the following general formula (7) is produced by reacting 4-[(4-dipropylaminobutyl)amino]methylbenzylamine (5a) with various aldehydes represented by the following general formula (6) in an appropriate organic solvent, and protecting the primary amino group. The imine derivative (7) may be used for the subsequent alkylation step without isolation as is, or may be used for the subsequent alkylation step after removing the dehydrating agent and isolating.

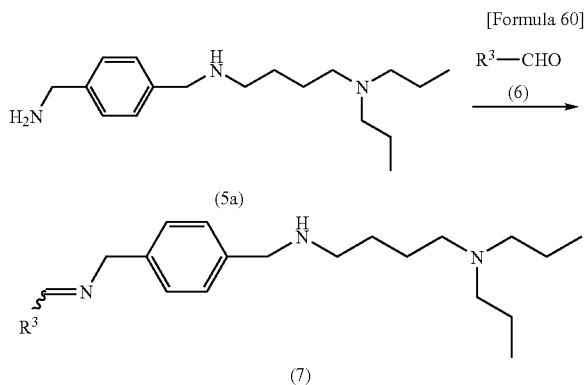

[Formula 60]

(Wherein, $R^3$ represents hydrogen; a linear or branched alkyl group having 1 to 6 carbon atoms; a linear or branched alkoxy group having 1 to 6 carbon atoms; a linear or branched alkylcarbonyl group having 1 to 6 carbon atoms; a linear or branched alkoxycarbonyl group having 1 to 6 carbon atoms; a carboxyl group; a phenyl group; a phenyl group of which the aromatic ring is substituted by one or more of a halogen atom, a nitro group, a cyano group, a carboxyl group, an amide group, a sulfonyl group, a trifluoromethyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a pyridyl group; a pyridyl group of which the ring is substituted by one or more of a halogen atom, a nitro group, a cyano group, a carboxyl group, an amide group, a sulfonyl group, a trifluoromethyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a furyl group; a furyl group of which the ring is substituted by one or more of a halogen atom, a nitro group, a cyano group, a carboxyl group, an amide group, a sulfonyl group, a trifluoromethyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; an imidazolyl group; an imidazolyl group of which the ring is substituted by one or more of a halogen atom, a nitro group, a cyano group, a carboxyl group, an amide group, a sulfonyl group, a trifluoromethyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a naphthyl group; a naphthyl group of which the ring is substituted by one or more of a halogen atom, a nitro group, a cyano group, a carboxyl group, an amide group, a sulfonyl group, a trifluoromethyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a tetrahydrofuryl group; or a tetrahydrofuryl group of which the ring is substituted by one or more of a halogen atom, a nitro group, a cyano group, a carboxyl group, an amide group, a sulfonyl group, a trifluoromethyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group.)

As the aldehyde, the aldehyde represented by the following general formula (6) may be used,

[Formula 61]

$$R^3-CHO \quad (6)$$

(wherein $R^3$ is the same as defined above.)

The aldehyde is preferably an aromatic aldehyde, and more preferably benzaldehyde or 4-methoxybenzaldehyde.

Examples of a solvent suitably used in forming the imine derivative include methanol, ethanol, isopropanol, t-butanol, tetrahydrofuran, ethylene glycol dimethyl ether, diethylene glycol dimethyl ether, dimethylsulfoxide, N,N-dimethylformamide, N-methyl-2-pyrrolidinone, toluene, benzene, chloroform, and the like. These solvents may be used alone or in combination with these solvents in an arbitrary ratio. Of these, methanol and ethanol are particularly preferable.

In this reaction, it is preferable to add a dehydrating agent when forming the imine derivative. Examples of the dehydrating agent include trimethyl orthoformate, triethyl orthoformate, anhydrous sodium sulfate, anhydrous magnesium sulfate, molecular sieve, and the like. A particularly preferable dehydrating agent is trimethyl orthoformate, triethyl orthoformate, or anhydrous sodium sulfate.

The reaction temperature in forming the imine derivative is −30 to 100° C., and preferably 0 to 50° C. The reaction time is one hour to two days, and preferably three hours to one day.

[Alkylation Step]

In this step, the tertiary amine represented by the following general formula (8) is produced by reacting an alkylating agent such as an alkyl halide with the secondary amino group of the imine derivative represented by the following general formula (7) in an appropriate solvent under weakly acidic to basic conditions. The resulting tertiary amine (8) may be used for the subsequent imine decomposition step without isolation as is, or may be used for the subsequent imine decomposition step after isolation.

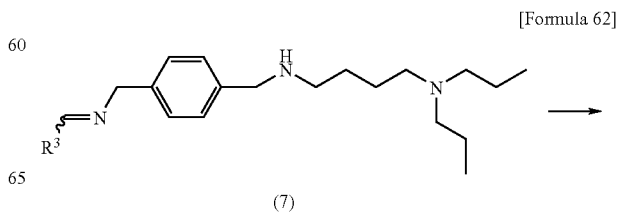

[Formula 62]

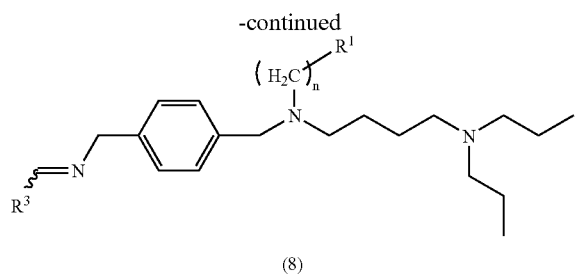

(8)

(Wherein n, $R^1$ and $R^3$ are the same as defined above, provided that a case where —$(CH_2)n$-$R^1$ is hydrogen is excluded.)

Examples of the base suitably used for the alkylation reaction include inorganic salts such as sodium hydroxide, potassium hydroxide, lithium hydroxide, sodium carbonate, potassium carbonate, sodium hydrogen carbonate, and potassium hydrogen carbonate, alkoxides such as sodium methoxide, potassium methoxide, sodium ethoxide, potassium ethoxide, sodium t-butoxide, and potassium t-butoxide, and amines such as diisopropylamine, triethylamine, tri-n-propylamine, tri-n-butylamine, N,N-diisopropylethylamine, DMAP (4-dimethylaminopyridine), DBU (1,8-diazabicyclo[5.4.0]undeca-7-ene), DBN (1,5-diazabicyclo[4.3.0]nona-5-ene), and DABCO (1,4-diazabicyclo[2.2.2]octane). Sodium hydride, potassium hydride, or the like may also be used. Since the imine derivative represented by the general formula (7) has a plurality of amino groups in the structure and functions as a base, the alkylation reaction proceeds rapidly even though a base is not added. Sodium carbonate, potassium carbonate, diisopropylamine, N,N-diisopropylethylamine, or addition of no base is particularly preferable.

Alkylation may be also carried out under weakly acidic conditions where the imino group is not decomposed. Acetic acid/sodium acetate, acetic acid/pyridine, acetic acid/piperidine, or the like may be used.

Examples of a solvent suitably used for alkylation include water, methanol, ethanol, isopropanol, t-butanol, tetrahydrofuran, 1,4-dioxane, cyclopentyl methyl ether, ethylene glycol dimethyl ether, diethylene glycol dimethyl ether, dimethylsulfoxide, N,N-dimethylformamide, N-methyl-2-pyrrolidinone, toluene, benzene, chloroform, and the like. These solvents may be used alone or in combination with these solvents in an arbitrary ratio. Of these, tetrahydrofuran, a mixed solvent of tetrahydrofuran and water, cyclopentyl methyl ether, ethylene glycol dimethyl ether, N,N-dimethylformamide, and N-methyl-2-pyrrolidinone are particularly preferable.

The reaction temperature in the alkylation is –30 to 100° C., and preferably –10 to 60° C. The reaction time is one hour to five days, and preferably three hours to one day.

[Imine Decomposition Step]

In this step, the benzylamine derivative represented by the following general formula (5) is produced by decomposing imino group of the tertiary amine represented by the following general formula (8) in the presence of an excess of acid in an appropriate solvent. The aldehyde represented by the general formula (6) produced after imine decomposition may be easily removed by dissolving the benzylamine derivative (5) in an acidic aqueous solution as a salt and mixing with an appropriate organic solvent, for example. The benzylamine derivative (5) may be isolated by making the aqueous solution basic using an appropriate base and extracting the benzylamine derivative (5) with an appropriate organic solvent.

[Formula 63]

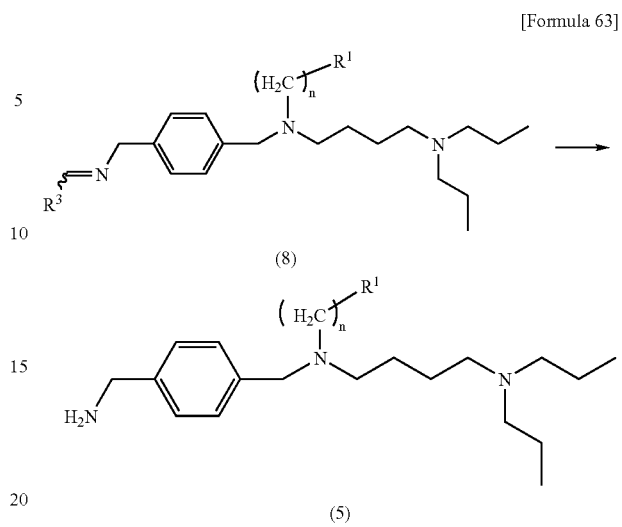

(Wherein n, $R^1$ and $R^3$ are the same as defined above, provided that a case where —$(CH_2)n$-$R^1$ is hydrogen is excluded.)

Examples of the acid used for the imine decomposition step include inorganic acids such as hydrochloric acid, hydrobromic acid, hydroiodic acid, sulfuric acid, nitric acid, phosphoric acid and the like, formic acid, acetic acid, trifluoroacetic acid, methanesulfonic acid, benzenesulfonic acid, p-toluenesulfonic acid, and the like. These acids may be used diluting with water or an organic solvent. Among the above acids, hydrochloric acid and sulfuric acid are particularly preferable.

Examples of a solvent suitably used in the imine decomposition step include water, methanol, ethanol, isopropanol, t-butanol, tetrahydrofuran, ethylene glycol dimethyl ether, diethylene glycol dimethyl ether, dimethylsulfoxide, N,N-dimethylformamide, N-methyl-2-pyrrolidinone, and the like. These solvents may be used alone or in combination with these solvents in an arbitrary ratio. A particularly preferable solvent is water, a mixed solvent of methanol and water, or a mixed solvent of ethanol and water.

The reaction temperature in the imine decomposition step is –10 to 50° C., and preferably 0 to 30° C. The reaction time is 10 minutes to one day, and preferably 1 hour to 10 hours.

The aldehyde represented by the general formula (6) produced after imine decomposition may be easily removed by dissolving the benzylamine derivative (5) in an acidic aqueous solution as a salt and mixing the solution with an appropriate organic solvent immiscible with water (e.g., hexane, toluene, benzene, chloroform, ethyl acetate or the like), for example. Toluene and chloroform are particularly preferable as the organic solvent.

After removing the aldehyde, the benzylamine derivative (5) may be isolated by making the aqueous solution basic using an appropriate base and extracting the benzylamine derivative (5) with an appropriate organic solvent. Examples of the appropriate base include sodium hydroxide, potassium hydroxide, lithium hydroxide, sodium carbonate, potassium carbonate, sodium hydrogen carbonate, potassium hydrogen carbonate, sodium methoxide, potassium methoxide, sodium ethoxide, potassium ethoxide, sodium t-butoxide, potassium t-butoxide, and the like. The particularly preferable base is sodium hydroxide, sodium carbonate, or potassium carbonate. Examples of the organic solvent suitably used for the extraction include hexane, toluene, benzene, chloroform, ethyl acetate, and the like. Toluene and chloroform are particularly preferable.

The crude product of the benzylamine derivative represented by the general formula (5) obtained by the method described above may be caused to form a salt with various acid and purified by recrystallization. Examples of the acid include inorganic acids such as hydrochloric acid, hydrobromic acid, hydroiodic acid, sulfuric acid, nitric acid, phosphoric acid and the like, formic acid, acetic acid, trifluoroacetic acid, carbonic acid, lactic acid, adipic acid, maleic acid, fumaric acid, gluconic acid, hippuric acid, malic acid, citric acid, tartaric acid, oxalic acid, malonic acid, succinic acid, propionic acid, butyric acid, glucuronic acid, camphorsulfonic acid, benzoic acid, methanesulfonic acid, benzenesulfonic acid, p-toluenesulfonic acid, terephthalic acid, oleic acid, stearic acid, and the like. Of these, hydrochloric acid is particularly preferable.

Examples of a recrystallization solvent include water, methanol, ethanol, isopropanol, t-butanol, tetrahydrofuran, ethylene glycol dimethyl ether, ethyl acetate, hexane, toluene, chloroform, and the like. These solvents may be used either alone or in combination thereof. The purity of the salt of the benzylamine derivative (5) can be increased to 99% or more by recrystallizing the salt of (5) using a solvent having an appropriate solubility to the salt of (5). A particularly preferable solvent is a mixed solvent of isopropanol and methanol, a mixed solvent of isopropanol and ethylene glycol dimethyl ether, a mixed solvent of t-butanol and methanol, or a mixed solvent of t-butanol and ethylene glycol dimethyl ether.

The benzylamine derivative (5) with a purity of 99% or more can be obtained by neutralizing the salt of (5) with a purity of 99% or more obtained by recrystallization using an appropriate base, extracting using an appropriate organic solvent, washing with water, and concentrating. Examples of the appropriate base include inorganic salts such as sodium hydroxide, potassium hydroxide, lithium hydroxide, sodium carbonate, potassium carbonate, sodium hydrogen carbonate, and potassium hydrogen carbonate, alkoxides such as sodium methoxide, potassium methoxide, sodium ethoxide, potassium ethoxide, sodium t-butoxide, and potassium t-butoxide, and amines such as triethylamine, tri-n-propylamine, tri-n-butylamine, and N,N-diisopropylethylamine. A particularly preferable base is sodium hydroxide, sodium carbonate, or sodium hydrogen carbonate. Examples of the organic solvent suitably used in the extraction include hexane, toluene, benzene, chloroform, ethyl acetate, and the like. Toluene and chloroform are particularly preferable.

[Production Step (1) of Secondary Amine Derivative Represented by General Formula (9)]

In this step, a benzylamine derivative represented by the general formula (5) is reacted with various aldehydes in an appropriate organic solvent to produce an imine derivative, and the imino group is reduced using an appropriate reducing agent. In this step, a secondary amine derivative (9) is produced by introducing a substituent $R^4$ into the terminal amino group. A secondary amine derivative (9) can be produced from a benzylamine derivative (5a) by combining this step with the steps of [Formula 60] to [Formula 63] described above. A secondary amine derivative represented by the general formula (9) can be produced using readily-available 4-dipropylaminobutyronitrile (3) as a starting raw material by combining this step with the steps of [Formula 53], [Formula 54], [Formula 59], and [Formula 60] to [Formula 63].

[Formation Step of Imine Derivative]

In this step, a benzylamine derivative represented by the following general formula (5) is reacted with various aldehyde represented by the following general formula (6) in an appropriate organic solvent to produce an imine derivative represented by the following general formula (8). The imine derivative (8) may be used as-is for the subsequent reduction step without isolation, or may be used for the subsequent reduction step after removing the dehydrating agent and isolating the imine derivative (8).

[Formula 64]

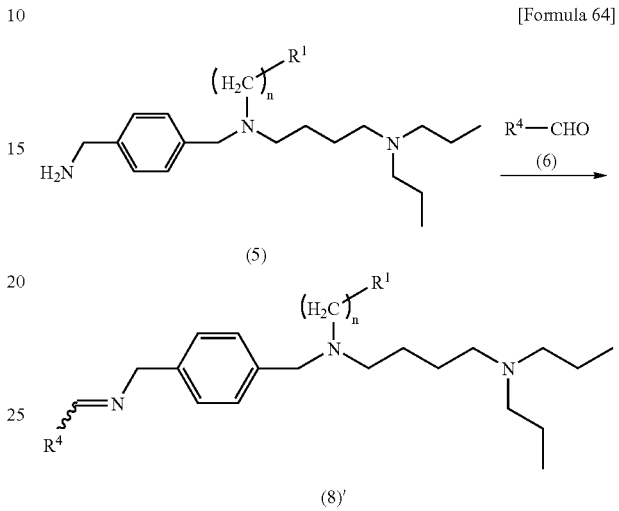

(Wherein n and $R^1$ are the same as defined above, and $R^4$ has the same definition as $R^3$ described above.)

As the aldehyde, the aldehyde represented by the following general formula (6) may be used,

[Formula 65]

(wherein $R^4$ is the same definition as $R^3$ described above.)

The aldehyde is preferably an aromatic aldehyde, and more preferably 2-formyl-1-methylimidazole or 2-formylimidazole.

Examples of the solvent suitably used in forming the imine derivative include methanol, ethanol, isopropanol, t-butanol, tetrahydrofuran, ethylene glycol dimethyl ether, diethylene glycol dimethyl ether, dimethylsulfoxide, N,N-dimethylformamide, N-methyl-2-pyrrolidinone, toluene, benzene, chloroform, and the like. These solvents may be used alone or in combination with these solvents in an arbitrary ratio. Of these, methanol and ethanol are particularly preferable.

In this reaction, it is preferable to add a dehydrating agent when forming the imine derivative. Examples of the dehydrating agent include trimethyl orthoformate, triethyl orthoformate, anhydrous sodium sulfate, anhydrous magnesium sulfate, molecular sieve, and the like. The particularly preferable dehydrating agent is trimethyl orthoformate, triethyl orthoformate, or anhydrous sodium sulfate.

The reaction temperature in forming the imine derivative is −30 to 100° C., and preferably 0 to 50° C. The reaction time is three hours to five days, and preferably six hours to two days.

[Reduction Step]

In this step, an appropriate reducing agent is added to the imine derivative represented by the following general formula (8) in an appropriate organic solvent to produce a secondary amine derivative represented by the following general formula (9). In this reaction, sodium borohydride is particularly preferable as the reducing agent, but not particularly limited thereto. The secondary amine derivative represented by the following general formula (9) may also be obtained by catalytic reduction in a hydrogen atmosphere. Examples of the catalyst used in catalytic hydrogenation reduction include Raney nickel, Raney cobalt, and the like, but not particularly limited thereto. Further examples include palladium, platinum, rhodium, ruthenium, and the like. These metals may be used by supporting or not supporting a carrier such as silica gel, alumina, diatomite, or activated carbon. When applying a catalytic hydrogenation reduction, the catalyst may be repeatedly used several to several tens of times.

[Formula 66]

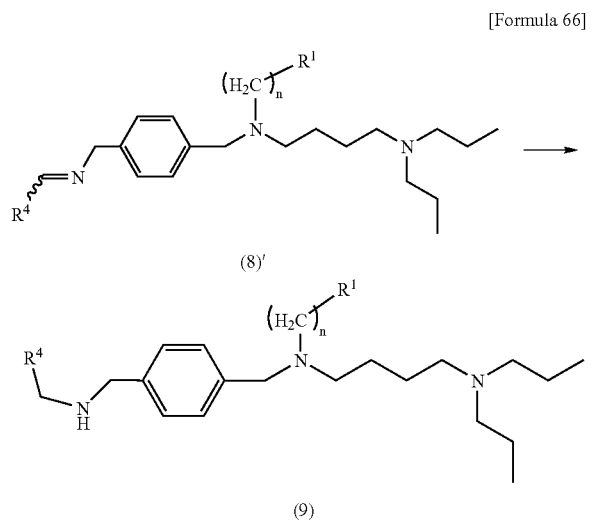

(9)

(Wherein n and $R^1$ are the same as defined above, and $R^4$ has the same definition as $R^3$ described above.)

Examples of the solvent suitably used in the reduction step include methanol, ethanol, isopropanol, t-butanol, tetrahydrofuran, ethylene glycol dimethyl ether, diethylene glycol dimethyl ether, dimethylsulfoxide, N,N-dimethylformamide, N-methyl-2-pyrrolidinone, toluene, benzene, chloroform, and the like. These solvents may be used alone or in combination with these solvents in an arbitrary ratio. Of these, methanol and ethanol are particularly preferable.

As the reducing agent, formic acid, sodium borohydride, sodium triacetoxyborohydride, sodium cyanoborohydride, or the like may be arbitrarily used in an amount of 1 to 5 equivalents, preferably 1 to 3 equivalents. Of these, sodium borohydride is particularly preferable.

The amount of catalyst used in catalytic hydrogenation reduction may be arbitrarily selected in the range of 1 to 30 wt %, preferably 5 to 20 wt %.

The reaction temperature in the reduction step is −30 to 100° C., and preferably −15 to 50° C. The reaction time is 10 minutes to two days, and preferably one hour to one day.

[Production Step (2) of Secondary Amine Derivative Represented by General Formula (9)]

In this step, the primary amino group of 4-[(4-dipropylaminobutyl)amino]methylbenzylamine (5a) is reacted with an aldehyde (6) in an appropriate organic solvent to produce an imine derivative (7), the secondary amino group is subjected to an alkylation reaction in an appropriate organic solvent under weakly acidic to basic conditions, and the imino group is reduced in an appropriate organic solvent. According to this step, a secondary amine derivative represented by the general formula (9) can be produced from 4-[(4-dipropylaminobutyl) amino]methylbenzylamine (5a) without requiring protection/deprotection reactions of the terminal amino group.

[Formation Step of Imine Derivative]

In this step, 4-[(4-dipropylaminobutyl)amino]methylbenzylamine (5a) is reacted with various aldehyde represented by the following general formula (6) in an appropriate organic solvent to produce an imino group and to obtain an imine derivative represented by the following general formula (7). The imine derivative (7) may be directly used for the subsequent alkylation step without isolation as is, or may be used for the subsequent alkylation step after removing a dehydrating agent and isolating the imine derivative (7).

[Formula 67]

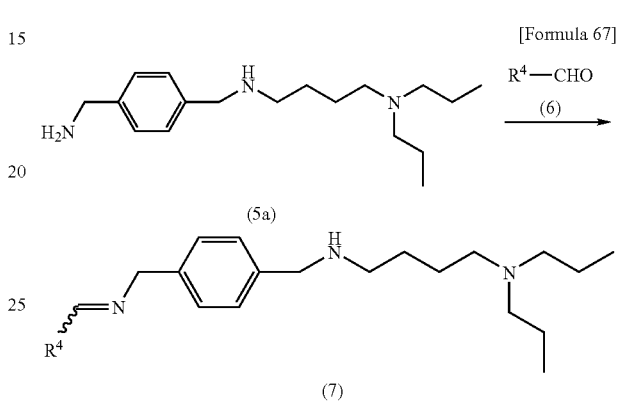

(Wherein $R^4$ is the same definition as $R^3$ described above.)

AS the aldehyde, the aldehyde represented by the following general formula (6) may be used,

[Formula 68]

(wherein $R^4$ is the same definition as $R^3$ described above.

The aldehyde is preferably an aromatic aldehyde, and more preferably 2-formyl-1-methylimidazole or 2-formylimidazole.

Examples of the solvent suitably used in forming the imine derivative include methanol, ethanol, isopropanol, t-butanol, tetrahydrofuran, ethylene glycol dimethyl ether, diethylene glycol dimethyl ether, dimethylsulfoxide, N,N-dimethylformamide, N-methyl-2-pyrrolidinone, toluene, benzene, chloroform, and the like. These solvents may be used alone or in combination with these solvents in an arbitrary ratio. Of these, methanol, ethanol, and tetrahydrofuran are particularly preferable.

In this reaction, it is preferable to add a dehydrating agent when forming the imine derivative. Examples of the dehydrating agent include triethyl orthoformate, triethyl orthoformate, anhydrous sodium sulfate, anhydrous magnesium sulfate, molecular sieve, and the like. The particularly preferable dehydrating agent is trimethyl orthoformate, triethyl orthoformate, or anhydrous sodium sulfate.

The reaction temperature in forming the imine derivative is −30 to 100° C., and preferably 0 to 50° C. The reaction time is three hours to five days, and preferably six hours to two days.

[Alkylation Step]

In this step, a tertiary amine represented by the following general formula (8) is produced by reacting the secondary amino group of the imine derivative represented by the following general formula (7) with an alkylating agent such as an alkyl halide in an appropriate solvent under weakly acidic to basic conditions. The resulting tertiary amine (8) may be used as-is for the subsequent imine decomposition step without isolation, or may be isolated and then used for the subsequent imine decomposition step.

[Formula 69]

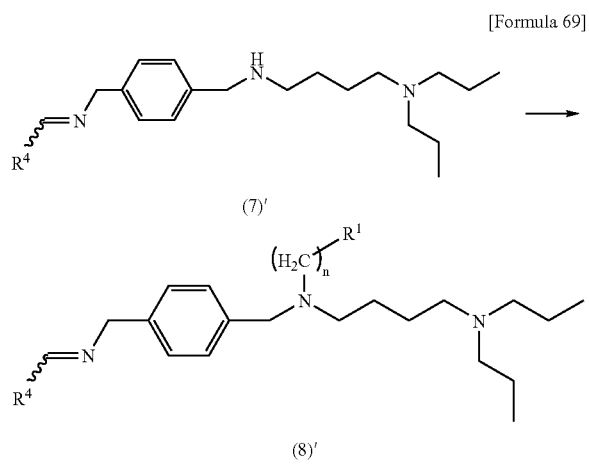

(Wherein n and $R^1$ are the same as defined above, and $R^4$ has the same definition as $R^3$ described above.)

Examples of the base suitably used in the alkylation include inorganic salts such as sodium hydroxide, potassium hydroxide, lithium hydroxide, sodium carbonate, potassium carbonate, sodium hydrogen carbonate, and potassium hydrogen carbonate, alkoxides such as sodium methoxide, potassium methoxide, sodium ethoxide, potassium ethoxide, sodium t-butoxide, and potassium t-butoxide, and amines such as diisopropylamine, triethylamine, tri-n-propylamine, tri-n-butylamine, N,N-diisopropylethylamine, DMAP (4-dimethylaminopyridine), DBU (1,8-diazabicyclo[5.4.0]undeca-7-ene), DBN (1,5-diazabicyclo[4.3.0]nona-5-ene), and DABCO (1,4-diazabicyclo[2.2.2]octane). Sodium hydride, potassium hydride, or the like may also be used. Since the imine derivative represented by the general formula (7) has a plurality of amino groups in the structure and functions as a base, the alkylation reaction proceeds rapidly even if a base is not added. Sodium carbonate, potassium carbonate, diisopropylamine, N,N-diisopropylethylamine, or addition of no base is particularly preferable.

Alkylation may be carried out under weakly acidic conditions where the imino group is not decomposed. Acetic acid/sodium acetate, acetic acid/pyridine, acetic acid/piperidine, or the like may be used.

Examples of the solvent suitably used in the alkylation include water, methanol, ethanol, isopropanol, t-butanol, tetrahydrofuran, 1,4-dioxane, cyclopentyl methyl ether, ethylene glycol dimethyl ether, diethylene glycol dimethyl ether, dimethylsulfoxide, N,N-dimethylformamide, N-methyl-2-pyrrolidinone, toluene, benzene, chloroform, and the like. These solvents may be used alone or in combination with these solvents in an arbitrary ratio. Of these, tetrahydrofuran, a mixed solvent of tetrahydrofuran and water, cyclopentyl methyl ether, ethylene glycol dimethyl ether, N,N-dimethylformamide, and N-methyl-2-pyrrolidinone are particularly preferable.

The reaction temperature in the alkylation is −30 to 100° C., and preferably −10 to 60° C. The reaction time is one hour to five days, and preferably three hours to one day.

[Reduction Step]

In this step, the imine derivative represented by the following general formula (8) is added with an appropriate reducing agent in an appropriate organic solvent to produce a secondary amine derivative represented by the following general formula (9). In this reaction, sodium borohydride is particularly preferable as the reducing agent, but not particularly limited thereto. The secondary amine derivative represented by the following general formula (9) may also be obtained by catalytic reduction in a hydrogen atmosphere. Examples of the catalyst used for catalytic hydrogenation reduction include Raney nickel, Raney cobalt, and the like, but not particularly limited thereto. Further examples include palladium, platinum, rhodium, ruthenium, and the like. These metals may be used by supporting or not supporting on a carrier such as silica gel, alumina, diatomite, or activated carbon. When applying a catalytic hydrogenation reduction, the catalyst may be repeatedly used several to several tens of times.

[Formula 70]

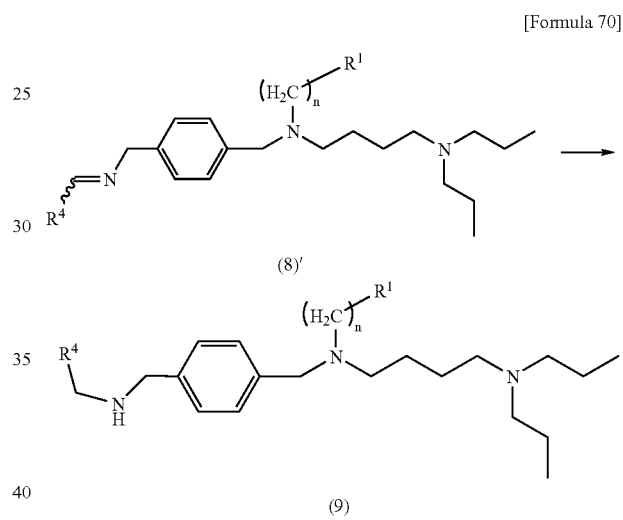

(Wherein n and $R^1$ are the same as defined above, and $R^4$ has the same definition as $R^3$ described above.)

Examples of the solvent suitably used in the reduction step include methanol, ethanol, isopropanol, t-butanol, tetrahydrofuran, ethylene glycol dimethyl ether, diethylene glycol dimethyl ether, dimethylsulfoxide, N,N-dimethylformamide, N-methyl-2-pyrrolidinone, toluene, benzene, chloroform, and the like. These solvents may be used alone or in combination with these solvents in an arbitrary ratio. Of these, methanol and ethanol are particularly preferable.

As the reducing agent, formic acid, sodium borohydride, sodium triacetoxyborohydride, sodium cyanoborohydride, or the like may be arbitrarily used in an amount of 1 to 5 equivalents, preferably 1 to 3 equivalents. Of these, sodium borohydride is particularly preferable.

The amount of catalyst used for catalytic hydrogenation reduction may be arbitrarily selected in the range of 1 to 30 wt %, preferably 5 to 20 wt %.

The reaction temperature in the reduction step is −30 to 100° C., and preferably −15 to 50° C. The reaction time is 10 minutes to two days, and preferably one hour to one day.

The resulting crude product of the above general formula (9) may be caused to form a salt with various acid and purified by recrystallization. Examples of the acid include inorganic acids such as hydrochloric acid, hydrobromic acid, hydroiodic acid, sulfuric acid, nitric acid, phosphoric acid and the like, formic acid, acetic acid, trifluoroacetic acid, carbonic acid, lactic acid, adipic acid, maleic acid, fumaric acid, gluconic acid, hippuric acid, malic acid, citric acid, tartaric acid, oxalic acid, malonic acid, succinic acid, propionic acid, butyric acid, glucuronic acid, camphorsulfonic acid, benzoic acid, methanesulfonic acid, benzenesulfonic acid, and para-toluenesulfonic acid, terephthalic acid, oleic acid, stearic acid, and the like. Of these, sulfuric acid is particularly preferable.

Examples of the solvent for the recrystallization include water, methanol, ethanol, isopropanol, t-butanol, tetrahydrofuran, ethylene glycol dimethyl ether, ethyl acetate, hexane, toluene, chloroform, and the like. These solvents may be used either alone or in combination thereof. The purity of the salt of the secondary amine derivative (9) can be increased to 99% or more by recrystallizing the salt of (9) using a solvent having an appropriate solubility to the salt of (9). Of these, ethanol is particularly preferable.

The secondary amine derivative (9) with a purity of 99% or more can be obtained by neutralizing the salt of (9) with a purity of 99% or more obtained by recrystallization using an appropriate base, extracting using an appropriate organic solvent, washing with water, and concentrating. Examples of an appropriate base include inorganic salts such as sodium hydroxide, potassium hydroxide, lithium hydroxide, sodium carbonate, potassium carbonate, sodium hydrogen carbonate, and potassium hydrogen carbonate, alkoxides such as sodium methoxide, potassium methoxide, sodium ethoxide, potassium ethoxide, sodium t-butoxide, and potassium t-butoxide, and amines such as triethylamine, tri-n-propylamine, tri-n-butylamine, and N,N-diisopropylethylamine. A particularly preferable base is sodium hydroxide, sodium carbonate, or sodium hydrogen carbonate. Examples of the organic solvent suitably used for the extraction include hexane, toluene, benzene, chloroform, ethyl acetate, and the like. Of these, toluene and chloroform are particularly preferable.

[Production Step of Tertiary Amine Derivative Represented by General Formula (10)]

In this step, a tertiary amine derivative represented by the following general formula (10) is produced by reacting the secondary amine derivative represented by the following general formula (9) with an aldehyde (6) in the presence of an appropriate reducing agent in an appropriate organic solvent. In this reaction, sodium triacetoxyborohydride and sodium cyanoborohydride are particularly preferable, but not particularly limited thereto. The tertiary amine derivative (10) may also be obtained by catalytic reduction in a hydrogen atmosphere. Examples of the catalyst used in catalytic hydrogenation reduction include Raney nickel, Raney cobalt, and the like, but not particularly limited thereto. Further examples include palladium, platinum, rhodium, ruthenium, and the like. These metals may be used by supporting or not supporting on a carrier such as silica gel, alumina, diatomite, or activated carbon. When applying a catalytic hydrogenation reduction, the catalyst may be repeatedly used several to several tens of times.

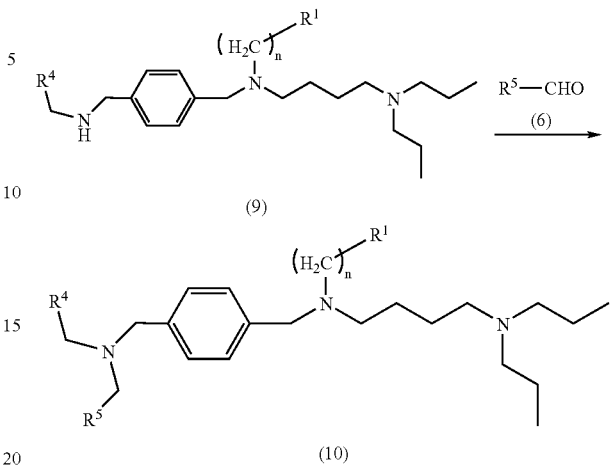

[Formula 71]

(Wherein n and $R^1$ are the same as defined above, and $R^4$ and $R^5$ have the same definition as $R^3$ described above.)

$R^4$ and $R^5$ may be the same or different.

Examples of a solvent suitably used in this step include methanol, ethanol, isopropanol, t-butanol, tetrahydrofuran, ethylene glycol dimethyl ether, diethylene glycol dimethyl ether, dimethylsulfoxide, N,N-dimethylformamide, N-methyl-2-pyrrolidinone, toluene, benzene, chloroform, and the like. These solvents may be used alone or in combination with these solvents in an arbitrary ratio. Of these, methanol and ethanol are particularly preferable.

As the reducing agent, formic acid, sodium borohydride, sodium triacetoxyborohydride, sodium cyanoborohydride, or the like may be arbitrarily used in an amount of 1 to 5 equivalents, preferably 1 to 3 equivalents. Of these, sodium triacetoxyborohydride and sodium cyanoborohydride are particularly preferable.

The amount of catalyst used in catalytic hydrogenation reduction may be arbitrarily selected in the range of 1 to 30 wt, preferably 5 to 20 wt %.

The reaction temperature is −30 to 100° C., and preferably −20 to 50° C. The reaction time is one hour to three days, and preferably three hours to two days.

[Use as Bactericide]

The benzonitrile derivatives represented by the formulas (1) and (2) according to the present invention and agriculturally/horticulturally acceptable salts thereof (hereinafter may be referred to as "compounds of the present invention") have protective effects for various plant diseases given below: *Pyricularia grisea, Cochliobolus miyabeanus, Xanthomonasoryzae, Rhizoctonia solani, Helminthosporium sigmoideun, Gibberella fujikuroi, Pythium aphanidermatum, Podosphaeraleucotricha, Venturia inaequalis, Monilinia mali, Alternaria alternata, Valsa mali, Alternaria kikuchiana, Phyllactinia pyri, Gymnosporangium asiaticum, Venturia nashicola, Uncinula necator, Plasmopara viticola, Glomerella cingulata, Erysiphe graminis* f. sp hordei, *Puccinia graminis, Puccinia striiformis, Pyrenophora graminea, Rhynchosporium secalis, Erysiphe graminis* f. sp tritici, *Puccinia recondita, Puccinia striiformis, Pseudocercosporella herpotrichoides, Microdochium nivale, Leptosphaeria nodorum, Septoria tritici, Sphaerotheca fuliginea, Colletotrichum lagenarium, Pseudoperonospora cubensis, Phytophthora capsici, Erysiphecichoracearum, Alternaria solani, Erysiphe cichoracearum, Sphaerotheca humuli, Erysiphe

*cichoracearum, Cercosporabeticola, Ustillaga maydis, Monilinia fructicola, Botrytis cinerea, Sclerotinia sclerotiorum,* and the like.

The compound of the present invention may be applied as an active component of an agricultural/horticultural disease protective agent as-is without adding any other components. The compound of the present invention is normally mixed with auxiliary agents such as a solid carrier, a liquid carrier, or a surfactant, and formed into various formulation such as a powder, water dispersible powder, granules, emulsion, and the like. These agents are prepared to contain the compound of the present invention as an active component in an amount of 0.1 to 95 wt %, preferably 0.5 to 90 wt %, and more preferably 2 to 80 wt %.

Examples of the auxiliary agents used as carrier, diluent, and surfactant include talc, kaolin, bentonite, diatomaceous earth, white carbon, clay, and the like as the solid carrier, and water, xylene, toluene, chlorobenzene, cyclohexane, cyclohexanone, dimethylsulfoxide, N,N-dimethylformamide, alcohol, and the like as the liquid diluent.

The surfactant is appropriately used depending on its effect. As an emulsifier, polyoxyethylene alkyl aryl ether, polyoxyethylene sorbitan monolaurate, and the like can be given. As a dispersant, lignin sulfonate, dibutylnaphthalene sulfonate, and the like can be given. As a wetting agent, an alkylsulfonate, alkylphenylsulfonate, and the like can be given.

The above agents are classified as an agent which is used as-is and an agent which is diluted with a diluent such as water to a prescribed concentration. When the compound of the present invention is diluted before use, the concentration of the compound is preferably 0.001 to 1.0%. The amount of the compound of the present invention used is preferably 20 to 5000 g per hectare and more preferably 50 to 1000 g per hectare of an agricultural/horticultural field such as a field, a rice field, an orchard, or a greenhouse.

Since the concentration and the amount of the compound of the present invention used vary depending on the form, period, method, place, target crop plants, and the like, the concentration and the amount of the compound may be appropriately adjusted irrespective of the above-mentioned range. The compound of the present invention may be used in combination with a bactericide, an insecticide, an acaricide, or a herbicide.

The present invention is described in detail below by way of examples. Note that the present invention is not limited to the following examples. An NMR spectrum was measured using tetramethylsilane as an internal standard, and is indicated using the following symbol or a combination of these symbols. s: singlet, d: doublet, t: triplet, q: quartet, m: multiplet, bs: broad singlet, dd: double doublet The purity of the synthesized compound was measured by gas chromatography (GC) and high performance liquid chromatography (HPLC).

The compounds shown in the examples can be measured under the following GC conditions.

[GC Measurement Conditions]
Liquid phase: TC-17 (30 m×0.25 mm I.D., manufactured by GL Sciences)
Injector temperature: 280° C.
Detector temperature: 290° C.
Column temperature: held at 100° C. for three minutes, heated to 270° C. at 20° C./min, and held at 270° C. for 50 minutes
Carrier gas: He
Detector: FID The compounds of the examples can be measured under any one of the following HPLC conditions. [HPLC measurement conditions A]
Column: Shodex Asahipak ODP-50 6D (150 mm×6 mm I.D., manufactured by Showa Denko K.K.)
Eluent: MeCN/$H_2O$ (20 mM $Na_2HPO_4$)=60/40
Flow rate: 1.0 ml/min
Detector: UV (225 nm)
Temperature: 40° C.
[HPLC Measurement Conditions B]
Column: Shodex Asahipak ODP-50 6D (150 mm×6 mm I.D., manufactured by Showa Denko K.K.)
Eluent: MeCN/$H_2O$ (20 mM $Na_2HPO_4$)=60/40
Flow rate: 2.0 ml/min
Detector: UV (225 nm)
Temperature: 40° C.
[HPLC Measurement Conditions C]
Column: Shodex Asahipak ODP-50 6D (150 mm×6 mm I.D., manufactured by Showa Denko K.K.)
Eluent: MeCN/$H_2O$ (20 mM $Na_2HPO_4$)/1N NaOHaq.=505/500/5
Flow rate: 1.0 ml/min
Detector: UV (215 nm)
Temperature: 40° C.
[HPLC Measurement Conditions D]
Column: YMC-PACK ODS-AM302 (150×4.6 mm I.D., S-5 μm, 120 angstroms)
(manufactured by YMC Co., Ltd.)
Eluent: prepared by adding sodium octanesulfonate to its concentration of 8 mmol/l to the mixed solution of $H_2O$/MeCN/phosphoric acid (67:33:0.01)
Flow rate: 1.2 ml/min
Detector: UV (210 nm)
Temperature: 40° C.

EXAMPLE 1

Formulation of Raney Nickel Catalyst 6.33 g of sodium hydroxide was charged in a 50 ml Erlenmeyer flask, and dissolved in 30 ml of distilled water, and then the solution was cooled to 0° C. 3.0 g of a Raney nickel reagent (Ni: 50 wt %, Al: 50 wt %) was added little by little to the solution so that the temperature did not rise 25° C. or more. The mixture was then stirred at 25° C. for 15 minutes, at 50° C. for one hour, and at 100° C. for three hours. After cooling the mixture to 25° C., the mixture was allowed to stand to precipitate the catalyst, and a supernatant liquid was removed by decantation. 20 ml of distilled water was added thereto, and stirred for about five minutes, and a supernatant liquid was removed by decantation. This operation was repeated three times. An aqueous solution prepared by dissolving 0.5 g of sodium hydroxide in 5 ml of distilled water was added, and stirred for about five minutes, and a supernatant liquid was removed by decantation. 20 ml of distilled water was added thereto, and stirred for about five minutes, and a supernatant liquid was removed by decantation. This operation was repeated until the distilled water added was neutralized. After confirming that the distilled water was neutralized, the mixture was further washed ten times by the same operation. The mixture was washed 30 times in total. 20 ml of a 95% ethanol aqueous solution was added, and the mixture was stirred for about five minutes, and the ethanol aqueous solution was removed by decantation. This operation was repeated three times. 20 ml of a 99.5% ethanol aqueous solution was added, and stirred for about five minutes, and the ethanol aqueous solution was removed by decantation. This operation was repeated three times to prepare 1.5 g of W-2 Raney nickel. The flask was filled with 99.5% ethanol aqueous solution so that W-2 Raney nickel did not come in contact with the air, and was stored in a refrigerator.

EXAMPLE 2

Production of 4-dipropylaminobutylamine (4)

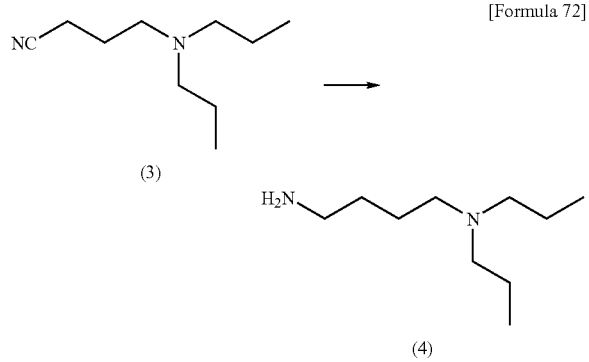

[Formula 72]

30 g (0.178 mol) of 4-dipropylaminobutyronitrile (3) was charged in a 500 ml three-necked flask, 150 ml of ethanol and 90 ml of a 1N sodium hydroxide aqueous solution was added thereto, and the mixture was stirred. 3.0 g of(10 wt %) the Raney nickel prepared in Example 1 was slowly added to the solution. After replacing the atmosphere in the flask with nitrogen and then with hydrogen, the mixture was allowed to react at room temperature for seven days with stirring while using a hydrogen balloon. After confirming that the raw material content had decreased to 1% or less by GC, the reaction solution was filtered through celite and washed with 400 ml of ethanol. After concentrating the filtrate, the residue was dissolved in 400 ml of chloroform and extracted with 200 ml of water. The chloroform layer was washed with 400 ml of a saturated sodium chloride aqueous solution, dried over anhydrous sodium sulfate, and concentrated, thereby obtaining 27.8 g of a colorless oily substance (yield: 90%). The resulting substance was distilled under reduced pressure to obtain 20.5 g of 4-dipropylaminobutylamine (4) (yield: 66.7%, GC: 99%).

Property Values of 4-dipropylaminobutylamine (4)

$^1$H-NMR (400 MHz, CDCl$_3$, ppm): 2.62(t, 2H, J=6.5 Hz, H$_2$NCH$_2$), 2.34-2.25(m, 6H, NCH$_2$×3), 1.41-1.31(m, 8H, NCH$_2$CH$_2$×4), 1.10(bs, 2H, NH$_2$), 0.78(t, 6H, J=7.3 Hz, CH$_3$×2)

EXAMPLE 3

Production of 4-[(4-dipropylaminobutyl)amino]methylbenzonitrile (2a)

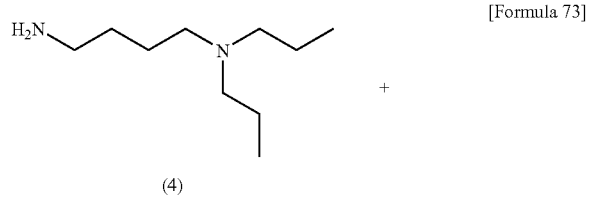

[Formula 73]

3.94 g (0.03 mol, 1.0 equivalent) of 4-cyanobenzaldehyde was charged in a 300 ml four-necked flask, and dissolved in 60 ml of methanol. 9.55 g (0.09 mol, 3.0 equivalents) of trimethyl orthoformate was added dropwise therein at room temperature, and the mixture was then cooled to −20° C. 5.17 g (0.03 mol, 1.0 equivalent) of 4-dipropylaminobutylamine (4) was added dropwise therein, the mixture was stirred for one hour and further stirred at room temperature for three hours. After confirming the disappearance of the raw material, the mixture was again cooled to −20° C. 1.36 g (0.036 mol, 1.2 equivalents) of sodium borohydride was added dropwise therein, and the mixture was stirred for two hours. The reaction solution was added into 250 ml of water and extracted with 120 ml of chloroform. The chloroform layer was washed with 150 ml of a saturated sodium chloride aqueous solution, dried over anhydrous sodium sulfate, and concentrated, thereby obtaining 8.58 g of 4-[(4-dipropylaminobutyl)amino]methylbenzonitrile (2a) as a colorless oily substance (yield: 99%, GC: 96.7%).

Property Values of 4-[(4-dipropylaminobutyl)amino]methylbenzonitrile (2a)

$^{13}$C-NMR (100 MHz, CDCl$_3$, ppm) δ: 146.74, 132.57, 129.00, 119.39, 111.04, 56.68, 54.50, 53.90, 49.87, 28.51, 25.39, 20.64, 12.38

EXAMPLE 4

Production and Recrystallization of 4-[(4-dipropylaminobutyl)amino]methylbenzonitrile hydrochloride (2aa)

8.58 g (0.0299 mol) of unpurified 4-[(4-dipropylaminobutyl)amino]methylbenzonitrile (2a) synthesized in Example 3 was charged in a 300 ml recovery flask, and dissolved in 85 ml of methanol (MeOH). 26.2 g (0.072 mol, 2.4 equivalents) of a 10% hydrochloric acid-methanol solution was added dropwise under cooling with ice, and the mixture was stirred for five hours. The reaction solution was then concentrated. 50 ml of methanol was added to the residue, and the mixture was reconcentrated. This operation was repeated twice to obtain 10.59 g of white crystals (yield: 98%). The crystals were dissolved in 15 ml of methanol, and 90 ml of 2-propanol (IPA) was added to the solution at room temperature (MeOH/IPA=1/6). After allowing the mixture to stand for one day, the precipitated white crystals were recovered by filtration. The crystals were then washed with IPA and dried under reduced pressure to obtain 9.07 g of 4-[(4-dipropylaminobutyl)amino]methylbenzonitrile hydrochloride (2aa) (yield: 84%). m. p. 198 to 200° C.

After dissolving 9.07 g of the resulting hydrochloride (2aa) in 50 ml of water (pH=6.0), the mixture was neutralized with a 25% sodium hydroxide aqueous solution (pH=9.0 to 10.0), followed by extraction with 100 ml of chloroform twice. The chloroform layer was washed with 50 ml of a saturated sodium chloride aqueous solution, dried over anhydrous sodium sulfate, and concentrated, thereby obtaining 6.9 g of 4-[(4-dipropylaminobutyl)amino]methylbenzonitrile (2a) as a colorless oily substance (yield: 97%, GC: 99.4%).

EXAMPLE 5

Production of 4-[(4-dipropylaminobutyl)methylamino]methylbenzonitrile (2b)

[Formula 74]

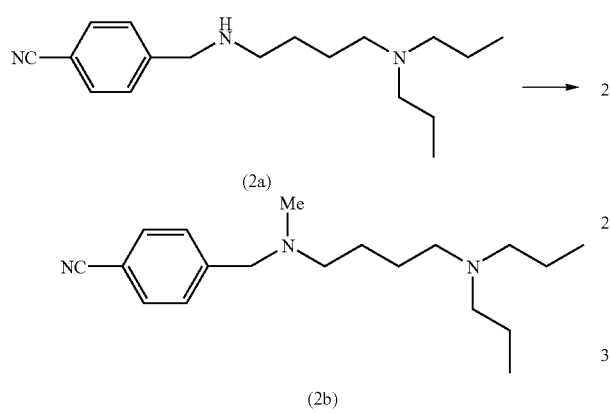

309 mg (1.07 mmol) of 4-[(4-dipropylaminobutyl)amino]methylbenzonitrile (2a) was added dropwise in a 100 ml recovery flask, and dissolved in 9.2 ml of anhydrous methanol. 0.134 ml of a formaldehyde aqueous solution (35%) was then added to the solution. 201.7 mg of sodium cyanoborohydride was then added to the mixture. After the addition of acetic acid to adjust the mixture to pH 5.0, the mixture was stirred at room temperature for 24 hours. 1 mol/l sodium hydroxide aqueous solution was then added to the mixture, followed by extraction with chloroform. The extract was dried over magnesium sulfate and concentrated, thereby obtaining 296.2 mg of 4-[(4-dipropylaminobutyl)methylamino]methylbenzonitrile (2b) was obtained as a colorless oily substance (yield: 92%).

Property Values of 4-[(4-dipropylaminobutyl)methylamino]methylbenzonitrile (2b)

$^1$H-NMR (400 MHz, CDCl$_3$, δppm): 7.61(dd, 2H, J=6.5, 1.8 Hz, Ar—), 7.45(d, 2H, J=8.5 Hz, Ar—), 3.53(s, 2H, ArCH$_2$—N—), 2.35-2.42(m, 8H, N—CH$_2$—×4), 2.19(s, 3H, N—CH$_3$), 1.40-1.51(m, 8H, N—CH$_2$CH$_2$—×4), 0.89(t, 6H, J=7.3 Hz, N—CH$_2$CH$_2$CH$_3$×2)
$^{13}$C-NMR (100 MHz, CDCl$_3$, ppm) δ: 145.50, 131.95, 129.28, 118.94, 110.59, 61.87, 57.53, 56.23, 54.04, 42.22, 25.34, 24.91, 20.24, 11.94

EXAMPLE 6

Production of 4-[(4-dipropylaminobutyl)methylamino]methylbenzonitrile hydrochloride (2ba)

100 mg (0.33 mmol) of unpurified 4-[(4-dipropylaminobutyl)methylamino]methylbenzonitrile (2b) synthesized in Example 5 was charged in a 25 ml recovery flask, and dissolved in 3 ml of methanol. After 290 mg (0.80 mmol, 2.4 equivalents) of a 10% hydrochloric acid-methanol solution was added dropwise to the solution under cooling with ice, the mixture was stirred for one hour. The reaction solution was then concentrated. After the addition of 5 ml of methanol to the residue, the mixture was reconcentrated. This operation was repeated twice, thereby obtaining 122 mg of 4-[(4-dipropylaminobutyl)methylamino]methylbenzonitrile hydrochloride (2ba) as a colorless oily substance (yield: 99%).

EXAMPLE 7

Production of 4-[(4-dipropylaminobutyl)ethoxycarbonylmethylamino]methylbenzonitrile (11)

[Formula 75]

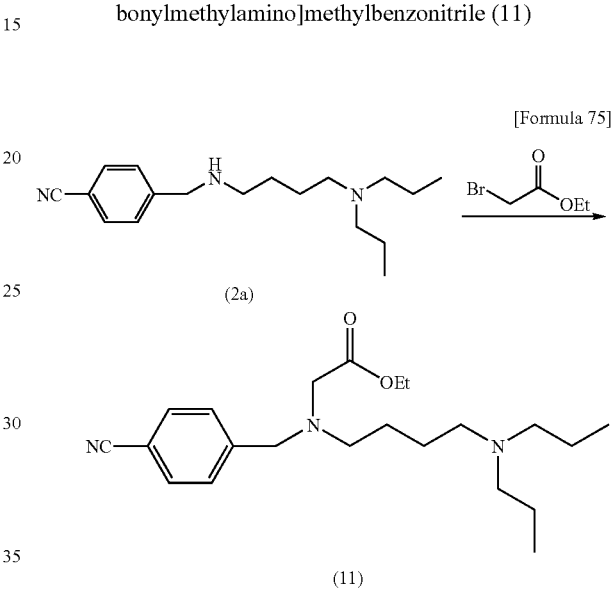

13.4 g (46.6 mmol, 1.0 equivalent) of 4-[(4-dipropylaminobutyl)amino]methylbenzonitrile (2a) and 100 ml of tetrahydrofuran were charged in a 300 ml three-necked flask and dissolved. 7.76 g (56.1 mmol, 1.2 equivalents) of potassium carbonate and 8.20 g (49.1 mmol, 1.05 equivalents) of ethyl bromoacetate were added thereto at room temperature, the mixture was stirred at 60° C. for nine hours. After cooling the mixture to room temperature, salts were removed by filtration, and the solvent was concentrated. The residue was extracted with 250 ml of toluene and 250 ml of a 1N sodium hydroxide aqueous solution. The organic layer was washed with 250 ml of a saturated sodium chloride aqueous solution, dried over anhydrous sodium sulfate, and concentrated, thereby obtaining 13.2 g of 4-[(4-dipropylaminobutyl)ethoxycarbonylmethylamino]methylbenzonitrile (11) as an oily substance (yield: 76%).

Property Values of 4-[(4-dipropylaminobutyl)ethoxycarbonylmethylamino]methylbenzonitrile (11)

$^1$H-NMR (400 MHz, CDCl$_3$, ppm) δ: 7.58(d, 2H, J=8.3 Hz, Ar—), 7.48(d, 2H, J=8.3 Hz, Ar—), 4.15(q, 2H, J=7.1 Hz, —COOCH$_2$CH$_3$), 3.83(s, 2H, ArCH$_2$N), 3.30(s, 2H, —CH$_2$COOEt), 2.61(t, 2H, J=6.8 Hz, ArCH$_2$N—CH$_2$CH$_2$), 2.32(m, 6H, N—CH$_2$CH$_2$×3), 1.40(m, 8H, NCH$_2$CH$_2$×4), 1.26(t, 3H, —COOCH$_2$CH$_3$), 0.85(t, 6H, J=7.3 Hz, NCH$_2$CH$_2$CH$_3$×2)
$^{13}$C-NMR (100 MHz, CDCl$_3$, ppm) δ: 171.21, 145.47, 132.07, 129.22, 118.98, 110.78, 60.31, 58.02, 56.25, 54.32, 53.99, 53.89, 25.56, 24.80, 20.23, 14.25, 11.95

EXAMPLE 8

Production of 4-[(4-dipropylaminobutyl)-4-cyanobenzylamino]methylbenzonitrile (12)

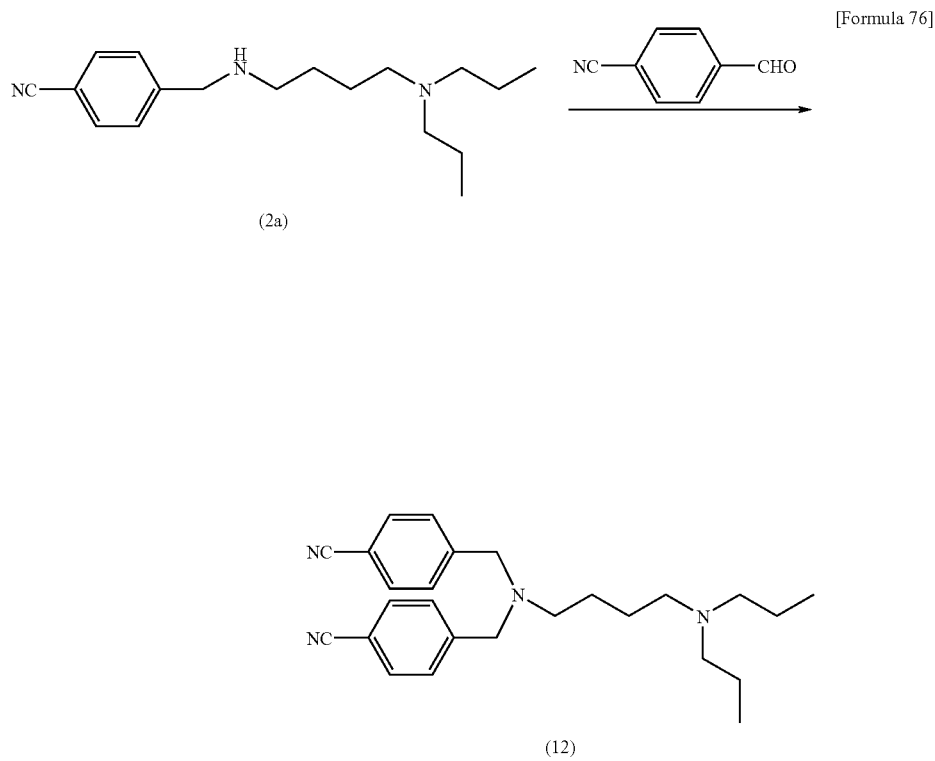

1.0 g (3.47 mmol, 1.0 equivalent) of 4-[(4-dipropylaminobutyl)amino]methylbenzonitrile (2a), 10 ml of ethanol, and 684 mg (5.21 mmol, 1.5 equivalents) of 4-cyanobenzaldehyde were charged in a 100 ml three-necked flask. The mixture was cooled to −30° C. After the addition of 1.47 g (6.95 mmol, 2.0 equivalents) of sodium triacetoxyborohydride, the mixture was stirred for six hours and further stirred at room temperature for 12 hours. After confirming the disappearance of the raw material, the reaction solution was added into 50 ml of a saturated sodium bicarbonate aqueous solution, and extracted with 100 ml of chloroform. The chloroform layer was washed with 50 ml of a saturated sodium chloride aqueous solution, dried over anhydrous sodium sulfate, and concentrated, thereby obtaining 1.35 g of 4-[(4-dipropylaminobutyl)-4-cyanobenzylamino]methylbenzonitrile (12) as a colorless oily substance (yield: 97%, GC: 87%).

Property Values of 4-[(4-dipropylaminobutyl)-4-cyanobenzylamino]methylbenzonitrile (12)

$^1$H-NMR (400 MHz, CDCl$_3$, ppm) δ: 7.60(d, 4H, J=8.4 Hz, Ar—), 7.45(d, 4H, J=8.4 Hz, Ar—), 3.59(s, 4H, ArCH$_2$N), 2.41(t, 2H, J=7.2 Hz, ArCH$_2$NCH$_2$CH$_2$), 2.32(m, 6H, NCH$_2$CH$_2$×3), 1.40(m, 8H, NCH$_2$CH$_2$×4), 0.86(t, 6H, J=7.3 Hz, NCH$_2$CH$_2$CH$_3$×2)

EXAMPLE 9

Production of 4-[(4-dipropylaminobutyl)methylamino]methylbenzonitrile (2b)

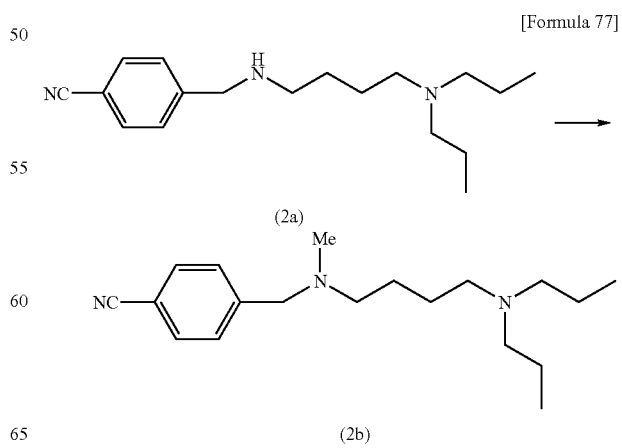

16 g (56 mmol, 1.0 equivalent) of 4-[(4-dipropylaminobutyl)amino]methylbenzonitrile (2a), 50 ml of ethanol, 11.9 g (139 mmol, 2.5 equivalents) of a formaldehyde aqueous solution (35%), and 12.8 g (278 mmol, 5 equivalents) of formic acid were charged in a 300 ml four-necked flask. The mixture was reacted at 80° C. for one hour. The raw material was then disappeared. The reaction solution was slowly added to a solution prepared by dissolving 40 g of sodium hydroxide in 200 ml of distilled water. The reaction solution was extracted with 200 ml of chloroform. This operation was repeated twice. The chloroform layer was then dried over anhydrous sodium sulfate. The solvent was then concentrated, thereby obtaining 16 g of 4-[(4-dipropylaminobutyl)methylamino]methylbenzonitrile (2b) as a slightly yellow oily substance (yield: 95%). [HPLC: 99% (HPLC measurement conditions A)]

EXAMPLE 10

Production of 4-[(4-dipropylaminobutyl)methylamino]methylbenzylamine (13)

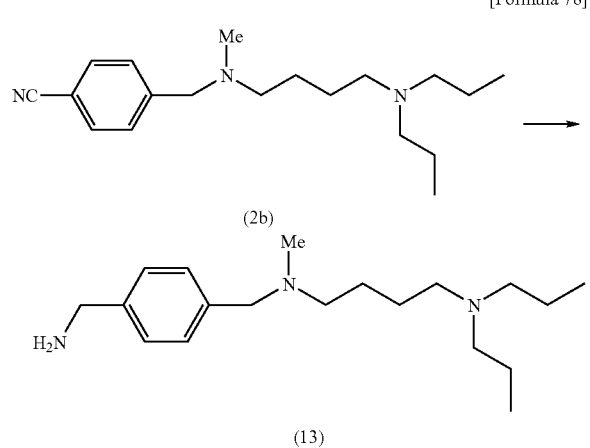

[Formula 78]

14.6 g of 4-[(4-dipropylaminobutyl)methylamino]methylbenzonitrile (2b), 292 ml of ethanol, and 102 ml of a 1N sodium hydroxide aqueous solution were charged in a 1-liter recovery flask. 1.46 g (10 wt %) of Raney nickel prepared using the method described in Example 1 was slowly added to the solution. After replacing the atmosphere in the flask with nitrogen and then with hydrogen, the mixture was stirred at room temperature for 17 hours using a hydrogen balloon. After confirming the disappearance of the raw material, the catalyst was removed by celite filtration, and the product was washed with 70% ethanol solution. The obtained filtrate was concentrated under reduced pressure. After the addition of 100 ml of distilled water to the residue, the product was extracted twice with 200 ml of hexane. The organic layer was washed with 100 ml of a saturated sodium chloride aqueous solution, dried over anhydrous sodium sulfate, and concentrated, thereby obtaining 14.5 g of 4-[(4-dipropylaminobutyl)methylamino]methylbenzylamine (13) as a yellow oily substance (yield: 98%, GC: 93%). [HPLC: 90% (HPLC measurement conditions A)]

Property Values of 4-[(4-dipropylaminobutyl)methylamino]methylbenzylamine (13)

$^1$H-NMR (500 MHz, CDCl$_3$) δ: 7.28(d, 2H, J=8.3 Hz, Ar—), 7.25(d, 2H, J=8.4 Hz, Ar—), 3.85(s, 2H, H$_2$N—CH$_2$—), 3.46(s, 2H, Ar—CH$_2$—NMe), 2.40(t, 2H, J=17.2 Hz, Ar—CH$_2$—N—CH$_2$CH$_2$), 2.36(t, 2H, J=3.5 Hz, NCH$_2$CH$_2$CH$_2$CH$_2$NMe), 2.35(t, 4H, J=2.6 Hz, N—CH$_2$CH$_2$CH$_3$×2), 2.17(s, 3H, —N-Me), 1.39-1.69(m, 8H, N—CH$_2$CH$_2$×4), 0.87(t, 6H, J=7.4 Hz, NCH$_2$CH$_2$CH$_3$×2)

EXAMPLE 11

Production and Recrystallization of 4-[(4-dipropylaminobutyl)methylamino]methylbenzylamine hydrochloride (13a)

14.5 g of unpurified 4-[(4-dipropylaminobutyl)methylamino]methylbenzylamine (13) synthesized in Example 10 and 87 ml of methanol were charged in a 1-liter recovery flask. After the addition of 62.3 g (3.6 equivalents) of a 10% hydrochloric acid-methanol solution while stirring in a water bath, the mixture was stirred at room temperature for 30 minutes. The reaction system was then concentrated under reduced pressure. The resulting solid was recrystallized from IPA/MeOH (=392/44 ml) to obtain 15.2 g of white crystals. These crystals obtained were again recrystallized from IPA/MeOH (=321/32 ml), thereby obtaining 14.5 g of 4-[(4-dipropylaminobutyl)methylamino]methylbenzylamine hydrochloride (13a) as white crystals (yield: 74%). [HPLC: 99.1% (HPLC measurement conditions A)]

14.5 g of the 4-[(4-dipropylaminobutyl)methylamino]methylbenzylamine hydrochloride (13a) obtained was dissolved in 73 ml of water. After the addition of 146 ml of a 1N sodium hydroxide aqueous solution, the product was extracted with 200 ml of hexane, followed by 100 ml of hexane. The organic layer was washed with 100 ml of water, dried over anhydrous sodium sulfate, and concentrated under reduced pressure, thereby obtaining 10.1 g of 4-[(4-dipropylaminobutyl)methylamino]methylbenzylamine (13) as a colorless oily substance (yield: 95%, GC: 99.7%).

EXAMPLE 12

Production of 4-[(4-dipropylaminobutyl)amino]methylbenzylamine (5a)

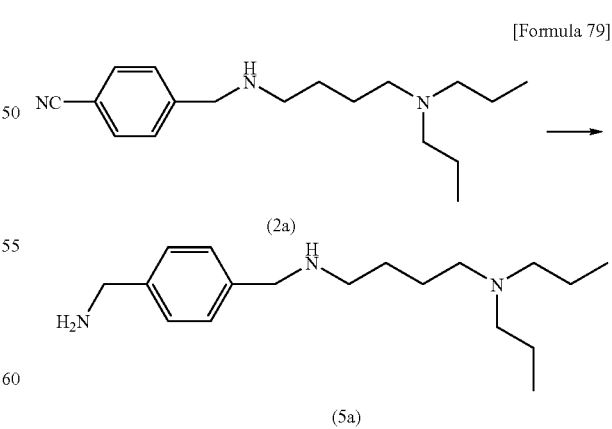

[Formula 79]

4.0 g (13.91 mmol, 1.0 equivalent) of 4-[(4-dipropylaminobutyl)amino]methylbenzonitrile (2a) and 24 ml of methanol were charged in a 100 ml three-necked flask. 400 mg (10 wt %) of the Raney nickel prepared in Example 1 was then slowly added to the mixture. After the addition of 2.58 g (13.35 mmol, 0.96 equivalents) of a 28% sodium methoxide/methanol solution, the atmosphere in the flask was replaced with nitrogen and then with hydrogen. The mixture was then stirred at room temperature for five days using a hydrogen balloon. After completion of the reaction, the reaction solution was filtered through celite. After concentration, the resulting residue was added to 50 ml of water. The product was extracted with 100 ml of chloroform three times. The chloroform layer was washed twice with 100 ml of water, dried over anhydrous sodium sulfate, and concentrated, thereby obtaining 4.0 g of 4-[(4-dipropylaminobutyl)amino]methylbenzylamine (5a) as a colorless oily substance (yield: 99%, GC: 96.0%).

Property Values of 4-[(4-dipropylaminobutyl)amino]methylbenzylamine (5a)

$^1$H-NMR (400 MHz, CDCl$_3$, ppm) δ: 7.29-7.24(m, 4H, Ar—), 3.84(s, 2H, ArCH$_2$NH$_2$), 3.77(s, 2H, ArCH$_2$NHCH$_2$), 2.63(t, 2H, J=6.6 Hz, ArCH$_2$NHCH$_2$CH$_2$), 2.41-2.32(m, 6H, N—CH$_2$CH$_2$×3), 1.47-1.38(m, 8H, N—CH$_2$CH$_2$×4), 0.85(t, 6H, J=7.4 Hz, NCH$_2$CH$_2$CH$_3$×2)

$^{13}$C-NMR (100 MHz, CDCl$_3$, ppm) δ: 141.96, 139.14, 128.28, 127.07, 56.27, 54.15, 53.73, 49.40, 46.25, 28.15, 24.97, 20.26

EXAMPLE 13

Production and Recrystallization of 4-[(4-dipropylaminobutyl)amino]methylbenzylamine hydrochloride (5aa)

7.2 g of unpurified 4-[(4-dipropylaminobutyl)amino]methylbenzylamine (5a) synthesized in Example 12 was diluted with 20 ml of methanol. 32.9 g (3.6 equivalents) of a 10% hydrochloric acid-methanol solution was added dropwise to the mixture under cooling with ice. The mixture was stirred for one hour at a same temperature, and then concentrated. Hexane was added to the residue obtained, and the resulting mixture was azeotropically distillated. This operation was repeated three times to completely remove methanol, thereby obtaining white crystals. The crystals were dissolved in 120 ml of a mixed solvent (IPA:MeOH=3:1) at 70° C. The solution was stirred overnight at room temperature to precipitate white crystals. The crystals were filtered and dried under reduced pressure, thereby obtaining 7.81 g of 4-[(4-dipropylaminobutyl)amino]methylbenzylamine hydrochloride (5aa) (yield: 74.9%). m. p. 205 to 210° C.

7.81 g of the obtained 4-[(4-dipropylaminobutyl)amino]methylbenzylamine hydrochloride (5aa) was dissolved in 50 ml of water. After the addition of a 1N sodium hydroxide aqueous solution (pH=11), the mixture was extracted with 200 ml of chloroform, followed by 100 ml of chloroform. The chloroform layer was washed with 50 ml of water, dried over anhydrous sodium sulfate, and concentrated under reduced pressure, thereby obtaining 5.62 g of 4-[(4-dipropylaminobutyl)amino]methylbenzylamine (5a) as a colorless oily substance (yield: 99%, GC: 99%).

EXAMPLE 14

Production of {[4-(benzylidene)aminomethylbenzyl]-(4-dipropylaminobutyl)}amine (7a)

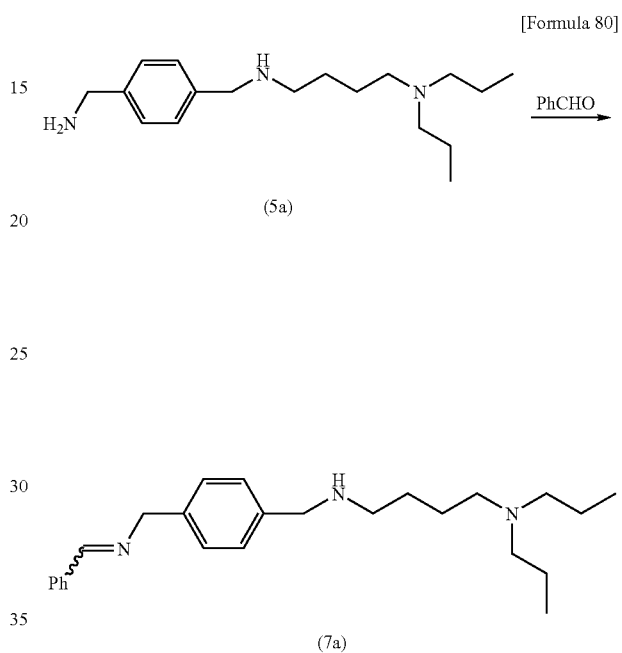

8.69 g (81.9 mmol, 1.02 equivalents) of benzaldehyde, 234 ml of methanol, 23.4 g (80.3 mmol, 1.0 equivalent) of 4-[(4-dipropylaminobutyl)amino]methylbenzylamine (5a), and 17.0 g (161 mmol, 2.0 equivalents) of trimethyl orthoformate were charged in a 1-liter recovery flask. The mixture was reacted at room temperature for six hours. After completion of the reaction, the solvent was concentrated, thereby obtaining 30.5 g of {[4-(benzylidene)aminomethylbenzyl]-(4-dipropylaminobutyl)}amine (7a) as a slightly yellow oily substance (yield: 100%). [HPLC: 96.0% (HPLC measurement conditions A)]

Property Values of {[4-(benzylidene)aminomethylbenzyl]-(4-dipropylaminobutyl)}amine (7a)

$^1$H-NMR (400 MHz, CDCl$_3$, ppm) δ: 8.39(s, 1H, HC═N), 7.78(m, 2H, Ph-), 7.42(m, 3H, Ph-), 7.29(m, 4H, Ar—), 4.81 (s, 2H, ArCH$_2$N═CH), 3.78(s, 2H, ArCH$_2$NHCH$_2$), 2.63(t, 2H, J=6.6 Hz, ArCH$_2$NHCH$_2$CH$_2$), 2.41-2.32(m, 6H, NCH$_2$CH$_2$×3), 1.48-1.40 (m, 8H, NCH$_2$CH$_2$×4), 0.86(t, 6H, J=7.4 Hz, NCH$_2$CH$_2$CH$_3$×2)

$^{13}$C-NMR (100 MHz, CDCl$_3$, ppm) δ: 161.84, 139.36, 137.85, 136.20, 130.70, 128.57, 128.25, 128.02, 64.82, 56.27, 54.17, 53.78, 49.38, 28.19, 24.97, 20.28, 11.99

EXAMPLE 15

Production of {[4-(benzylidene)aminomethylbenzyl]-(4-dipropylaminobutyl)amino}ethyl acetate (8a)

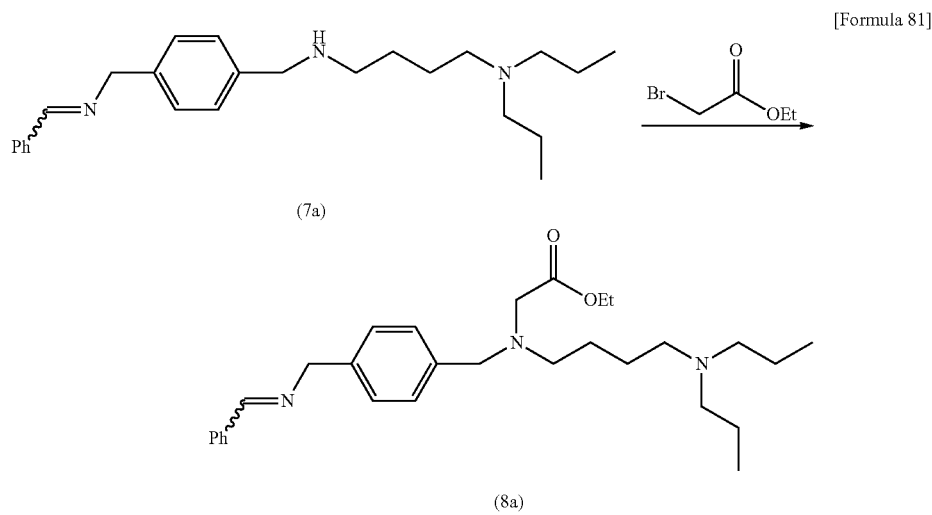

27.0 g (71.1 mmol, 1.0 equivalent) of {[4-(benzylidene)aminomethylbenzyl]-(4-dipropylaminobutyl)}amine (7a), 243 ml of tetrahydrofuran, and 29.5 g (213 mmol, 3.0 equivalents) of potassium carbonate were charged in a 1-liter four-necked flask. The mixture was then stirred. After the addition of 14.2 g (85.3 mmol, 1.2 equivalents) of ethyl bromoacetate, the mixture was reacted at room temperature for 20 hours. The reaction solution was recovered in a recovery flask by decantation, concentrated, and added to 200 ml of chloroform, followed by subjecting to phase separation from 200 ml of water. The product was extracted twice with 100 ml of chloroform, washed twice with 100 ml of a saturated sodium bicarbonate aqueous solution, dried over anhydrous sodium sulfate, and concentrated, thereby obtaining 32.8 g of {[4-(benzylidene)aminomethylbenzyl]-(4-dipropylaminobutyl) amino}ethyl acetate (8a) as a slightly yellow oily substance (yield: 99%).

Property Values of {[4-(benzylidene)aminomethylbenzyl]-(4-dipropylaminobutyl)amino}ethyl acetate (8a)

$^1$H-NMR (400 MHz, CDCl$_3$, ppm) δ: 8.40(s, 1H, —CH=N—), 7.78(m, 2H, -Ph), 7.41(m, 3H, -Ph), 7.31(d, 2H, J=8.2 Hz, Ar—), 7.27(d, 2H, J=8.9 Hz, Ar—), 4.81(s, 2H, ArCH$_2$—N=CH—), 4.14(q, 2H, J=7.1 Hz, —COOCH$_2$CH$_3$), 3.76(s, 2H, ArCH$_2$NCH$_2$), 3.28(s, 2H, —NCH$_2$COOEt), 2.63(dd, 2H, J=6.7, 7.3 Hz, ArCH$_2$NCH$_2$CH$_2$), 2.34(m, 6H, —NCH$_2$CH$_2$—), 1.41(m, 8H, —NCH$_2$CH$_2$—), 1.26(t, 3H, J=7.1 Hz, —COOCH$_2$CH$_3$), 0.85(t, 6H, J=7.4 Hz, CH$_3$CH$_2$CH$_2$N—)

EXAMPLE 16

Production of [(4-aminomethylbenzyl)-(4-dipropylaminobutyl)amino]ethyl acetate (14)

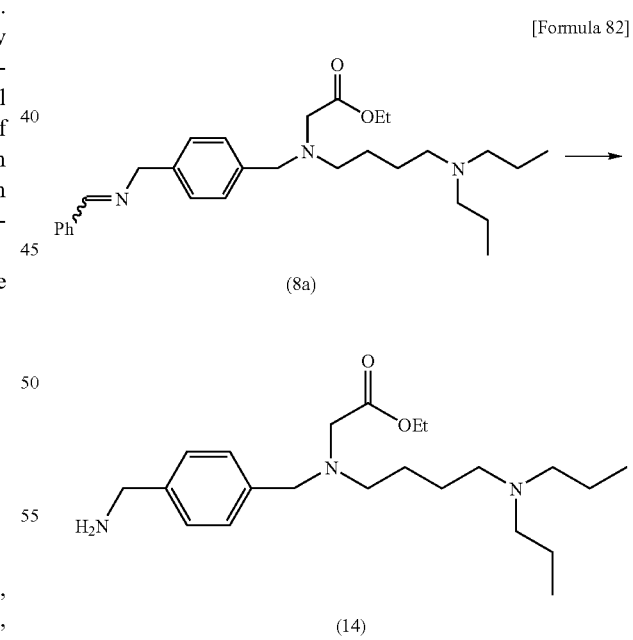

362 ml of 2N hydrochloric acid was charged in a 2-liter four-necked flask and cooled to 0° C. The solution prepared by dissolving 32.8 g of {[4-(benzylidene)aminomethylbenzyl]-(4-dipropylaminobutyl)amino}ethyl acetate (8a) in 120 ml of ethanol was added dropwise to the flask for about 20 minutes, the mixture was stirred at room temperature for three hours. The resultant was extracted five times with 100 ml of toluene. After the addition of 400 ml of chloroform to the aqueous layer, 60 g of sodium carbonate was slowly added to the mixture while stirring to adjust to pH 9. The solution was subjected to phase separation and extracted again with 400 ml of chloroform. The chloroform layer was washed twice with 200 ml of a saturated sodium bicarbonate aqueous solution, washed twice with 200 ml of water, dried over anhydrous sodium sulfate, and concentrated, thereby obtaining 26.3 g of [(4-aminomethylbenzyl)-(4-dipropylaminobutyl)amino] ethyl acetate (14) (yield: 99%, GC: 95%).

Property Values of [(4-aminomethylbenzyl)-(4-dipropylaminobutyl)amino]ethyl acetate (14)

$^1$H-NMR (400 MHz, CDCl$_3$, δppm): 7.31(d, 2H, J=8.0 Hz, Ar—), 7.24(d, 2H, J=8.4 Hz, Ar—), 4.14(q, 2H, J=7.2 Hz, —COOCH$_2$CH$_3$), 3.85(s, 2H, H$_2$NCH$_2$Ar), 3.76(s, 2H, ArCH$_2$NCH$_2$), 3.28(s, 2H, —NCH$_2$COOEt), 2.63(t, 2H, J=7.3 Hz, ArCH$_2$NCH$_2$CH$_2$), 2.31-2.39(m, 6H, —NCH$_2$CH$_2$×3), 1.28-1.48(m, 8H, —NCH$_2$CH$_2$×4), 1.26(t, 3H, J=7.1 Hz, —COOCH$_2$CH$_3$), 0.86(t, 6H, J=7.2Hz, —NCH$_2$CH$_2$CH$_3$×2)

$^{13}$C-NMR (100 MHz, CDCl$_3$, ppm) δ: 171.55, 142.11, 137.69, 129.10, 126.93, 60.10, 57.84, 56.25, 54.13, 54.08, 53.74, 46.18, 25.51, 24.76, 20.26, 14.28, 11.97

EXAMPLE 17

Production and Recrystallization of [(4-aminomethylbenzyl)-(4-dipropylaminobutyl)amino]ethyl acetate hydrochloride (14a)

6.95 g (0.0184 mol) of unpurified [(4-aminomethylbenzyl)-(4-dipropylaminobutyl)amino]ethyl acetate (14) synthesized in Example 16 and 50 ml of ethanol were charged in a 300 ml recovery flask. 9.8 g (0.066 mol, 3.6 equivalents) of a 25% hydrochloric acid-ethanol solution was added dropwise to the flask under cooling with ice, the mixture was warmed and stirred at room temperature for two hours. The reaction solution was then concentrated. After the addition of hexane to the residue, the mixture was reconcentrated, thereby obtaining foam-like slightly yellow crystals. After dissolving the crystals in 65 ml of IPA at 70° C., 50 ml of ethylene glycol dimethyl ether was added to the solution at 70° C. After stirring the mixture for one day, the precipitated white crystals were recovered by filtration. The crystals were then washed with ethylene glycol dimethyl ether and dried under reduced pressure, thereby obtaining 5.8 g of [(4-aminomethylbenzyl)-(4-dipropylaminobutyl)amino]ethyl acetate hydrochloride (14a) (yield: 64%). [HPLC: 99.0% (HPLC measurement conditions A)] m.p. 105 to 106° C.

5.8 g of the obtained [(4-aminomethylbenzyl)-(4-dipropylaminobutyl)amino]ethyl acetate hydrochloride (14a) was dissolved in 30 ml of water. After the addition of a 1N sodium hydroxide aqueous solution (pH=1), the mixture was extracted twice with 100 ml of chloroform. The chloroform layer was washed with 30 ml of water, dried over anhydrous sodium sulfate, and concentrated under reduced pressure, thereby obtaining 4.45 g of [(4-aminomethylbenzyl)-(4-dipropylaminobutyl)amino]ethyl acetate (14) as a colorless oily substance (yield: 99%, GC: 99.3%).

EXAMPLE 18

Production of 4-{[(4-bromobenzyl)-(4-dipropylaminobutyl)amino]methyl}benzonitrile (15)

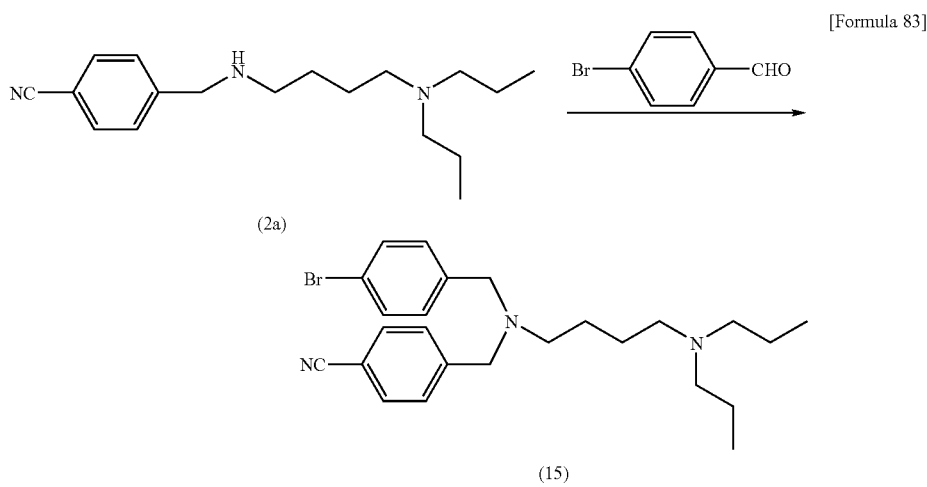

0.40 g (1.39 mmol) of 4-[(4-dipropylaminobutyl)amino]methylbenzonitrile (2a), 8.0 ml of ethanol, and 514 mg (2.78 mmol, 2.0 equivalents) of 4-bromobenzaldehyde were charged in a 50 ml recovery flask under a nitrogen stream. The mixture was then cooled to 0° C. After the addition of 0.707 g (3.34 mmol, 2.4 equivalents) of sodium triacetoxyborohydride, the mixture was stirred for 22 hours. After confirming the disappearance of the raw material by TLC, the reaction solution was added to 50 ml of a saturated sodium bicarbonate aqueous solution, and extracted twice with 50 ml of chloroform. The chloroform layer was washed with 100 ml of a saturated sodium chloride aqueous solution, dried over anhydrous sodium sulfate, concentrated, and purified by silica gel column chromatography (Chromatorex NH (manufactured by FujiSilysia Chemical Ltd.), n-hexane:ethyl acetate=3:1), thereby obtaining 0.508 g of 4-{[(4-bromobenzyl)-(4-dipropylaminobutyl)amino]methyl}benzonitrile (15) as a light yellow oily substance (yield: 80.0%). [HPLC: 96.2% (HPLC measurement conditions B)]

Property Values of 4-{[(4-bromobenzyl)-(4-dipropylaminobutyl)amino]methyl}benzonitrile (15)

$^1$H-NMR (400 MHz, CDCl$_3$, ppm) δ: 7.58(d, 2H, J=8.4Hz, Ar—), 7.43(m, 4H, Ar—), 7.20(d, 2H, J=8.4 Hz, Ar—), 3.56 (s, 2H, ArCH$_2$), 3.49(s, 2H, ArCH$_2$), 2.40(t, 2H, J=7.0 Hz, ArCH$_2$NCH$_2$CH$_2$), 2.30(m, 6H, NCH$_2$CH$_2$×3), 1.43(m, 8H, NCH$_2$CH$_2$×4), 0.85(t, 6H, J=7.3 Hz, NCH$_2$CH$_2$CH$_3$×2)

EXAMPLE 19

Production of 4-{[(4-diethylaminobenzyl)-(4-dipropylaminobutyl)amino]methyl}benzonitrile (16)

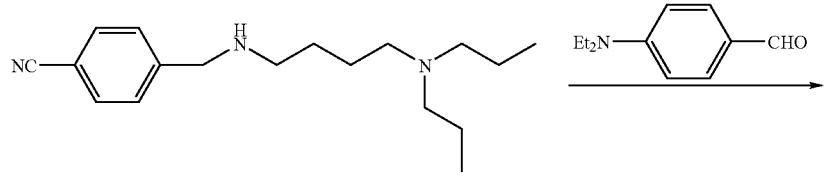

[Formula 84]

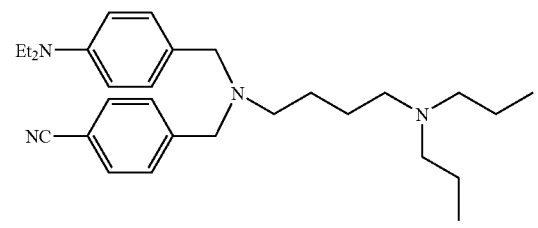

(16)

0.473 g (1.65 mmol) of 4-[(4-dipropylaminobutyl)amino]methylbenzonitrile (2a), 9.5 ml of ethanol, and 583 mg (3.29 mmol, 2.0 equivalents) of 4-diethylaminobenzaldehyde were charged in a 50 ml recovery flask under a nitrogen stream. The mixture was then cooled to 0° C. After the addition of 0.837 g (3.95 mmol, 2.4 equivalents) of sodium triacetoxyborohydride, the mixture was stirred at room temperature for 17 hours. After confirming the disappearance of the raw material by TLC, the reaction solution was added to 50 ml of a saturated sodium bicarbonate aqueous solution, and was extracted twice with 50 ml of chloroform. The chloroform layer was washed with 100 ml of a saturated sodium chloride aqueous solution, dried over anhydrous sodium sulfate, concentrated, and purified by silica gel column chromatography (Chromatorex NH, chloroform:n-hexane=1:1), thereby obtaining 0.252 g of 4-{[(4-diethylaminobenzyl)-(4-dipropylaminobutyl)amino]methyl}benzonitrile (16) as a light yellow oily substance (yield: 34.1%). [HPLC: 98.7% (HPLC measurement conditions B)]

Property Values of 4-{[(4-diethylaminobenzyl)-(4-dipropylaminobutyl)amino]methyl}benzonitrile (16)

$^1$H-NMR (400 MHz, CDCl$_3$, ppm) δ: 7.56(d, 2H, J=8.4 Hz, Ar—), 7.45(d, 2H, J=8.4 Hz, Ar—), 7.14(d, 2H, J=8.8 Hz, Ar—), 6.62(d, 2H, J=8.8 Hz, Ar—), 3.55(s, 2H, ArCH$_2$N), 3.45(s, 2H, ArCH$_2$N), 3.33(q, 4H, J=7.0 Hz, Ar—NCH$_2$CH$_3$×2), 2.40(t, 2H, J=7.0 Hz, ArCH$_2$NCH$_2$CH$_2$), 2.32(m, 6H, NCH$_2$CH$_2$×3), 1.43(m, 8H, NCH$_2$CH$_2$×4), 1.15(t, 6H, J=7.0 Hz, ArNCH$_2$CH$_3$×2), 0.85 (t, 6H, J=7.3 Hz, NCH$_2$CH$_2$CH$_3$×2)

EXAMPLE 20

Production of 4-{[(4-dipropylaminobutyl)-(5-methylfuran-2-ylmethyl)amino]methyl}benzonitrile (17)

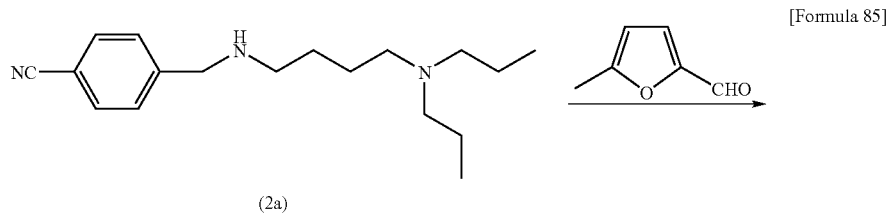

[Formula 85]

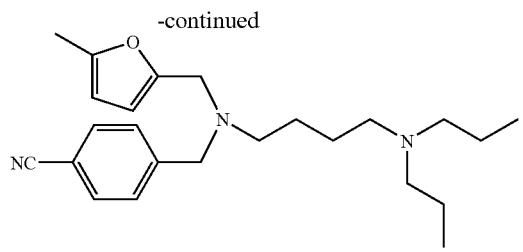

(17)

0.485 g (1.69 mmol) of 4-[(4-dipropylaminobutyl)amino]methylbenzonitrile (2a), 9.7 ml of ethanol, and 371 mg (3.37 mmol, 2.0 equivalents) of 5-methyl-2-furaldehyde were charged in a 50 ml recovery flask under a nitrogen stream. The mixture was then cooled to 0° C. After the addition of 0.857 g (4.05 mmol, 2.4 equivalents) of sodium triacetoxyborohydride, the mixture was stirred at room temperature for 19 hours. After confirming the disappearance of the raw material by TLC, the reaction solution was added to 50 ml of a saturated sodium bicarbonate aqueous solution, and extracted twice with 50 ml of chloroform. The chloroform layer was washed with 100 ml of a saturated sodium chloride aqueous solution, dried over anhydrous sodium sulfate, concentrated, and purified by silica gel column chromatography (Chromatorex NH, chloroform:n-hexane=11:1), thereby obtaining 0.640 g of 4-{[(4-dipropylaminobutyl)-(5-methylfuran-2-ylmethyl)amino]methyl}benzonitrile (17) as a light yellow oily substance (yield: 99.5%). [HPLC: 98.9% (HPLC measurement conditions B)]

Property Values of 4-{[(4-dipropylaminobutyl)-(5-methylfuran-2-ylmethyl)amino]methyl}benzonitrile (17)

$^1$H-NMR (400 MHz, CDCl$_3$, ppm) δ: 7.58(d, 2H, J=8.4 Hz, Ar—), 7.46(d, 2H, J=8.4 Hz, Ar—), 6.01(d, 1H, J=3.0 Hz, Ar—), 5.87(d, 1H, J=3.0 Hz, Ar—), 3.62(s, 2H, ArCH$_2$N), 3.56(s, 2H, ArCH$_2$N), 2.46(t, 2H, J=7.0 Hz, ArCH$_2$NCH$_2$CH$_2$), 2.34(m, 6H, NCH$_2$CH$_2$×3), 2.26(s, 3H, ArCH$_3$), 1.43(m, 8H, NCH$_2$CH$_2$×4), 0.86(t, 6H, J=7.3 Hz, NCH$_2$CH$_2$CH$_3$×2)

EXAMPLE 21

Production of 4-{[(4-dipropylaminobutyl)-(1H-pyrrol-2-ylmethyl)amino]methyl}benzonitrile (18)

[Formula 86]

(18)

0.492 g (1.71 mmol) of 4-[(4-dipropylaminobutyl)amino]methylbenzonitrile (2a), 9.8 ml of ethanol, and 0.325 g (3.42 mmol, 2.0 equivalents) of pyrrole-2-aldehyde were charged in a 50 ml recovery flask under a nitrogen stream. The mixture was then cooled to 0° C. After the addition of 0.870 g (4.11 mmol, 2.4 equivalents) of sodium triacetoxyborohydride, the mixture was stirred at room temperature for 17 hours. After confirming the disappearance of the raw material by TLC, the reaction solution was added to 50 ml of a saturated sodium bicarbonate aqueous solution, and extracted twice with 50 ml of chloroform. The chloroform layer was washed with 100 ml of a saturated sodium chloride aqueous solution, dried over anhydrous sodium sulfate, concentrated, and purified by silica gel column chromatography (Chromatorex NH, chloroform:n-hexane=1:1), thereby obtaining 0.342 g of 4-{[(4-dipropylaminobutyl)-(1H-pyrrol-2-ylmethyl)amino]methyl}benzonitrile (18) as a light yellow oily substance (yield: 54.5%). [HPLC: 87.6% (HPLC measurement conditions B)]

Property Values of 4-{[(4-dipropylaminobutyl)-(1H-pyrrol-2-ylmethyl)amino]methyl}benzonitrile (18)

$^1$H-NMR (400 MHz, CDCl$_3$, ppm) δ: 8.46(bs, 1H, NH), 7.58(d, 2H, J=8.4 Hz, Ar—), 7.41(d, 2H, J=8.4 Hz, Ar—), 6.72(bs, 1H, Ar—), 6.11(bs, 1H, Ar—), 6.02(bs, 1H, Ar—), 3.57(s, 2H, ArCH$_2$N), 3.56(s, 2H, ArCH$_2$N), 2.42(t, 2H, J=7.0 Hz, ArCH$_2$NCH$_2$CH$_2$), 2.35(m, 6H, NCH$_2$CH$_2$×3), 1.43(m, 8H, NCH$_2$CH$_2$×4), 0.86(t, 6H, J=7.3 Hz, NCH$_2$CH$_2$CH$_3$×2)

EXAMPLE 22

Production of 4-{[(4-dipropylaminobutyl)-4-methoxybenzyl]amino]-methyl}-benzonitrile (19)

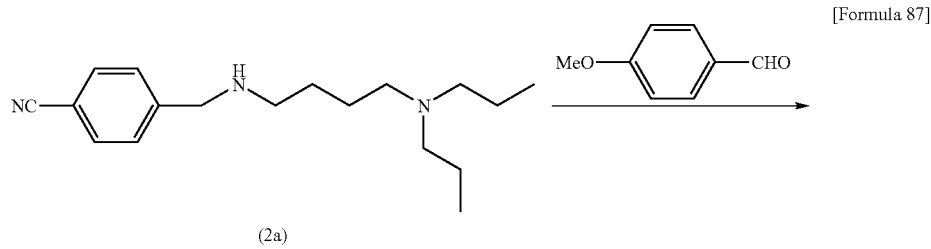

[Formula 87]

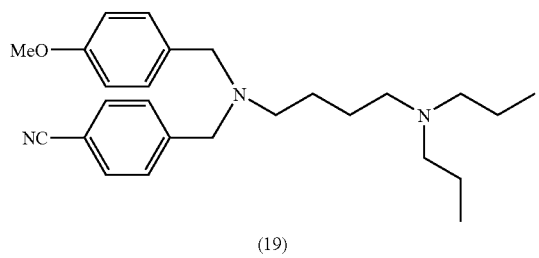

(19)

0.570 g (1.98 mmol) of 4-[(4-dipropylaminobutyl)amino]methylbenzonitrile (2a), 11.4 ml of ethanol, and 0.540 g (3.97 mmol, 2.0 equivalents) of 4-methoxybenzaldehyde were charged in a 50 ml recovery flask under a nitrogen stream. The mixture was then cooled to 0° C. After the addition of 1.009 g (4.76 mmol, 2.4 equivalents) of sodium triacetoxyborohydride, the mixture was stirred at room temperature for 18 hours. After confirming the disappearance of the raw material by TLC, the reaction solution was added to 50 ml of a saturated sodium bicarbonate aqueous solution, and extracted twice with 50 ml of chloroform. The chloroform layer was washed with 100 ml of a saturated sodium chloride aqueous solution, dried over anhydrous sodium sulfate, concentrated, and purified by silica gel column chromatography (Chromatorex NH, chloroform:n-hexane=1:1), thereby obtaining 0.559 g of 4-{[(4-dipropylaminobutyl)-(4-methoxybenzyl)amino]-methyl}-benzonitrile (19) as a light yellow oily substance (yield: 69.2%). [HPLC: 99.4% (HPLC measurement conditions B)]

Property Values of 4-{[(4-dipropylaminobutyl)-(4-methoxybenzyl)amino]-methyl}-benzonitrile (19)

$^1$H-NMR (400 MHz, CDCl$_3$, ppm) δ: 7.57(d, 2H, J=8.4 Hz, Ar—), 7.45(d, 2H, J=8.4 Hz, Ar—), 7.23(d, 2H, J=8.7 Hz, Ar—), 6.84(d, 2H, J=8.7 Hz, Ar—), 3.79(s, 3H, —OCH$_3$), 3.55(s, 2H, ArCH$_2$N), 3.49(s, 2H, ArCH$_2$N), 2.40(t, 2H, J=7.0 Hz, ArCH$_2$NCH$_2$CH$_2$), 2.30(m, 6H, NCH$_2$CH$_2$×3), 1.43(m, 8H, NCH$_2$CH$_2$×4), 0.85(t, 6H, J=7.3 Hz, NCH$_2$CH$_2$CH$_3$×2)

EXAMPLE 23

Production of [(4-cyanobenzyl)-(4-dipropylaminobutyl)amino]benzyl acetate (20)

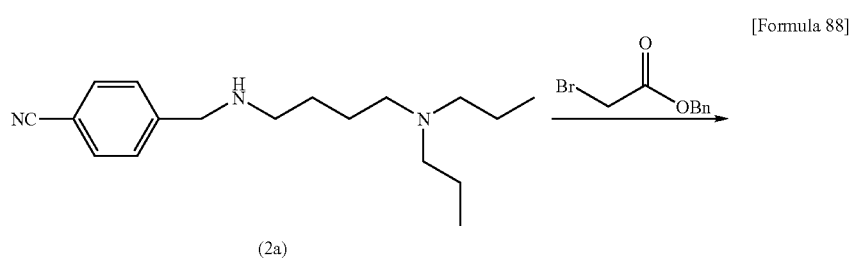

[Formula 88]

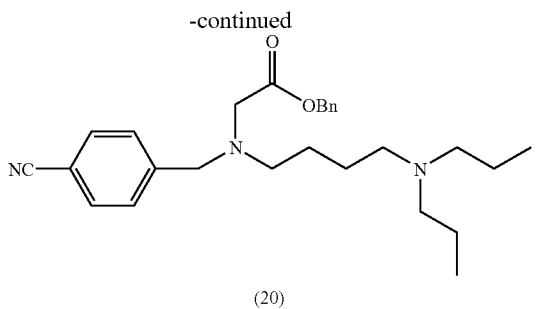

(20)

In a 50 ml recovery flask, 0.462 g (1.61 mmol, 1.0 equivalent) of 4-[(4-dipropylaminobutyl)amino]methylbenzonitrile (2a) and 9.2 ml of cyclopentyl methyl ether were charged and dissolved under a nitrogen stream. After the addition of 0.666 g (4.82 mmol, 3.0 equivalents) of potassium carbonate and 0.736 g (3.21 mmol, 2.0 equivalents) of benzyl bromoacetate at room temperature, the mixture was stirred at room temperature for 19 hours. After confirming the disappearance of the raw material by TLC, the reaction solution was added to 100 ml of a saturated sodium bicarbonate aqueous solution, and was extracted twice with 100 ml of chloroform. The chloroform layer was washed with 100 ml of a saturated sodium chloride aqueous solution, dried over anhydrous sodium sulfate, concentrated, and purified by silica gel column chromatography (Chromatorex NH, n-hexane:ethyl acetate=4:1), thereby obtaining 0.128 g of [(4-cyanobenzyl)-(4-dipropylaminobutyl)amino]benzyl acetate (20) as a light yellow oily substance (yield: 18.3%). [HPLC: 97.8% (HPLC measurement conditions A)]

Property Values of [(4-cyanobenzyl)-(4-dipropylaminobutyl)amino]benzyl acetate (20)

$^1$H-NMR (400 MHz, CDCl$_3$, ppm) δ: 7.56(d, 2H, J=8.4 Hz, Ar—), 7.44(d, 2H, J=8.4 Hz, Ar—), 7.34(m, 5H, Ar—)5.13(s, 2H, ArCH$_2$O), 3.82(s, 2H, ArCH$_2$N), 3.36(s, 2H, —NCH$_2$COOBn), 2.62(t, 2H, J=7.0 Hz, ArCH$_2$NCH$_2$CH$_2$), 2.33(m, 6H, NCH$_2$CH$_2$×3), 1.40(m, 8H, NCH$_2$CH$_2$×4), 0.85 (t, 6H, J=7.3 Hz, NCH$_2$CH$_2$CH$_3$×2)

EXAMPLE 24

Production of 3-[(4-cyanobenzyl)-(4-dipropylaminobutyl)amino]ethyl propionate (21)

[Formula 89]

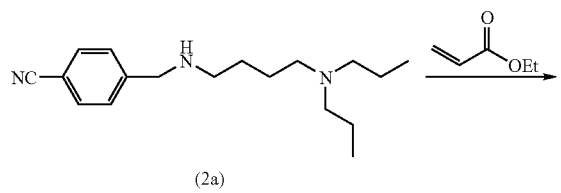

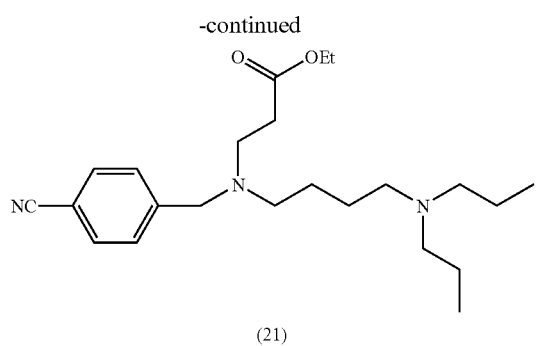

(21)

In a 50 ml recovery flask, 0.546 g (1.90 mmol, 1.0 equivalent) of 4-[(4-dipropylaminobutyl)amino]methylbenzonitrile (2a) and 5.5 ml of ethanol were charged under a nitrogen stream and dissolved. After the addition of 0.190 g (1.90 mmol, 1.0 equivalent) of ethyl acrylate at room temperature, the mixture was stirred at room temperature for four hours. After the addition of 0.190 g (1.90 mmol, 1.0 equivalent) of ethyl acrylate, the mixture was stirred at 60° C. for 24 hours. After the addition of 0.190 g (1.90 mmol, 1.0 equivalent) of ethyl acrylate, the mixture was stirred at 60° C. for 20 hours. After confirming the disappearance of the raw material by TLC, the reaction solution was concentrated under reduced pressure as-is, and azeotropically distilled three times with chloroform, thereby obtaining 0.733 g of 3-[(4-cyanobenzyl)-(4-dipropylaminobutyl)amino]ethyl propionate (21) as a colorless oily substance (yield: 99.6%). [HPLC: 92.9% (HPLC measurement conditions B)]

Property Values of 3-[(4-cyanobenzyl)-(4-dipropylaminobutyl)amino]ethyl propionate (21)

$^1$H-NMR (400 MHz, CDCl$_3$, ppm) δ: 7.58(d, 2H, J=8.4 Hz, Ar—), 7.43(d, 2H, J=8.4 Hz, Ar—), 4.11(q, 2H, J=7.1 Hz, OCH$_2$CH$_3$), 3.61(s, 2H, ArCH$_2$N), 2.80(t, 2H, J=7.1 Hz, NCH$_2$CH$_2$CO$_2$Et), 2.38(m, 10H, NCH$_2$CH$_2$×4, NCH$_2$CH$_2$CO$_2$Et), 1.40(m, 8H, NCH$_2$CH$_2$×4), 1.24(t, 3H, J=7.1 Hz, CO$_2$CH$_2$CH$_3$), 0.85(t, 6H, J=7.3 Hz, NCH$_2$CH$_2$CH$_3$)

EXAMPLE 25

Production of {(4-dipropylaminobutyl)-[4-(4-methoxybenzylidene)aminomethylbenzyl]}amine (22)

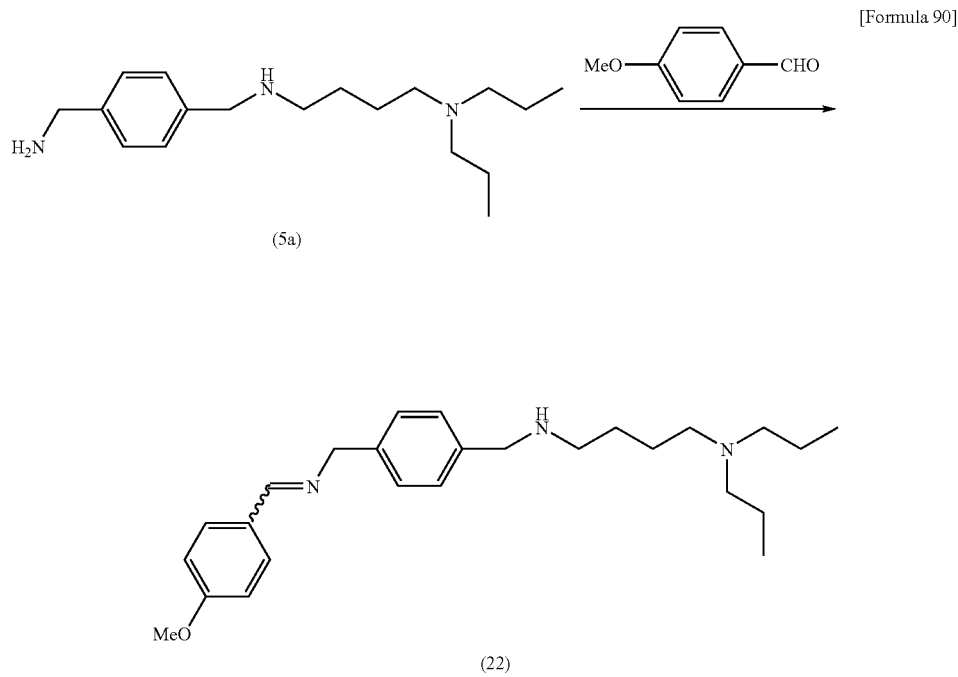

Under a nitrogen stream 467 mg (3.43 mmol, 1.0 equivalent) of 4-methoxybenzaldehyde, 10 ml of methanol, 1.0 g (3.43 mmol, 1.0 equivalent) of 4-[(4-dipropylaminobutyl)amino]methylbenzylamine (5a), and 1.09 g (10.29 mmol, 3.0 equivalents) of trimethyl orthoformate were charged in a 100 ml recovery flask, and reacted at room temperature for 22 hours. After completion of the reaction, the solvent was concentrated, thereby obtaining 1.38 g of {(4-dipropylaminobutyl)-[4-(4-methoxybenzylidene)aminomethylbenzyl]}amine (22) as a slightly yellow oily substance (yield: 93%). [HPLC: 95% (HPLC measurement conditions C)]

Property Values of {(4-dipropylaminobutyl)-[4-(4-methoxybenzylidene)aminomethylbenzyl]}amine (22)

$^1$H-NMR (400 MHz, CDCl$_3$, ppm) δ: 8.32(s, 1H, HC=N), 7.72(m, 2H, J=8.8 Hz, MeO-Ph), 7.28(m, 4H, Ar—CH$_2$N=CH), 6.92(m, 2H, J=8.8 Hz, MeO-Ph), 4.77(s, 2H, Ar—CH$_2$N=CH), 3.84(s, 3H, MeO-Ph), 3.77(s, 2H, ArCH$_2$NH—), 2.63(dd, 2H, J=6.8, 6.9 Hz, ArCH$_2$NHCH$_2$CH$_2$), 2.42-2.33(m, 6H, NCH$_2$CH$_2$×3), 1.48-1.38 (m, 8H, NCH$_2$CH$_2$×4), 0.86(dd, 6H, J=7.3, 7.4 Hz, NCH$_2$CH$_2$CH$_3$×2) $^{13}$C-NMR (100 MHz, CDCl$_3$, ppm) δ: 161.22, 139.14, 138.18, 129.82, 128.26, 128.02, 113.98, 64.73, 56.24, 55.36, 54.13, 53.76, 49.34, 28.15, 24.91, 20.21, 11.98

EXAMPLE 26

Production of {(4-dipropylaminobutyl)-[4-(4-trifluoromethylbenzylidene)aminomethylbenzyl]}amine (23)

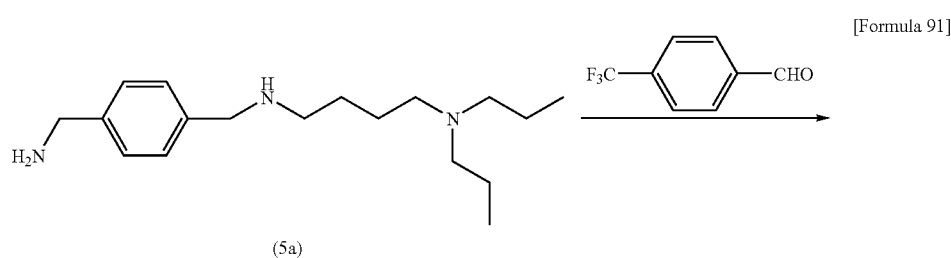

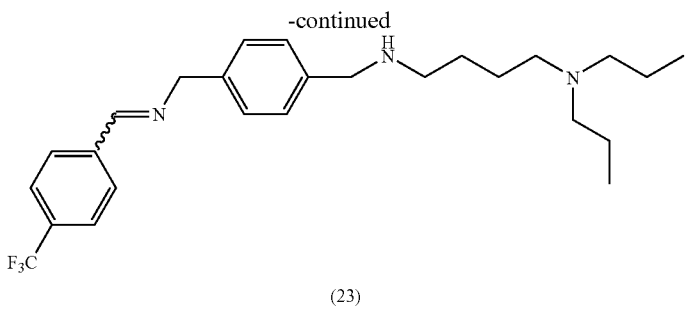

(23)

Under a nitrogen stream 549 mg (3.43 mmol, 1.0 equivalent) of 4-trifluoromethylbenzaldehyde, 10 ml of methanol, 1.0 g (3.43 mmol, 1.0 equivalent) of 4-[(4-dipropylaminobutyl)amino]methylbenzylamine (5a), and 1.09 g (10.29 mmol, 3.0 equivalents) of trimethyl orthoformate were charged in a 100 ml recovery flask, and reacted at room temperature for 22 hours. After completion of the reaction, the solvent was concentrated, thereby obtaining 1.51 g of {(4-dipropylaminobutyl)-[4-(4-trifluoromethylbenzylidene)aminomethylbenzyl]}amine (23) as a slightly yellow oily substance (yield: 98%). [HPLC: 93% (HPLC measurement conditions C)]

Property Values of {(4-dipropylaminobutyl)-[4-(4-trifluoromethylbenzylidene)aminomethylbenzyl]}amine (23)

$^1$H-NMR (400 MHz, CDCl$_3$, ppm) δ: 8.42(s, 1H, HC=N), 7.89(d, 2H, J=8.0 Hz, F$_3$C-Ph), 7.56(d, 2H, J=8.2 Hz, F$_3$C-Ph), 7.29(m, 4H, Ar—CH$_2$N=CH), 4.84(s, 2H, Ar—CH$_2$N=CH), 3.78(s, 2H, ArCH$_2$NH—), 2.63(dd, 2H, J=6.8,6.9 Hz, ArCH$_2$NHCH$_2$CH$_2$), 2.42-2.33(m, 6H, NCH$_2$CH$_2$×3), 1.48-1.40 (m, 8H, NCH$_2$CH$_2$×4), 0.86(dd, 6H, J=7.3, 7.4 Hz, NCH$_2$CH$_2$CH$_3$×2) $^{13}$C-NMR (100 MHz, CDCl$_3$, ppm) δ: 160.29, 128.45, 128.38, 128.08, 125.57, 125.54, 64.84, 56.23, 54.12, 53.73, 49.37, 28.14, 24.93, 20.19, 11.98

EXAMPLE 27

Production of {[4-(2,4-dichlorobenzylidene)aminomethylbenzyl]-(4-dipropylaminobutyl)}amine (24)

[Formula 92]

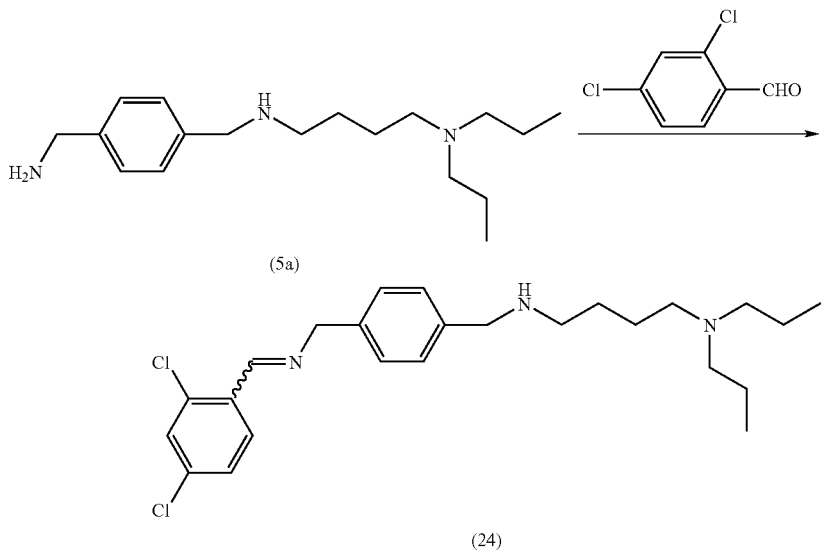

(24)

Under a nitrogen stream 600 mg (3.43 mmol, 1.0 equivalent) of 2,4-dichlorobenzaldehyde, 20 ml of methanol, 1.0 g (3.43 mmol, 1.0 equivalent) of 4-[(4-dipropylaminobutyl)amino]methylbenzylamine (5a), and 1.0 g of anhydrous sodium sulfate were charged in a 50 ml recovery flask, and reacted at room temperature for 23 hours. After completion of the reaction, the solvent was concentrated, thereby obtaining 1.49 g of {[4-(2,4-dichlorobenzylidene)aminomethylbenzyl]-(4-dipropylaminobutyl)}amine (24) as a slightly yellow oily substance (yield: 97%). [HPLC: 94% (HPLC measurement conditions B)]

Property Values of {[4-(2,4-dichlorobenzylidene) aminomethylbenzyl]-(4-dipropylaminobutyl)}amine (24)

$^1$H-NMR (400 MHz, CDCl$_3$, ppm) δ: 8.76(s, 1H, HC=N), 8.04(d, 1H, J=8.5 Hz, Cl$_2$-Ph), 7.40(d, 1H, J=2.0 Hz, Cl$_2$-Ph), 7.29(d, 1H, J=2.0 Hz, Cl$_2$-Ph), 7.28(m, 4H, Ar—CH$_2$N=CH), 4.83(s, 2H, Ar—CH$_2$N=CH), 3.78(s, 2H, ArCH$_2$NH—), 2.63(dd, 2H, J=6.78, 6.87 Hz, ArCH$_2$NHCH$_2$CH$_2$), 2.42-2.33(m, 6H, NCH$_2$CH$_2$×3), 1.49-1.40 (m, 8H, NCH$_2$CH$_2$×4), 0.86(dd, 6H, J=7.34, 7.38 Hz, NCH$_2$CH$_2$CH$_3$×2) $^{13}$C-NMR (100 MHz, CDCl$_3$, ppm) δ: 157.81, 139.88, 137.80, 132.18, 129.90, 129.82, 128.75, 128.44, 127.90, 65.46, 56.64, 54.52, 54.12, 49.75, 28.54, 25.33, 20.61, 12.37

EXAMPLE 28

Production of {(4-dipropylaminobutyl)-[4-(3-nitrobenzylidene)aminomethylbenzyl]}amine (25)

centrated, thereby obtaining 1.39 g of {(4-dipropylaminobutyl)-[4-(3-nitrobenzylidene)aminomethylbenzyl]}amine (25) as a yellow oily substance (yield: 96%). [HPLC: 89% (HPLC measurement conditions A)]

Property Values of {(4-dipropylaminobutyl)-[4-(3-nitrobenzylidene)aminomethylbenzyl]}amine (25)

$^1$H-NMR (400 MHz, CDCl$_3$, ppm) δ: 8.60(s, 1H, HC=N), 8.45(m, 1H, O$_2$N-Ph), 8.25(m, 1H, O$_2$N-Ph), 8.11(m, 1H, O$_2$N-Ph), 7.59(m, 1H, O$_2$N-Ph), 7.31(m, 4H, Ar—CH$_2$N=CH), 4.86(s, 2H, Ar—CH$_2$N=CH), 3.79(s, 2H, ArCH$_2$NH—), 2.64(m, 2H, ArCH$_2$NHCH$_2$CH$_2$), 2.39-2.32(m, 6H, NCH$_2$CH$_2$×3), 1.45-1.40(m, 8H, NCH$_2$CH$_2$×4),

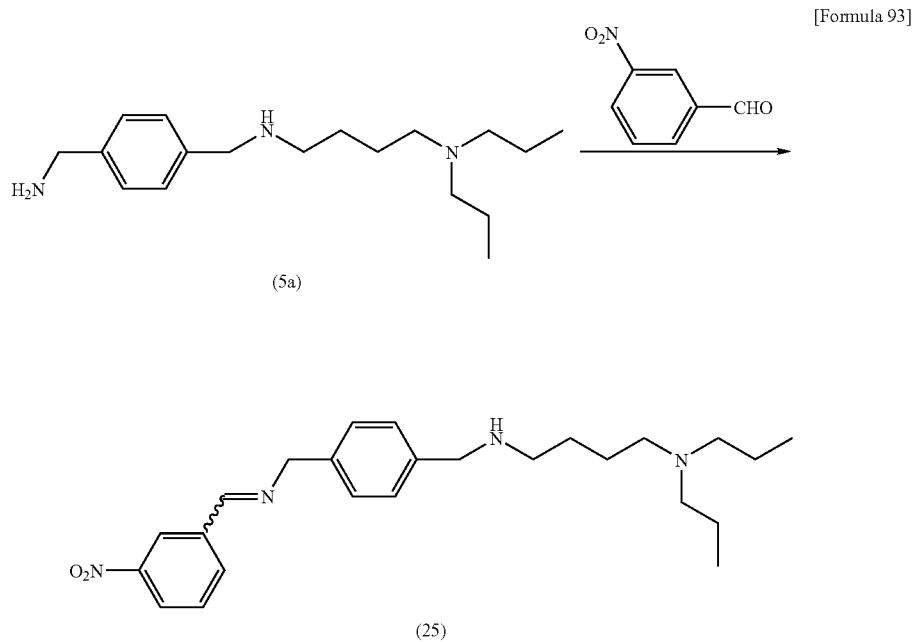

[Formula 93]

(5a)

(25)

Under a nitrogen stream 519 mg (3.43 mmol, 1.0 equivalent) of 3-nitrobenzaldehyde, 10 ml of methanol, 1.0 g (3.43 mmol, 1.0 equivalent) of 4-[(4-dipropylaminobutyl)amino]methylbenzylamine (5a), and 1.0 g of anhydrous sodium sulfate were charged in a 100 ml recovery flask and reacted at room temperature for 25 hours. The reaction solution was added with 50 ml of toluene and 20 ml of a saturated sodium hydrogen carbonate aqueous solution, and subjected to phase separation. After the organic layer was added with 20 ml of water, the solution was subjected to phase separation. The organic layer was dried over anhydrous sodium sulfate, con- 0.85(dd, 6H, J=7.42, 7.35 Hz, NCH$_2$CH$_2$CH$_3$×2) $^{13}$C-NMR (100 MHz, CDCl$_3$, ppm) δ: 159.04, 133.61, 129.59, 128.40, 128.14, 125.13, 123.10, 64.75, 56.28, 54.17, 53.73, 49.41, 28.17, 25.00, 20.27, 11.99

EXAMPLE 29

Production of {(4-dipropylaminobutyl)-[4-(5-methylfuran-2-ylmethylidene)aminomethylbenzyl]}amine (26)

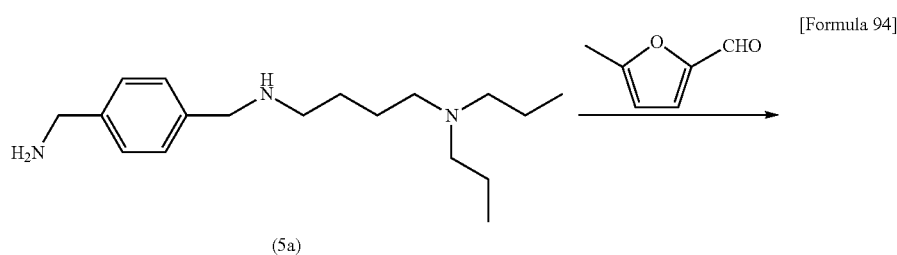

[Formula 94]

(5a)

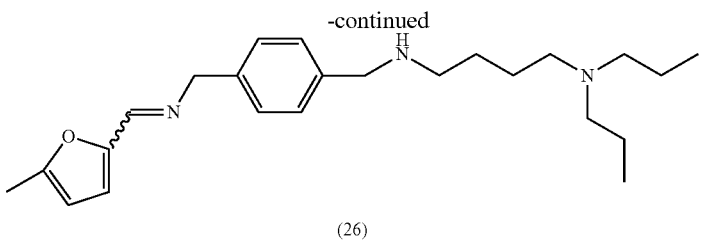

(26)

Under a nitrogen stream 415 mg (3.77 mmol, 1.1 equivalents) of 5-methyl-2-furaldehyde, 10 ml of ethanol, 1.0 g (3.43 mmol, 1.0 equivalent) of 4-[(4-dipropylaminobutyl)amino]methylbenzylamine (5a), and 3 g of anhydrous sodium sulfate were charged in a 50 ml recovery flask and reacted at 25° C. for 20 hours. After completion of the reaction, the reaction solution was filtered, and concentrated, thereby obtaining 1.32 g of {(4-dipropylaminobutyl)-[4-(5-methylfuran-2-ylmethylidene)aminomethylbenzyl]}amine (26) as a reddish brown oily substance (yield: 100%). [HPLC: 95.7% (HPLC measurement conditions C)]

Property Values of {(4-dipropylaminobutyl)-[4-(5-methylfuran-2-ylmethylidene)aminomethylbenzyl]} amine (26)

$^1$H-NMR (400 MHz, CDCl$_3$, ppm) δ: 8.04(s, 1H, HC=N), 7.28(d, 2H, J=8.72 Hz, Ar—CH$_2$N=CH), 7.26(d, 2H, J=8.72 Hz, Ar—CH$_2$N=CH), 6.63(d, 1H, J=3.27 Hz, furan-), 6.08 (d, 1H, J=3.28 Hz, furan-), 4.75(s, 2H, ArCH$_2$N=CH), 3.77 (s, 2H, ArCH$_2$NHCH$_2$), 2.62(dd, 2H, J=6.77, 6.88 Hz, ArCH$_2$NHCH$_2$CH$_2$), 2.43-2.31(m, 6H, NCH$_2$CH$_2$×3), 1.54-1.37(m, 8H, NCH$_2$CH$_2$×4), 0.86(dd, 6H, J=7.34, 7.38 Hz, NCH$_2$CH$_2$CH$_3$×2) $^{13}$C-NMR (100 MHz, CDCl$_3$, ppm) δ: 156.55, 150.54, 139.71, 137.95, 128.74, 128.67, 116.63, 108.42, 65.16, 56.64, 54.53, 54.14, 49.73, 28.55, 25.31, 20.62, 14.25, 12.37

EXAMPLE 30

Production of {(4-dipropylaminobutyl)-[4-(1H-imidazol-2-ylmethylidene)aminomethylbenzyl]}amine (27)

[Formula 95]

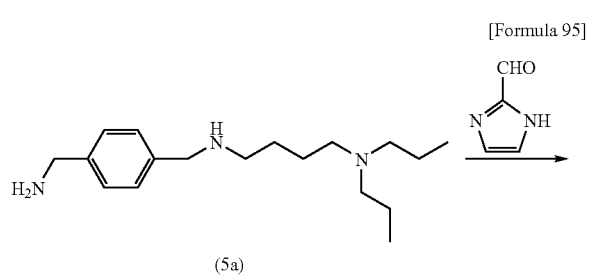

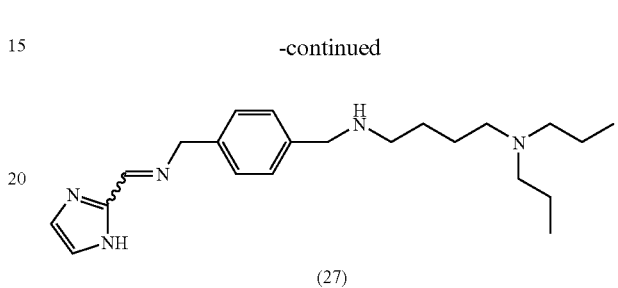

(27)

1.53 g (15.9 mmol, 1.16 equivalents) of 2-formylimidazole and 40 ml of methanol were charged in a 100 ml three-necked flask under a nitrogen stream. The mixture was then cooled to 0° C. After the addition of 4.0 g (13.7 mmol, 1.0 equivalent) of 4-[(4-dipropylaminobutyl)amino]methylbenzylamine (5a) and 7.28 g (68.6 mmol, 5.0 equivalents) of trimethyl orthoformate, the mixture was reacted at 25° C. for 48 hours. After completion of the reaction, the solvent was concentrated by about ⅔. The resulting solution was then cooled to 5° C., and the precipitated solid was removed by filtration. The obtained filtrate was concentrated, thereby obtaining 5.05 g of {(4-dipropylaminobutyl)-[4-(1H-imidazol-2-ylmethylidene)aminomethylbenzyl]}amine (27) as a reddish brown liquid (yield: 100%). [HPLC: 87.2% (HPLC measurement conditions C)]

Property Values of {(4-dipropylaminobutyl)-[4-(1H-imidazol-2-ylmethylidene)aminomethylbenzyl]} amine (27)

$^1$H-NMR (400 MHz, CDCl$_3$, ppm)δ: 8.32(s, 1H, HC=N), 7.28(d, 2H, J=6.7 Hz, Ar—CH$_2$N=CH), 7.23(d, 2H, J=6.9 Hz, Ar—CH$_2$N=CH), 7.05(bs, 2H, imidazole-), 4.76(s, 2H, ArCH$_2$N=CH), 3.77(s, 2H, ArCH$_2$NHCH$_2$), 2.62(dd, 2H, J=6.28, 6.77 Hz, ArCH$_2$NHCH$_2$CH$_2$), 2.41~2.29(m, 6H, NCH$_2$CH$_2$×3), 1.50~1.38(m, 8H, NCH$_2$CH$_2$×4), 0.86(dd, 6H, J=7.29, 7.41 Hz, NCH$_2$CH$_2$CH$_3$×2) $^{13}$C-NMR (100 MHz, CDCl$_3$, ppm) δ: 152.87, 140.10, 128.82, 128.57, 118.20, 64.62, 56.61, 54.50, 54.03, 49.70, 28.50, 25.28, 20.59, 12.37

EXAMPLE 31

Production of {(4-dipropylaminobutyl)-[4-(1-methylimidazol-2-ylmethylidene)aminomethylbenzyl]}amine (28) and {(4-dipropylaminobutyl)-[4-(1-methylimidazol-2-ylmethylidene)aminomethylbenzyl]amino}ethyl acetate (29)

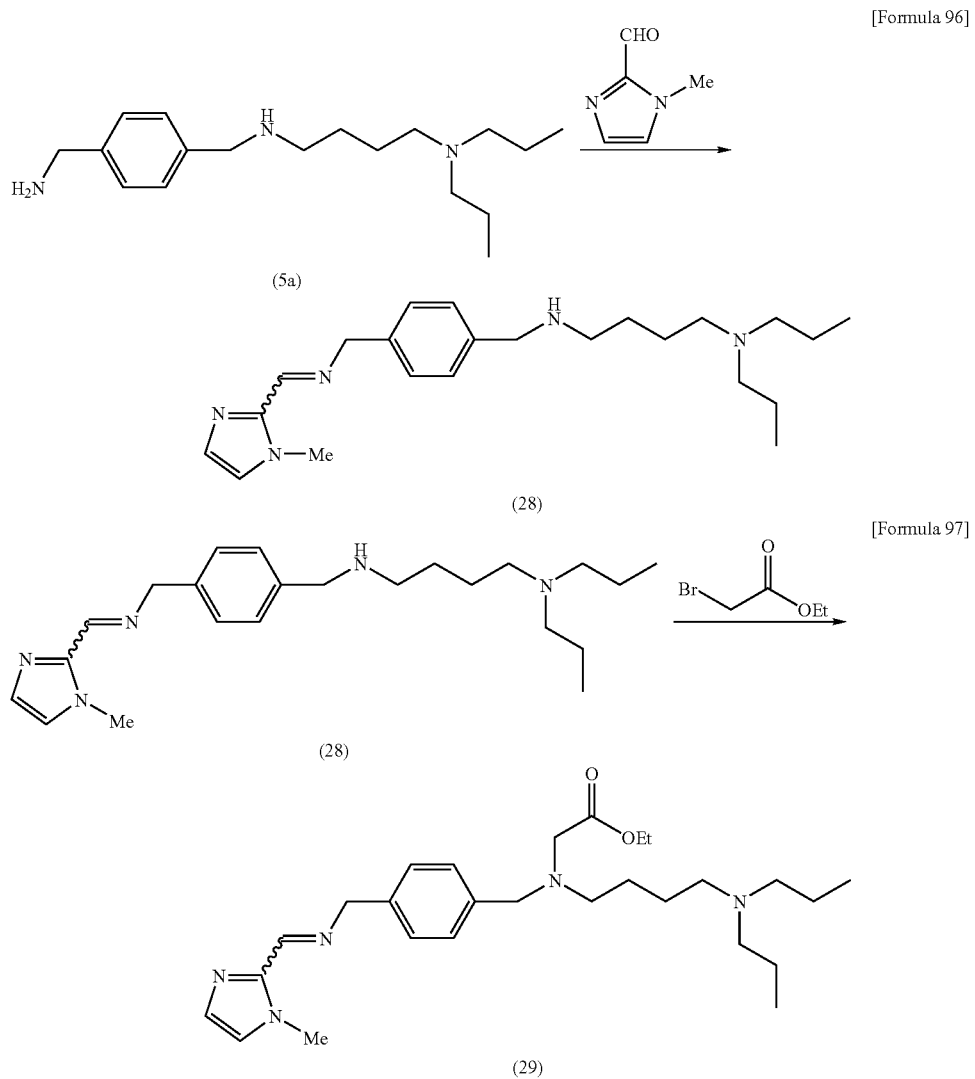

Under a nitrogen stream 340 mg (3.09 mmol, 1.0 equivalent) of 2-formyl-1-methylimidazole, 9 ml of tetrahydrofuran, 900 mg (3.09 mmol, 1.0 equivalent) of 4-[(4-dipropylaminobutyl)amino]methylbenzylamine (5a), and 984 mg (9.27 mmol, 3.0 equivalents) of trimethyl orthoformate were charged in a 50 ml recovery flask and reacted at 25° C. for three hours to generate {(4-dipropylaminobutyl)-[4-(1-methylimidazol-2-ylmethylidene)aminomethylbenzyl]}amine (28). A part of the reaction solution was concentrated and subjected to NMR measurement to identify the structure.

After confirming completion of the reaction by HPLC, 1.8 ml of tetrahydrofuran and 1.2 ml water were added to the reaction solution (tetrahydrofuran:water=9:1). After the addition of 619 mg (4.63 mmol, 1.5 equivalents) of potassium carbonate, the mixture was stirred. After the addition of 619 mg (3.71 mmol, 1.2 equivalents) of ethyl bromoacetate, the mixture was reacted at 25° C. for 6.2 hours.

The reaction solution was then placed in a beaker. After the addition of 20 ml of water, the reaction solution was added with 50 ml of toluene, and subjected to phase separation.

The reaction solution was extracted twice with 50 ml of toluene, washed with 20 ml of a saturated sodium bicarbonate aqueous solution, washed with 20 ml of water, dried over anhydrous sodium sulfate, and concentrated, thereby obtaining 1.25 g of {(4-dipropylaminobutyl)-[4-(1-methylimidazol-2-ylmethylidene)aminomethylbenzyl]amino}ethyl acetate (29) as a slightly yellow oily substance (yield: 87%). [HPLC: 90% (HPLC measurement conditions C)]

Property Values of {(4-dipropylaminobutyl)-[4-(1-methylimidazol-2-ylmethylidene)aminomethylbenzyl]}amine (28)

$^1$H-NMR (400 MHz, CDCl$_3$, ppm) δ: 8.42(s, 1H, HC=N), 7.28(m, 4H, Ar—), 7.12(s, 1H, Me-imidazole-), 6.93(s, 1H, Me-imidazole-), 4.77(s, 2H, ArCH$_2$N=CH), 4.01(s, 3H, Me-imidazole-), 3.77(s, 2H, ArCH$_2$NH), 2.64(dd, 2H, J=6.8, 6.9 Hz, ArCH$_2$NHCH$_2$CH$_2$), 2.42-2.32(m, 6H, NCH$_2$CH$_2$×3), 1.50-1.38(m, 8H, NCH$_2$CH$_2$×4), 0.86(dd, 6H, J=7.3, 7.4 Hz, NCH$_2$CH$_2$CH$_3$×2) $^{13}$C-NMR (100 MHz, CDCl$_3$, ppm) δ: 154.04, 139.41, 137.76, 129.28, 128.29, 127.89, 124.84, 65.19, 56.27, 54.16, 53.76, 49.42, 35.54, 28.16, 24.96, 20.25, 11.99

Property Values of {(4-dipropylaminobutyl)-[4-(1-methylimidazol-2-ylmethylidene)aminomethylbenzyl]amino}ethyl acetate (29)

$^1$H-NMR (400 MHz, CDCl$_3$, ppm) δ: 8.42(s, 1H, HC=N), 7.27(m, 4H, Ar—), 7.12(s, 1H, Me-imidazole-), 6.94(s, 1H, Me-imidazole-), 4.77(s, 2H, ArCH$_2$N=CH), 4.14(q, 2H, J=7.1 Hz, —COOCH$_2$CH$_3$), 4.02(s, 3H, Me-imidazole-), 3.76(s, 2H, ArCH$_2$NCH$_2$), 3.29(s, 2H, —NCH$_2$COOEt), 2.63 (dd, 2H, J=6.7, 7.1, ArCH$_2$NCH$_2$CH$_2$), 2.40~2.32(m, 6H, NCH$_2$CH$_2$×3), 1.47-1.40(m, 8H, NCH$_2$CH$_2$×4), 1.26(t, 3H, J=7.1, —COOCH$_2$CH$_3$), 0.86(dd, 6H, J=7.3, 7.4 Hz, NCH$_2$CH$_2$CH$_3$×2) $^{13}$C-NMR (100 MHz, CDCl$_3$, ppm) δ: 171.58, 154.04, 138.00, 137.90, 129.28, 129.07, 127.71, 124.84, 65.20, 60.15, 57.87, 56.23, 54.16, 54.07, 53.78, 35.46, 25.54, 24.71, 20.21, 14.30, 11.98

EXAMPLE 32

Production of {[4-(benzylidene)aminomethylbenzyl]-(4-dipropylaminobutyl)amino}ethyl acetate (8a)

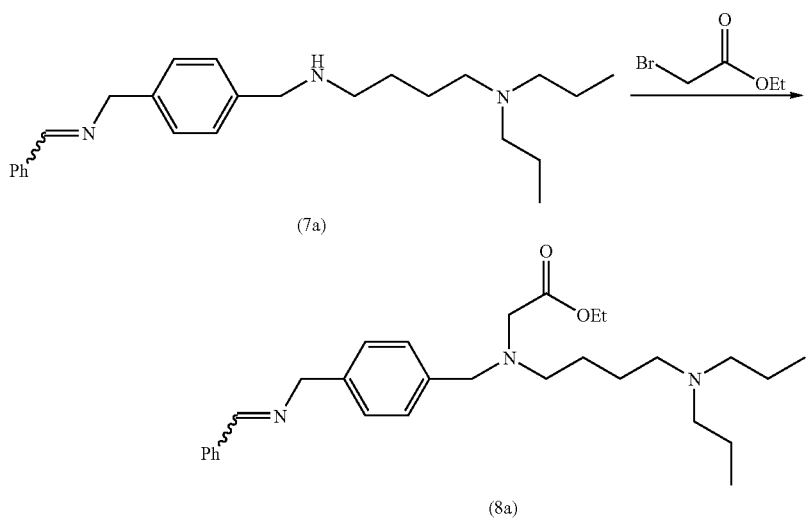

42.3 g (111 mmol, 1.0 equivalent) of {[4-(benzylidene)aminomethylbenzyl]-(4-dipropylaminobutyl)}amine (7a) was charged in a 1-liter four-necked flask and dissolved in 400 ml of tetrahydrofuran/water=9/1 under a nitrogen stream. After the addition of 46.2 g (334 mmol, 3.0 equivalents) of potassium carbonate at 20° C., the mixture was stirred for 20 minutes. The mixture was added dropwise with 22.2 g (133 mmol, 1.2 equivalents) of ethyl bromoacetate at 20° C., washed with 20 ml of tetrahydrofuran/water=9/1, 洗液を加えた and reacted at 20° C. for seven hours.

The reaction solution was concentrated. The concentrate was added with 400 ml of water, and extracted with 300 ml of toluene. The aqueous layer was re-extracted with 200 ml of toluene. The toluene layer was washed with 250 ml of a saturated sodium bicarbonate aqueous solution, washed with 300 ml of a saturated sodium chloride aqueous solution, dried over anhydrous sodium sulfate, filtered, and concentrated, thereby obtaining 43.0 g of {[4-(benzylidene)aminomethylbenzyl]-(4-dipropylaminobutyl)amino}ethyl acetate (8a) as a yellow oily substance (yield: 85%, GC: 94.1%). [HPLC: 80.5% (HPLC measurement conditions A)]

EXAMPLE 33

Production of {(4-dipropylaminobutyl)-[4-(4-methoxybenzylidene)aminomethylbenzyl]amino}ethyl acetate (30)

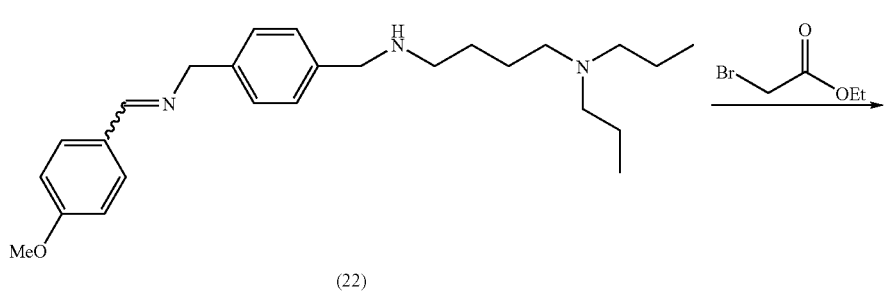

400 mg (0.98 mmol, 1.0 equivalent) of {(4-dipropylaminobutyl)-[4-(4-methoxybenzylidene)aminomethylbenzyl]}amine (22), 4 ml of tetrahydrofuran/water (=9/1), and 203 mg (1.47 mmol, 1.5 equivalents) of potassium carbonate were charged in a 100 ml recovery flask under a nitrogen stream, and stirred. After the addition of 196 mg (1.17 mmol, 1.2 equivalents) of ethyl bromoacetate, the mixture was reacted at room temperature for 5.5 hours.

The reaction solution was then placed in a beaker, added with 20 ml of water and 50 ml of toluene, and subjected to phase separation.

The reaction solution was extracted twice with 50 ml of chloroform, washed with 20 ml of a saturated sodium bicarbonate aqueous solution, washed with 20 ml of water, dried over anhydrous sodium sulfate, and concentrated, thereby obtaining 433.4 mg of {(4-dipropylaminobutyl)-[4-(4-methoxybenzylidene)aminomethylbenzyl]amino}ethyl acetate (30) as a slightly yellow oily substance (yield: 90%). [HPLC: 70% (HPLC measurement conditions A)]

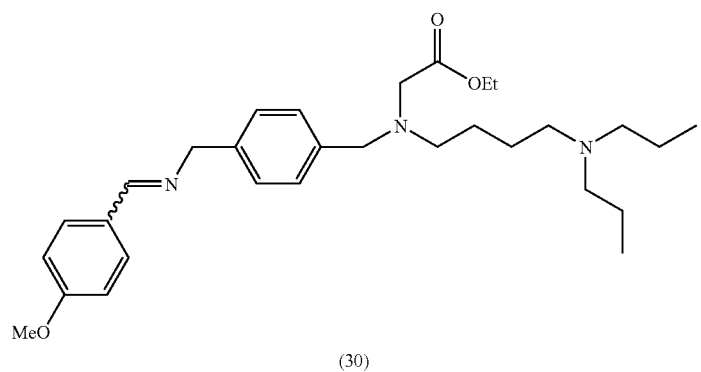

Property Values of {(4-dipropylaminobutyl)-[4-(4-methoxybenzylidene)aminomethylbenzyl]amino}ethyl acetate (30)

$^1$H-NMR (400 MHz, CDCl$_3$, ppm) δ: 8.32(s, 1H, HC=N), 7.72(d, 2H, J=8.8 Hz, MeO-Ph), 7.28(d, 4H, J=10.0 Hz, Ar—CH$_2$N=CH), 6.92(d, 2H, J=8.8 Hz, MeO-Ph), 4.77(s, 2H, Ar—CH$_2$N=CH), 4.14(q, 2H, J=7.1 Hz, —COOCH$_2$CH$_3$), 3.84(s, 3H, MeO-Ph), 3.76(s, 2H, ArCH$_2$NCH$_2$), 3.28(s, 2H, —NCH$_2$COOEt), 2.62(dd, 2H, J=6.8, 7.2 Hz, ArCH$_2$NCH$_2$CH$_2$), 2.36~2.32(m, 6H, NCH$_2$CH$_2$×3), 1.44-1.40(m, 8H, NCH$_2$CH$_2$×4), 1.25(t, 3H, J=7.1 Hz, —COOCH$_2$CH$_3$), 0.85(dd, 6H, J=7.3, 7.4 Hz, NCH$_2$CH$_2$CH$_3$×2)

$^{13}$C-NMR (100 MHz, CDCl$_3$, ppm) δ: 161.23, 138.27, 129.82, 129.07, 127.86, 113.98, 64.79, 60.13, 57.19, 56.22, 55.36, 54.15, 54.06. 53.75, 25.54, 14.30, 11.98

EXAMPLE 34

Production of 3-{(4-dipropylaminobutyl)-[4-(4-methoxybenzylidene)aminomethylbenzyl]amino}methyl propionate (31)

Property Values of 3-{(4-dipropylaminobutyl)-[4-(4-methoxybenzylidene)aminomethylbenzyl]amino}methyl propionate (31)

$^1$H-NMR (400 MHz, CDCl$_3$, ppm) δ: 8.32(s, 1H, HC=N), 7.72(d, 2H, J=8.8 Hz, MeO-Ph), 7.25(s, 4H,

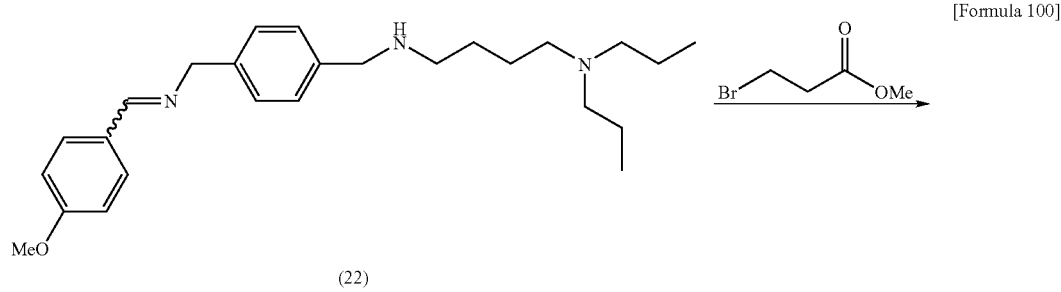

(22)

[Formula 100]

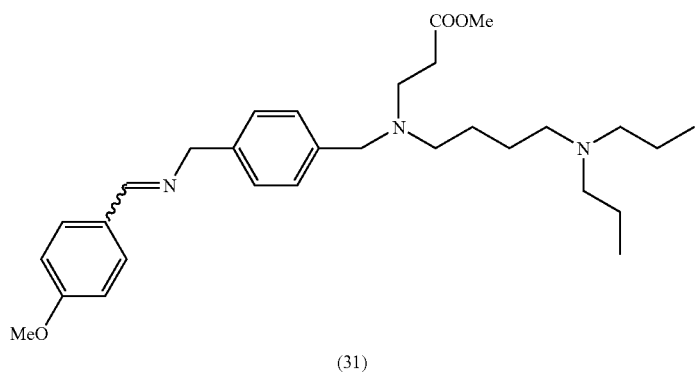

(31)

Under a nitrogen stream 400 mg (0.98 mmol, 1.0 equivalent) of {(4-dipropylaminobutyl)-[4-(4-methoxybenzylidene)aminomethylbenzyl]}amine (22), 4 ml of tetrahydrofuran/water (=9/1) and 155 mg (1.47 mmol, 1.5 equivalents) of sodium carbonate were charged in a 100 ml recovery flask, and stirred. The mixture was added with 202 mg (1.17 mmol, 1.2 equivalents) of methyl 3-bromopropionate, and reacted at room temperature for 140 hours.

The reaction solution was then placed in a beaker, added with 20 ml of water and 50 ml of toluene, and subjected to phase separation. The reaction solution was extracted twice with 50 ml of chloroform, washed with 20 ml of a saturated sodium bicarbonate aqueous solution, washed with 20 ml of water, dried over anhydrous sodium sulfate, and concentrated, thereby obtaining 419.5 mg of 3-{(4-dipropylaminobutyl)-[4-(4-methoxybenzylidene)aminomethylbenzyl]amino}methyl propionate (31) as a slightly yellow oily substance (yield: 87%). [HPLC: 76% (HPLC measurement conditions C)]

Ar—CH$_2$N=CH), 6.92(d, 2H, J=8.8 Hz, MeO-Ph), 4.77(s, 2H, Ar—CH$_2$N=CH), 3.84(s, 3H, MeO-Ph), 3.64(s, 3H, —COOMe), 3.54(s, 2H, ArCH$_2$NCH$_2$—) 2.78(dd, 2H, J=7.1, 7.4 Hz, —NCH$_2$CH$_2$COOMe), 2.46(dd, 2H, J=7.1, 7.4 Hz, —NCH$_2$CH$_2$COOMe), 2.41(dd, 2H, J=6.6, 7.2 Hz, ArCH$_2$NCH$_2$CH$_2$CH$_2$CH$_2$N), 2.34~2.31(m, 6H, NCH$_2$CH$_2$×3), 1.44-1.39 (m, 8H, NCH$_2$CH$_2$×4), 0.85(dd, 6H, J=7.3, 7.4 Hz, NCH$_2$CH$_2$CH$_3$×2)

$^{13}$C-NMR (100 MHz, CDCl$_3$, ppm) δ: 173.20, 161.18, 138.27, 138.08, 129.82, 129.21, 128.84, 127.78, 114.32, 113.97, 64.79, 58.14, 56.27, 55.35, 54.13, 53.52, 51.46, 49.24, 32.52, 25.03, 24.84, 20.28, 12.00

EXAMPLE 35

Production of {(4-dipropylaminobutyl)-[4-(4-trifluoromethylbenzylidene)aminomethylbenzyl]amino}benzyl acetate (32)

Property Values of {(4-dipropylaminobutyl)-[4-(4-trifluoromethylbenzylidene)aminomethylbenzyl]amino}benzyl acetate (32)

$^1$H-NMR (400 MHz, CDCl$_3$, ppm) δ: 8.42(s, 1H, HC=N), 7.88(d, 2H, J=8.0 Hz, F$_3$C-Ph), 7.66(d, 2H, J=8.2 Hz, F$_3$C-

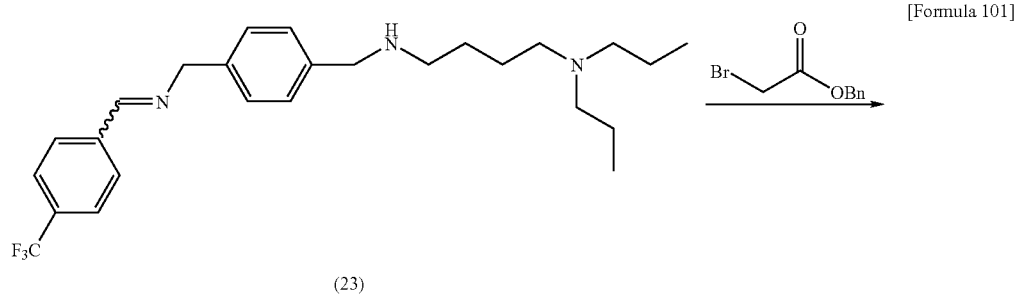

[Formula 101]

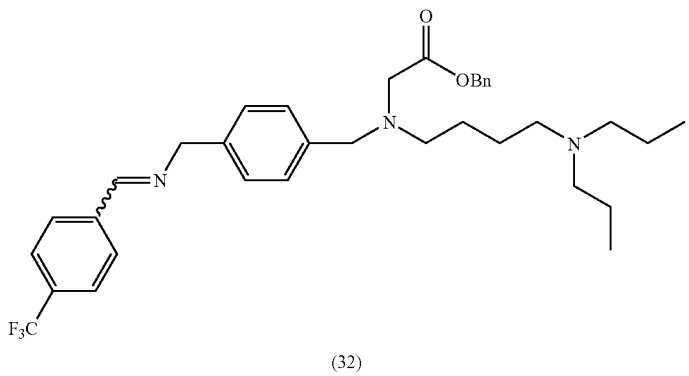

400 mg (0.89 mmol, 1.0 equivalent) of {(4-dipropylaminobutyl)-[4-(4-trifluoromethylbenzylidene)aminomethylbenzyl]}amine (23), 4 ml of N,N-dimethylformamide, and 185 mg (1.31 mmol, 1.5 equivalents) of potassium carbonate were charged in a 100 ml recovery flask under a nitrogen stream and stirred. The mixture was added with 205 mg (0.89 mmol, 1.2 equivalents) of benzyl bromoacetate, stirred at room temperature for 22 hours, and reacted at 60° C. for 78 hours. The reaction solution was then placed in a beaker, added with 20 ml of water and 50 ml of toluene, and subjected to phase separation. The reaction solution was extracted twice with 50 ml of chloroform, washed with 20 ml of a saturated sodium bicarbonate aqueous solution, washed with 20 ml of water, dried over anhydrous sodium sulfate, and concentrated, thereby obtaining 517.5 mg of {(4-dipropylaminobutyl)-[4-(4-trifluoromethylbenzylidene)aminomethylbenzyl]amino}benzyl acetate (32) as a slightly yellow oily substance (yield: 97%). [HPLC: 73% (HPLC measurement conditions B)]

Ph), 7.36(d, 2H, J=11.2 Hz, —COOCH$_2$Ph), 7.34(m, 4H, Ar—CH$_2$N=CH), 7.30(d, 3H, J=4.0 Hz, —COOCH$_2$Ph), 5.12(s, 2H, —COOCH$_2$Ph), 4.83(s, 2H, Ar—CH$_2$N=CH), 3.77(s, 2H, ArCH$_2$NCH$_2$), 3.35(s, 2H, —NCH$_2$COOBn), 2.64(t, 2H, J=7.2 Hz, ArCH$_2$NCH$_2$CH$_2$), 2.32(m, 6H, NCH$_2$CH$_2$×3), 1.44-1.39(m, 8H, —NCH$_2$CH$_2$×4), 0.85(dd, 6H, J=7.3, 7.4 Hz, —NCH$_2$CH$_2$CH$_3$×2)

$^{13}$C-NMR (100 MHz, CDCl$_3$, ppm) δ: 129.16, 128.54, 128.46, 128.22, 127.92, 65.98, 64.89, 56.24, 54.07, 20.23, 11.99

EXAMPLE 36

Production of {[4-(2,4-dichlorobenzylidene)aminomethylbenzyl]-(4-dipropylaminobutyl)}amino}ethyl acetate (33)

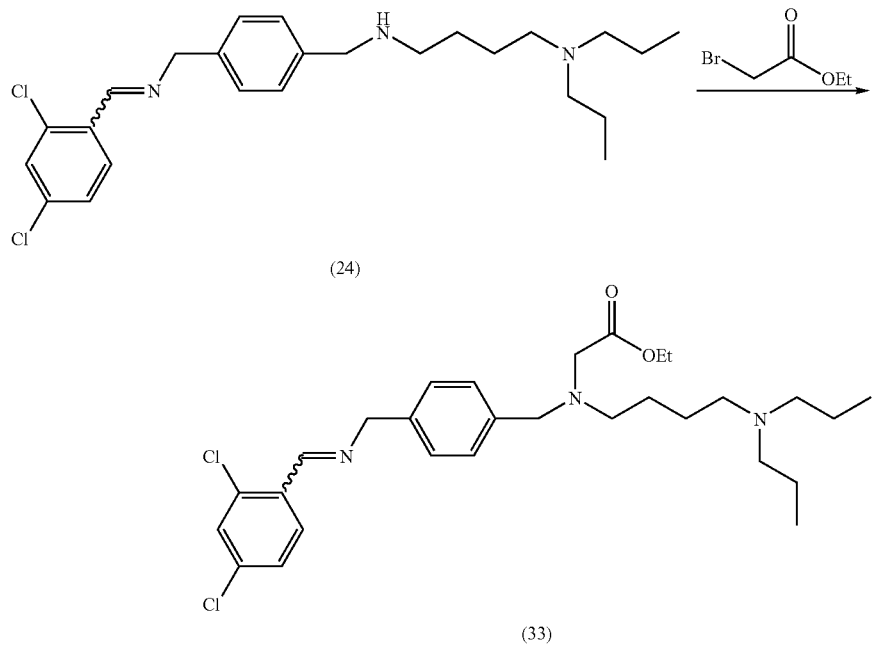

400 mg (0.89 mmol, 1.0 equivalent) of {[4-(2,4-dichlorobenzylidene)aminomethylbenzyl]-(4-dipropylaminobutyl)}amine (24), 4 ml of cyclopentyl methyl ether, and 253 mg (1.78 mmol, 2.0 equivalents) of N,N-diisopropylethylamine were charged in a 100 ml recovery flask under a nitrogen stream and stirred. The mixture was added with 184 mg (1.07 mmol, 1.2 equivalents) of ethyl bromoacetate, and reacted at room temperature for 25 hours. The reaction solution was then placed in a beaker, added with 20 ml of water and 50 ml of toluene, and subjected to phase separation. The reaction solution was extracted twice with 50 ml of chloroform, washed with 20 ml of a saturated sodium bicarbonate aqueous solution, washed with 20 ml of water, dried over anhydrous sodium sulfate, and concentrated, thereby obtaining 441.2 mg of {[4-(2,4-dichlorobenzylidene)aminomethylbenzyl]-(4-dipropylaminobutyl)}amino}ethyl acetate (33) as a slightly yellow oily substance (yield: 93%). [HPLC: 86% (HPLC measurement conditions B)]

Property Values of {[4-(2,4-dichlorobenzylidene)aminomethylbenzyl]-(4-dipropylaminobutyl)}amino}ethyl acetate (33)

$^1$H-NMR (400 MHz, CDCl$_3$, ppm) δ: 8.76(s, 1H, HC=N), 8.04(d, 2H, J=8.4 Hz, Cl$_2$-Ph), 7.40(s, 1H, Cl$_2$-Ph), 7.30(m, 4H, Ar—CH$_2$N=CH), 4.83(s, 2H, Ar—CH$_2$N=CH), 4.14 (q, 2H, J=7.1 Hz, —COOCH$_2$CH$_3$), 3.76(s, 2H, ArCH$_2$NCH$_2$), 3.28(s, 2H, —NCH$_2$COOEt), 2.62(dd, 2H, J=6.9, 7.0 Hz, ArCH$_2$NCH$_2$CH$_2$), 2.35(m, 6H, —NCH$_2$CH$_2$×3), 1.46-1.43 (m, 8H, —NCH$_2$CH$_2$×4), 1.26(t, 3H, J=7.1 Hz, —COOCH$_2$CH$_3$) 0.86(dd, 6H, J=7.3, 7.4 Hz, —NCH$_2$CH$_2$CH$_3$×2)

$^{13}$C-NMR (100 MHz, CDCl$_3$, ppm) δ: 157.45, 129.52, 129.44, 129.16, 127.91, 127.51, 65.10, 60.16, 57.90, 56.18, 54.16, 53.73, 25.52, 14.30, 11.96

EXAMPLE 37

Production of {(4-dipropylaminobutyl)-[4-(3-nitrobenzylidene)aminomethylbenzyl]amino}ethyl acetate (34)

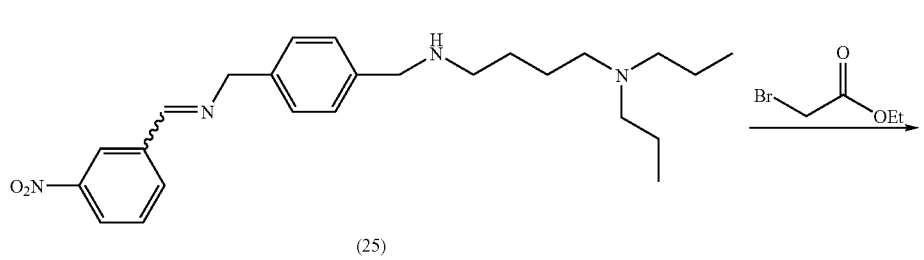

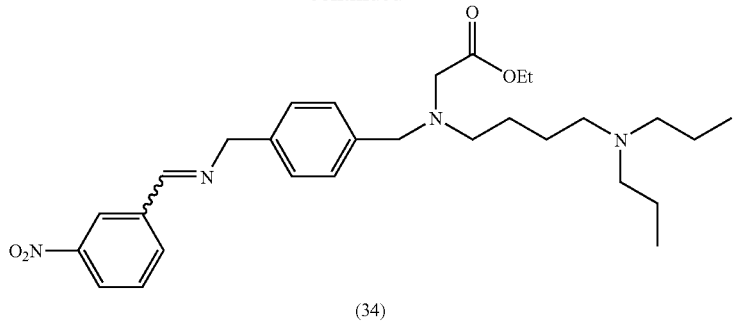

(34)

400 mg (0.94 mmol, 1.0 equivalent) of {(4-dipropylaminobutyl)-[4-(3-nitrobenzylidene)aminomethylbenzyl]}amine (25), 4 ml of tetrahydrofuran/water (=9/1), and 195 mg (1.41 mmol, 1.5 equivalents) of potassium carbonate were charged in a 100 ml recovery flask under a nitrogen stream and stirred. The mixture was added with 195 mg (1.13 mmol, 1.2 equivalents) of ethyl bromoacetate, and reacted at room temperature for 72 hours.

The reaction solution was then placed in a beaker, added with 20 ml of water and 50 ml of toluene, and subjected to phase separation. The reaction solution was extracted twice with 50 ml of chloroform, washed with 20 ml of a saturated sodium bicarbonate aqueous solution, washed with 20 ml of water, dried over anhydrous sodium sulfate, and concentrated, thereby obtaining 326.4 mg of {(4-dipropylaminobutyl)-[4-(3-nitrobenzylidene)aminomethylbenzyl]amino}ethyl acetate (34) as a yellow oily substance (yield: 68%). [HPLC: 67% (HPLC measurement conditions A)]

Property Values of {(4-dipropylaminobutyl)-[4-(3-nitrobenzylidene)aminomethylbenzyl]amino}ethyl acetate (34)

$^1$H-NMR (400 MHz, CDCl$_3$, ppm) δ: 8.60(s, 1H, HC=N), 8.45(s, 1H, O$_2$N-Ph), 8.28(m, 1H, O$_2$N-Ph), 8.13(d, 1H, J=7.8 Hz, O$_2$N-Ph), 7.59(m, 1H, O$_2$N-Ph), 7.30(m, 4H, Ar—CH$_2$N=CH), 4.85(s, 2H, Ar—CH$_2$N=CH), 4.14(q, 2H, J=7.1 Hz, —COOCH$_2$CH$_3$), 3.78(s, 2H, ArCH$_2$NCH$_2$), 3.29(s, 2H, —NCH$_2$COOEt) 2.63(dd, 2H, J=6.8, 7.2 Hz, ArCH$_2$NCH$_2$CH$_2$), 2.39-2.31(m, 6H, —NCH$_2$CH$_2$×3), 1.47-1.39 (m, 8H, —NCH$_2$CH$_2$×4), 1.26(t, 3H, J=7.1 Hz, —COOCH$_2$CH$_3$), 0.85(dd, 6H, J=7.3, 7.4 Hz, —NCH$_2$CH$_2$CH$_3$×2)

$^{13}$C-NMR (100 MHz, CDCl$_3$, ppm) δ: 159.06, 138.34, 133.62, 129.59, 129.19, 127.98, 125.13, 123.11, 64.81, 60.15, 57.88, 56.26, 54.16, 54.10, 53.79, 25.55, 20.27, 14.30, 11.98

EXAMPLE 38

Production of {(4-dipropylaminobutyl)-n-hexyl-[4-(5-methylfuran-2-ylmethylidene)aminomethylbenzyl]}amine (35)

[Formula 104]

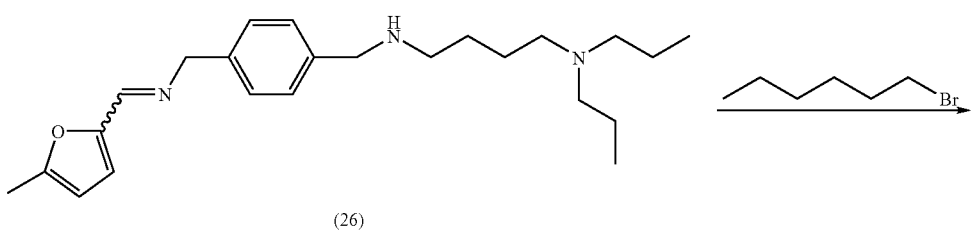

(26)

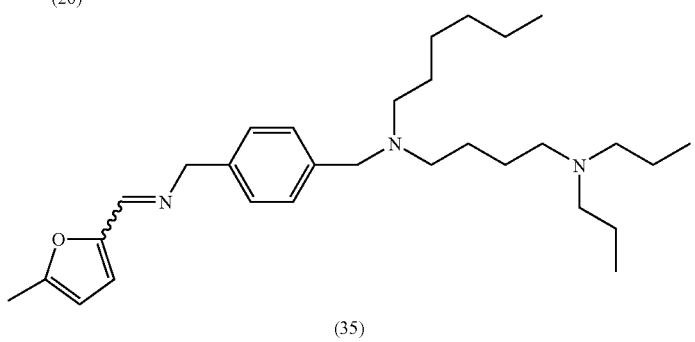

(35)

Under a nitrogen stream 488 mg (1.27 mmol, 1.0 equivalent) of {(4-dipropylaminobutyl)-[4-(5-methylfuran-2-ylmethylidene)aminomethylbenzyl]}amine (26), 8 ml of N-methyl-2-pyrrolidinone, 193 mg (1.91 mmol, 1.5 equivalents) of diisopropylamine, and 252 mg (1.53 mmol, 1.2 equivalents) of 1-hexyl bromide were charged in a 50 ml recovery flask and reacted at 26° C. for six days. The reaction solution was added with 30 ml of water, and extracted with 50 ml of toluene. The organic layer was washed three times with 20 ml of a saturated sodium bicarbonate aqueous solution, washed with 20 ml of water, dried over anhydrous sodium sulfate, and concentrated, thereby obtaining 443 mg of {(4-dipropylaminobutyl)-n-hexyl-[4-(5-methylfuran-2-ylmethylidene)aminomethylbenzyl]}amine (35) as a reddish brown oily substance (yield: 85%).

Property Values of {(4-dipropylaminobutyl)-n-hexyl-[4-(5-methylfuran-2-ylmethylidene)aminomethylbenzyl]}amine (35)

$^1$H-NMR (400 MHz, CDCl$_3$, ppm) δ: 8.05(d, 1H, J=1.30 Hz, HC=N), 7.28(d, 2H, J=8.03 Hz, Ar—CH$_2$N=CH), 7.23 (d, 2H, J=8.16 Hz, Ar—CH$_2$N=CH), 6.64(d, 1H, J=3.28 Hz, furan-), 6.07(dd, 1H, J=2.35, 0.93 Hz, furan-), 4.74(s, 2H, Ar—CH$_2$N=CH), 3.52(s, 2H, ArCH$_2$NCH$_2$—), 2.43-2.30 (m, 10H, NCH$_2$CH$_2$×5), 2.36(s, 3H, Me-furan-), 1.49-1.36 (m, 10H, NCH$_2$CH$_2$×5), 1.34-1.20(m, 6H, —CH$_2$—×3), 0.87 (t, 3H, J=7.05 Hz, N—(CH$_2$)$_5$—CH$_3$), 0.86(dd, 6H, J=7.34, 7.37 Hz, NCH$_2$CH$_2$CH$_3$×2)

$^{13}$C-NMR (100 MHz, CDCl$_3$, ppm) δ: 150.10, 139.04, 137.70, 128.95, 128.05, 116.17, 108.02, 64.87, 58.33, 56.27, 54.19, 53.81, 53.72, 31.83, 27.15, 27.02, 25.07, 24.89, 22.67, 20.25, 14.06, 13.86, 12.00

EXAMPLE 39

Production of 3-{[4-(benzylidene)aminomethylbenzyl]-(4-dipropylaminobutyl)amino}methyl propionate (36)

400 mg (1.05 mmol, 1.0 equivalent) of {[4-(benzylidene)aminomethylbenzyl]-(4-dipropylaminobutyl)}amine (7a), 4 ml of methanol, 109 mg (1.27 mmol, 1.2 equivalents) of methyl acrylate, and 42 mg (0.21 mmol, 0.2 equivalents) of a 28% sodium methoxide/methanol solution were charged in a 50 ml recovery flask under a nitrogen stream and reacted at 25° C. for 54 hours. The reactant was added with 45 mg (0.53 mmol, 0.5 equivalents) of methyl acrylate, and the mixture was reacted for 20 hours. Furthermore, the reactant was added with 45 mg (0.53 mmol, 0.5 equivalents) of methyl acrylate, and the mixture was reacted for 24 hours. The reaction solution was added with 30 ml of water, extracted twice with 50 ml of chloroform. The chloroform layer was washed twice with 20 ml of a saturated sodium bicarbonate aqueous solution, washed with 20 ml of water, dried over anhydrous sodium sulfate, and concentrated, thereby obtaining 396 mg of 3-{[4-(benzylidene)aminomethylbenzyl]-(4-dipropylaminobutyl)amino}methyl propionate (36) as a slightly yellow oily substance (yield: 81%). [HPLC: 73.6% (HPLC measurement conditions A)]

Property Values of 3-{[4-(benzylidene)aminomethylbenzyl]-(4-dipropylaminobutyl)amino}methyl propionate (36)

$^1$H-NMR (400 MHz, CDCl$_3$, ppm) δ: 8.39(s, 1H, HC=N), 7.80-7.77(m, 2H, Ph-), 7.43-7.38(m, 3H, Ph-), 7.27(s, 4H, Ar—CH$_2$N=CH), 4.81(d, 2H, J=1.28 Hz, Ar—CH$_2$N=CH), 3.64(s, 3H, —COOMe), 3.55(s, 2H, ArCH$_2$N—), 2.78(dd, 2H, J=7.09,7.42 Hz, —NCH$_2$CH$_2$COOMe), 2.46(dd, 2H, J=7.39, 7.11 Hz, —CH$_2$COOMe), 2.42(dd, 2H, J=6.73, 7.18 Hz, ArCH$_2$NCH$_2$CH$_2$CH$_2$N), 2.38-2.30(m, 6H, NCH$_2$× 3), 1.47-1.36 (m, 8H, NCH$_2$CH$_2$×4), 0.85(dd, 6H, J=7.33, 7.39 Hz, NCH$_2$CH$_2$CH$_3$×2)

$^{13}$C-NMR (100 MHz, CDCl$_3$, ppm) δ: 173.30, 161.87, 138.37, 137.79, 130.71, 128.87, 128.58, 128.27, 127.81, 64.87, 58.14, 56.24, 54.10, 53.52, 51.46, 49.26, 32.52, 25.02, 24.79, 20.24, 11.99

[Formula 105]

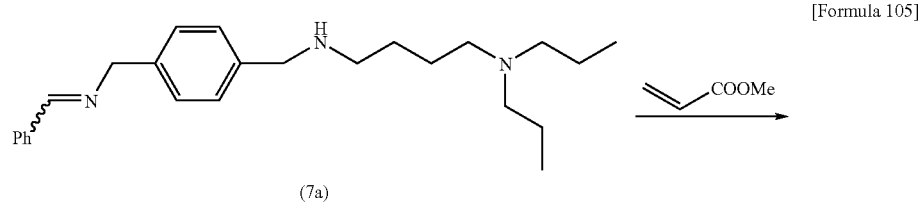

(7a)

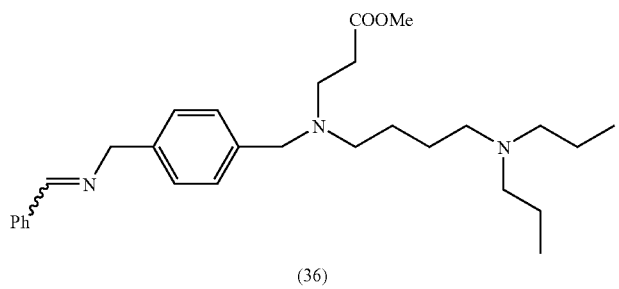

(36)

EXAMPLE 40

Production of 3-{(4-dipropylaminobutyl)-[4-(4-methoxybenzylidene)aminomethylbenzyl]amino}methyl propionate (31)

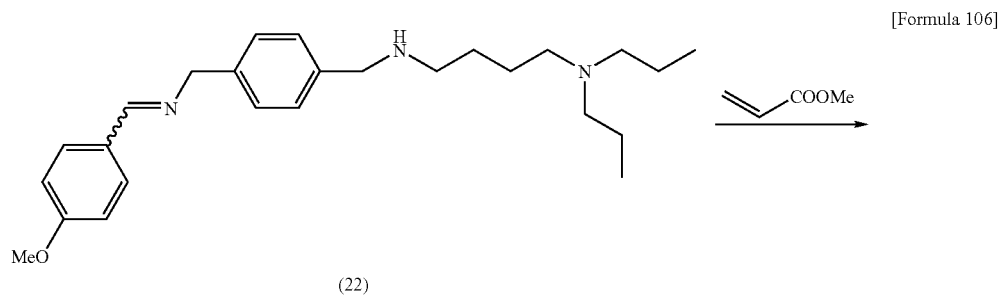

(22)

[Formula 106]

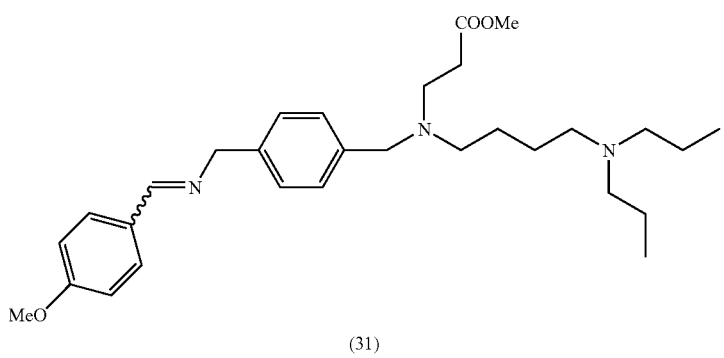

(31)

Under a nitrogen stream 508 mg (1.24 mmol, 1.0 equivalent) of {(4-dipropylaminobutyl)-[4-(4-methoxybenzylidene)aminomethylbenzyl]}amine (22), 6 ml of methanol, and 160 mg (1.86 mmol, 1.5 equivalents) of methyl acrylate were charged in a 50 ml recovery flask and reacted at 26° C. for 21 hours. The reaction solution was concentrated, thereby obtaining 604 mg of 3-{(4-dipropylaminobutyl)-[4-(4-methoxybenzylidene)aminomethylbenzyl]amino}methyl propionate (31) as a slightly yellow oily substance (yield: 98%). [HPLC: 79.1% (HPLC measurement conditions A)]

EXAMPLE 41

Production of {(4-dipropylaminobutyl)-[4-(1H-imidazol-2-ylmethylidene)aminomethylbenzyl]amino}ethyl acetate (37)

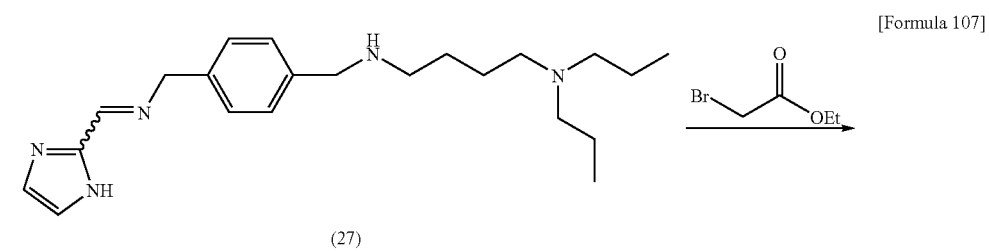

(27)

[Formula 107]

-continued

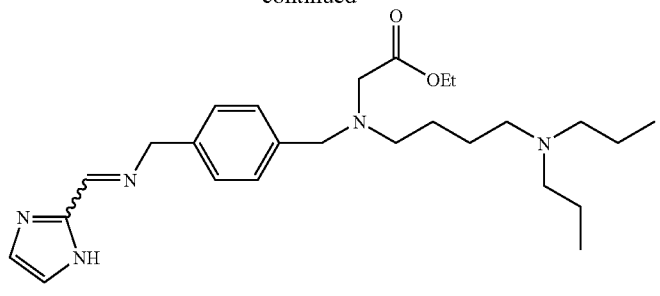

(37)

Under a nitrogen stream 1.05 g (2.85 mmol, 1.0 equivalent) of {(4-dipropylaminobutyl)-[4-(1H-imidazol-2-ylmethylidene)aminomethylbenzyl]}amine (27), 10 ml of tetrahydrofuran/water (=9/1), 590 mg (4.27 mmol, 1.5 equivalents) of potassium carbonate, and 588 mg (3.42 mmol, 1.2 equivalents) of ethyl bromoacetate were charged in a 100 ml recovery flask and reacted at 22° C. for five hours.

After completion of the reaction, the reaction solution was placed into 30 ml of water, added with 100 ml of toluene, and subjected to phase separation. The reaction solution was washed with 30 ml of a saturated sodium bicarbonate aqueous solution and 30 ml of water, dried over anhydrous sodium sulfate, filtered, and concentrated, thereby obtaining 1.15 g of {(4-dipropylaminobutyl)-[4-(1H-imidazol-2-ylmethylidene)aminomethylbenzyl]amino}ethyl acetate (37) as a yellow oily substance (yield: 89%). [HPLC: 84.2% (HPLC measurement conditions C)]

Property Values of {(4-dipropylaminobutyl)-[4-(1H-imidazol-2-ylmethylidene)aminomethylbenzyl]amino}ethyl acetate (37)

$^1$H-NMR (400 MHz, CDCl$_3$, ppm) δ: 8.32(s, 1H, HC=N), 7.32(d, 2H, J=7.99 Hz, Ar—), 7.23(d, 2H, J=8.03 Hz, Ar—), 7.05(bs, 2H, imidazole-), 4.76(s, 2H, ArCH$_2$N=CH), 4.15(q, 2H, J=7.14 Hz, —COOCH$_2$CH$_3$), 3.76(s, 2H, ArCH$_2$NCH$_2$), 3.29(s, 2H, —NCH$_2$COOEt), 2.62(t, 2H, J=6.83 Hz, ArCH$_2$NCH$_2$CH$_2$), 2.43~2.30(m, 6H, NCH$_2$CH$_2$×3), 1.50~1.36(m, 8H, NCH$_2$CH$_2$×4), 1.26(t, 3H, J=7.12 Hz,—COOCH$_2$CH$_3$), 0.86(dd, 6H, J=7.33, 7.38 Hz, NCH$_2$CH$_2$CH$_3$×2)

$^{13}$C-NMR (100 MHz, CDCl$_3$, ppm) δ: 171.55, 152.50, 138.50, 137.01, 130.71, 129.26, 129.00, 128.07, 118.04, 64.28, 60.17, 57.94, 56.25, 54.23, 54.09, 53.66, 25.55, 24.55, 20.21, 14.30, 11.99

EXAMPLE 42

Production of {(4-dipropylaminobutyl)-[4-(1H-imidazol-2-ylmethylidene)aminomethylbenzyl]amino}ethyl acetate (37)

[Formula 108]

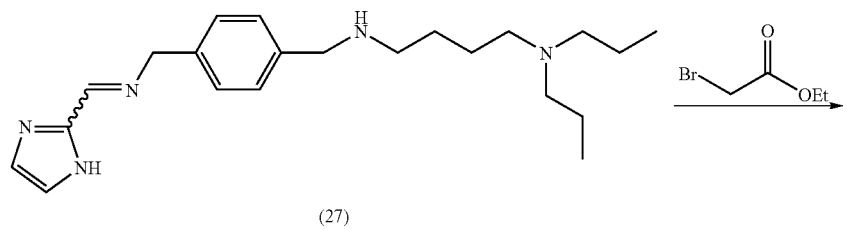

(27)

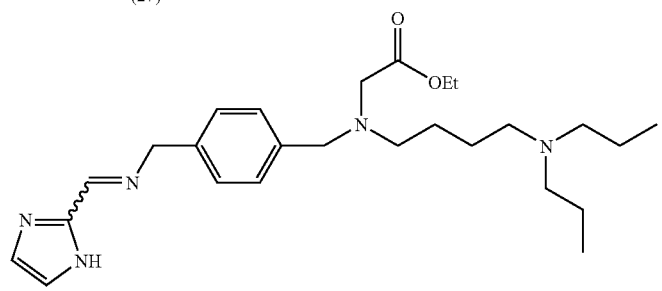

(37)

2.2 ml of water and 741 mg (8.82 mmol, 1.5 equivalents) of sodium hydrogen carbonate were charged in a 100 ml three-necked flask under a nitrogen stream and stirred. The mixture was added with a solution prepared by dissolving 2.17 g (5.88 mmol, 1.0 equivalent) of {(4-dipropylaminobutyl)-[4-(1H-imidazol-2-ylmethylidene)aminomethylbenzyl]}amine (27) in 19.8 ml of tetrahydrofuran. Ethyl bromoacetate was then separately added to the mixture as follows. After the addition of 202 mg (1.17 mmol, 0.2 equivalents) of ethyl bromoacetate at 25° C., the mixture was reacted at 25° C. for 1.5 hours. After the addition of a further 202 mg (0.2 equivalents) of ethyl bromoacetate, the mixture was reacted at 25° C. for 1.5 hours. After the addition of a further 202 mg (0.2 equivalents) of ethyl bromoacetate, the mixture was reacted at 25° C. for 1.5 hours. After the addition of a further 202 mg (0.2 equivalents) of ethyl bromoacetate, the mixture was reacted at 25° C. for one hour. After the addition of a further 202 mg (0.2 equivalents) of ethyl bromoacetate, the mixture was reacted at 25° C. for one hour. After the addition of a further 202 mg (0.2 equivalents) of ethyl bromoacetate, the mixture was reacted at 25° C. for 20 hours.

After completion of the reaction, the reaction solution was placed in 30 ml of water, added with 50 ml of toluene and subjected to phase separation. The reaction solution was washed with 20 ml of a saturated sodium bicarbonate aqueous solution, washed with 20 ml of water, dried over anhydrous sodium sulfate, filtered, and concentrated, thereby obtaining 2.11 g of {(4-dipropylaminobutyl)-[4-(1H-imidazol-2-ylmethylidene)aminomethylbenzyl]amino}ethyl acetate (37) as a yellow oily substance (yield: 79%). [HPLC: 76.3% (HPLC measurement conditions C)]

EXAMPLE 43

Production of {(4-dipropylaminobutyl)-[4-(1H-imidazol-2-ylmethylidene)aminomethylbenzyl]amino}ethyl acetate (37)

1.14 g (3.09 mmol, 1.0 equivalent) of {(4-dipropylaminobutyl)-[4-(1H-imidazol-2-ylmethylidene)aminomethylbenzyl]}amine (27), 11 ml of cyclopentyl methyl ether, 11 ml of water, 640 mg (4.63 mmol, 1.5 equivalents) of potassium carbonate, 100 mg (0.31 mmol, 0.1 equivalents) of tetra-n-butylammonium bromide, and 638 mg (3.71 mmol, 1.2 equivalents) of ethyl bromoacetate were charged in a 100 ml recovery flask under a nitrogen stream and reacted at 26° C. Potassium carbonate and ethyl bromoacetate were divisionally added to the reaction solution as follows. After 24 hours from the initiation of the reaction, 427 mg (1.0 equivalent) of potassium carbonate and 266 mg (0.5 equivalents) of ethyl bromoacetate were added to the solution and stirred. After further 24 hours, 427 mg (1.0 equivalent) of potassium carbonate and 266 mg (0.5 equivalents) of ethyl bromoacetate were added to the solution and stirred. Furthermore, after three days, 213 mg (0.5 equivalents) of potassium carbonate and 160 mg (0.3 equivalents) of ethyl bromoacetate were added to the solution and stirred for 22 hours.

After completion of the reaction, the reaction solution was placed in 30 ml of a saturated sodium bicarbonate aqueous solution. The mixture was added with 50 ml of toluene and subjected to phase separation. The reaction solution was re-extracted with 50 ml of toluene. The toluene layer was washed with 20 ml of a saturated sodium bicarbonate aqueous solution and 20 ml of water, dried over anhydrous sodium sulfate, filtered, and concentrated, thereby obtaining 1.01 g of {(4-dipropylaminobutyl)-[4-(1H-imidazol-2-ylmethylidene)aminomethylbenzyl]amino}ethyl acetate (37) as a yellow oily substance (yield: 72%). [HPLC: 74.2% (HPLC measurement conditions C)]

[Formula 109]

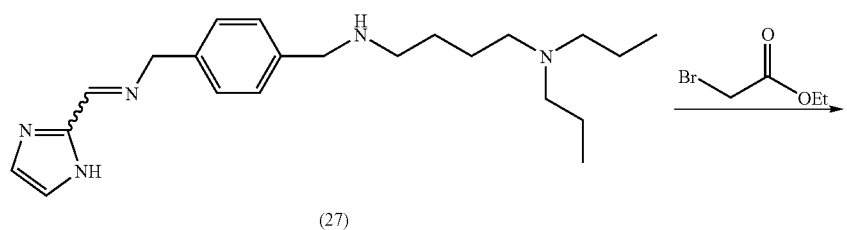

(27)

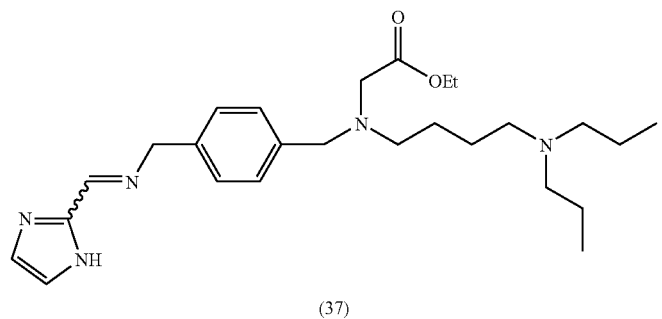

(37)

EXAMPLE 44

Production of {[4-(benzylidene)aminomethylbenzyl]-(4-dipropylaminobutyl)amino}ethyl acetate (8a)

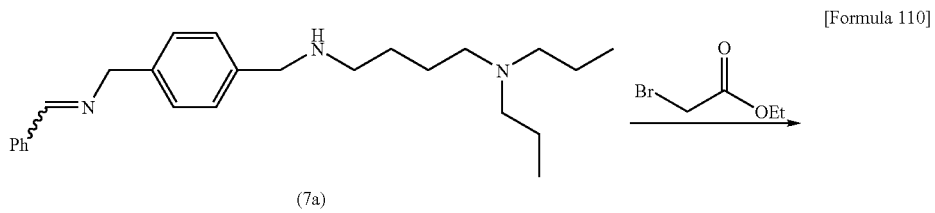

[Formula 110]

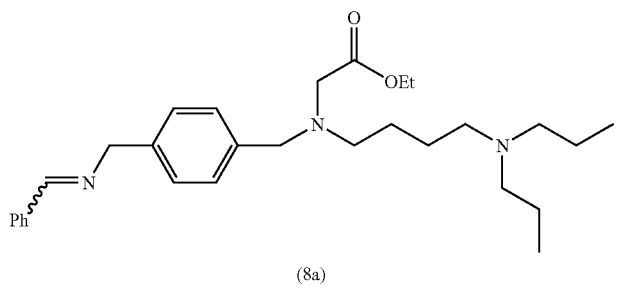

1.0 g (2.63 mmol, 1.0 equivalent) of {[4-(benzylidene)aminomethylbenzyl]-(4-dipropylaminobutyl)}amine (7a) was charged in a 50 ml recovery flask and dissolved in 10 ml of ethylene glycol dimethyl ether under a nitrogen stream. The solution was added with 544 mg (3.16 mmol, 1.2 equivalents) of ethyl bromoacetate at 25° C. and reacted at 25° C. for five hours. The reaction solution was added with 136 mg (0.79 mmol, 0.3 equivalents) of ethyl bromoacetate and 3 ml of ethylene glycol dimethyl ether and reacted at 25° C. for 24 hours.

The reaction solution was added to 30 ml of a saturated sodium bicarbonate aqueous solution, and extracted with 50 ml of toluene. The toluene layer was washed with 30 ml of a saturated sodium bicarbonate aqueous solution and 30 ml of water, dried over anhydrous sodium sulfate, filtered, and concentrated, thereby obtaining 936 mg of {[4-(benzylidene)aminomethylbenzyl]-(4-dipropylaminobutyl)amino}ethyl acetate (8a) as a yellow oily substance (yield: 76%). [HPLC: 50.4% (HPLC measurement conditions A)]

EXAMPLE 45

Production of {(4-dipropylaminobutyl)-[4-(4-methoxybenzylidene)aminomethylbenzyl]amino}ethyl acetate (30)

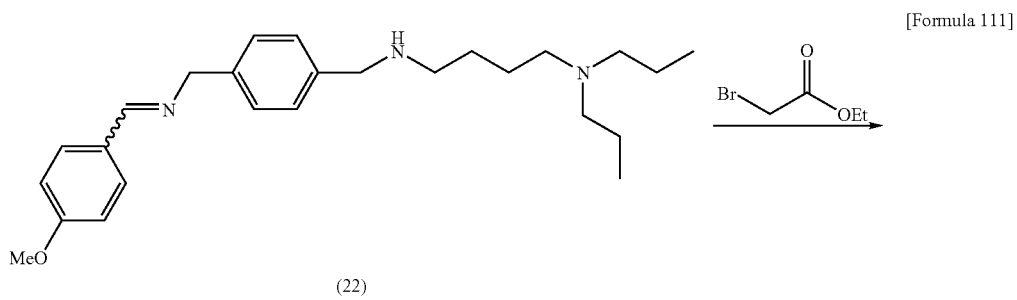

[Formula 111]

-continued

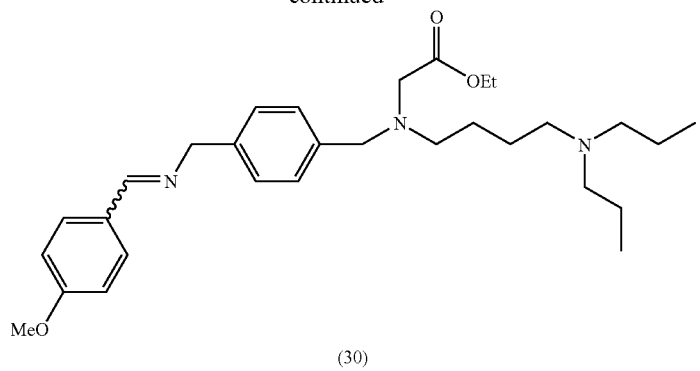

(30)

500 mg (1.22 mmol, 1.0 equivalent) of {(4-dipropylaminobutyl)-[4-(4-methoxybenzylidene)aminomethylbenzyl]}amine (22) and 5 ml of tetrahydrofuran were charged in a 100 ml recovery flask under a nitrogen stream and stirred. The mixture was added with 231 mg (1.34 mmol, 1.1 equivalents) of ethyl bromoacetate and reacted at 25° C. for 21 hours.

The reaction solution was placed in 30 ml of a saturated sodium bicarbonate aqueous solution, added with 50 ml of toluene, and subjected to phase separation. The toluene layer was washed with 30 ml of water, dried over anhydrous sodium sulfate, filtered, and concentrated, thereby obtaining 520 mg of {(4-dipropylaminobutyl)-[4-(4-methoxybenzylidene)aminomethylbenzyl]amino}ethyl acetate (30) as a slightly yellow oily substance (yield: 86%). [HPLC: 48.0% (HPLC measurement conditions A)]

EXAMPLE 46

Production of [(4-aminomethylbenzyl)-(4-dipropylaminobutyl)amino]ethyl acetate (14)

In a 50 ml recovery flask, 430 mg (0.867 mmol, 1.0 equivalent) of {(4-dipropylaminobutyl)-[4-(4-methoxybenzylidene)aminomethylbenzyl]}amino}ethyl acetate (30) was dissolved in 4.3 ml of ethanol. The solution was cooled to 0° C. After the dropwise addition of 4.3 ml of 2N hydrochloric acid over about five minutes, the mixture was stirred at 5° C. or less for 22 hours. The mixture was added with 4.3 ml of 2N hydrochloric acid at 0° C., stirred for three hours, and extracted five times with 25 ml of chloroform. The aqueous layer was slowly added with 50 ml of chloroform and 40 ml of a 3N sodium hydroxide aqueous solution to make the mixture basic, and the mixture was subjected to phase separation. The mixture was then extracted three times with 25 ml of chloroform. The extract was dried over anhydrous sodium sulfate, filtered, and concentrated, thereby obtaining 319 mg of [(4-aminomethylbenzyl)-(4-dipropylaminobutyl)amino]ethyl acetate (14) as a slightly yellow oily substance (yield: 98%). [HPLC: 95.9% (HPLC measurement conditions A)]

[Formula 112]

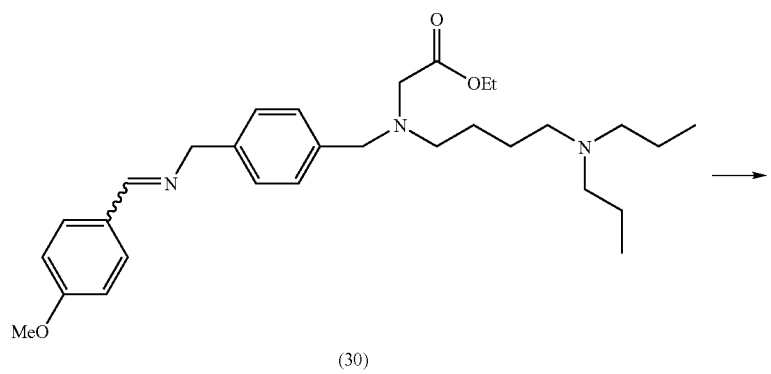

(30)

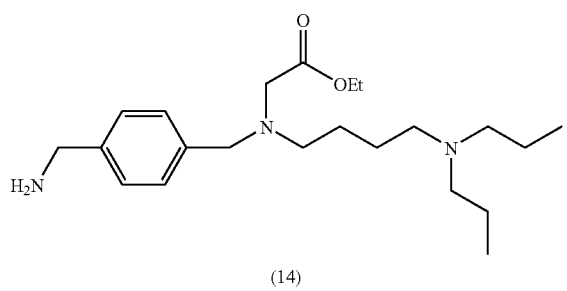

(14)

EXAMPLE 47

Production of 3-[(4-aminomethylbenzyl)-(4-dipropylaminobutyl)amino]methyl propionate (38)

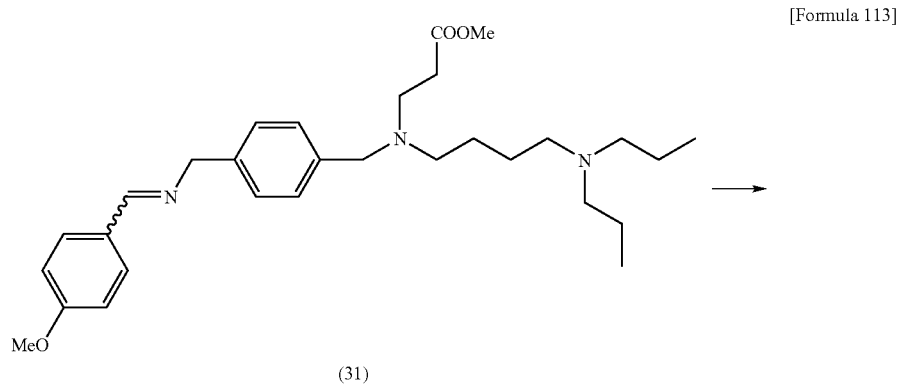

[Formula 113]

(31)

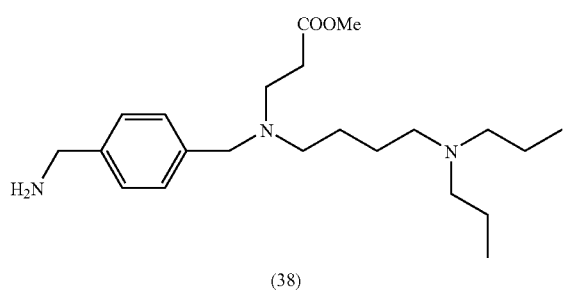

(38)

In a 50 ml recovery flask, 419.5 mg (0.85 mmol, 1.0 equivalent) of 3-{(4-dipropylaminobutyl)-[4-(4-methoxybenzylidene)aminomethylbenzyl]}amino}methyl propionate (31) was dissolved in 4.2 ml of ethanol. The solution was cooled to 0° C. After the dropwise addition of 4.2 ml of a 2N hydrochloric acid aqueous solution over about five minutes, the mixture was reacted at 0° C. for three hours. After the further addition of 4.2 ml of a 2N hydrochloric acid aqueous solution, the mixture was allowed to stand at 5° C. for 12 hours. The mixture was extracted five times with 25 ml of chloroform. The aqueous layer was slowly added with 50 ml of chloroform and 40 ml of a 3N sodium hydroxide aqueous solution to make the mixture basic. The mixture was subjected to phase separation, and extracted three times with 25 ml of chloroform. The extract was dried over anhydrous sodium sulfate, filtered, and concentrated, thereby obtaining 280.4 mg of 3-[(4-aminomethylbenzyl)-(4-dipropylaminobutyl)amino]methyl propionate (38) as a slightly yellow oily substance (yield: 98%). [HPLC: 62% (HPLC measurement conditions B)]

Property Values of 3-[(4-aminomethylbenzyl)-(4-dipropylaminobutyl)amino]methyl propionate (38)

$^1$H-NMR (400 MHz, CDCl$_3$, ppm) δ: 7.35(s, 4H, ArCH$_2$NH$_2$), 3.85(s, 2H, ArCH$_2$NH$_2$), 3.68(s, 2H, ArCH$_2$NCH$_2$), 3.65(s, 3H, —COOMe), 2.79(dd, 2H, J=7.0, 7.5 Hz, —NCH$_2$CH$_2$COOMe), 2.46(dd, 2H, J=7.1, 7.4 Hz, —NCH$_2$CH$_2$COOMe), 2.42(dd, 2H, J=6.8, 7.2 Hz, ArCH$_2$NCH$_2$CH$_2$CH$_2$CH$_2$N), 2.38~2.30(m, 6H, —NCH$_2$CH$_2$×3), 1.47-1.39(m, 8H, —NCH$_2$CH$_2$×4), 0.86 (dd, 6H, J=7.3, 7.4 Hz, —NCH$_2$CH$_2$CH$_3$×2)

$^{13}$C-NMR (100 MHz, CDCl$_3$, ppm) δ: 128.92, 128.80, 127.89, 126.88, 58.11, 56.27, 54.13, 53.53, 51.47, 49.25, 46.29, 44.51, 34.60, 32.49, 25.02, 24.85, 20.26, 11.99

EXAMPLE 48

Production of [(4-aminomethylbenzyl)-(4-dipropylaminobutyl)amino]benzyl acetate (39)

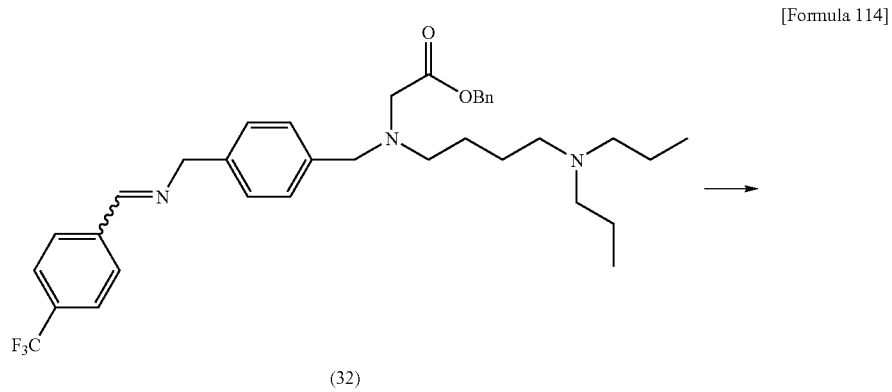

(32)

[Formula 114]

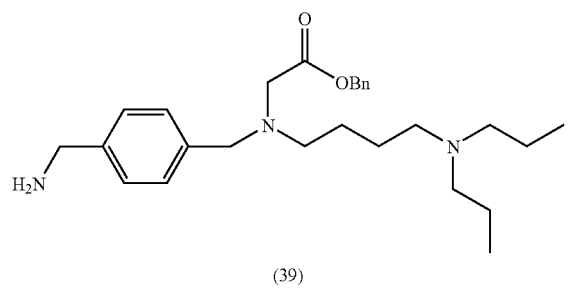

(39)

In a 50 ml recovery flask, 517 mg (0.87 mmol, 1.0 equivalent) of {(4-dipropylaminobutyl)-[4-(4-trifluoromethylbenzylidene)aminomethylbenzyl]}amino}benzyl acetate (32) was dissolved in 5.2 ml of ethanol. The solution was cooled to 0° C. After the dropwise addition of 5.2 ml of 2N hydrochloric acid over about five minutes, the mixture was reacted at 0° C. for 5.6 hours. The reaction solution was extracted five times with 25 ml of chloroform. The aqueous layer was slowly added with 50 ml of chloroform and 40 ml of a 3N sodium hydroxide aqueous solution to make the mixture basic. The mixture was subjected to phase separation, and then extracted three times with 25 ml of chloroform. The extract was dried over anhydrous sodium sulfate, filtered, and concentrated, thereby obtaining 272.9 mg of [(4-aminomethylbenzyl)-(4-dipropylaminobutyl)amino]benzyl acetate (39) as a slightly yellow oily substance (yield: 72%). [HPLC: 97% (HPLC measurement conditions B)]

Property Values of [(4-aminomethylbenzyl)-(4-dipropylaminobutyl)amino]benzyl acetate (39)

$^1$H-NMR (400 MHz, CDCl$_3$, ppm) δ: 7.35(s, 5H, —COOCH$_2$Ph), 7.27(s, 4H, ArCH$_2$NH$_2$), 5.13(s, 2H, —COOCH$_2$Ph), 3.84(s, 2H, ArCH$_2$NH$_2$), 3.76(s, 2H, ArCH$_2$NCH$_2$), 3.34 (s, 2H, —NCH$_2$COOBn), 2.64(dd, 2H, J=6.8, 7.2 Hz, ArCH$_2$NCH$_2$CH$_2$), 2.40~2.30(m, 6H, —NCH$_2$CH$_2$×3), 1.44-1.42(m, 8H, —NCH$_2$CH$_2$×4), 0.86 (dd, 6H, J=7.3, 7.4 Hz, —NCH$_2$CH$_2$CH$_3$×2)

$^{13}$C-NMR (100 MHz, CDCl$_3$, ppm) δ: 129.14, 128.55, 128.27, 126.97, 65.99, 56.19, 54.08, 46.28, 25.56, 20.16, 11.97

EXAMPLE 49

Production of [(4-aminomethylbenzyl)-(4-dipropylaminobutyl)amino]ethyl acetate (14)

[Formula 115]

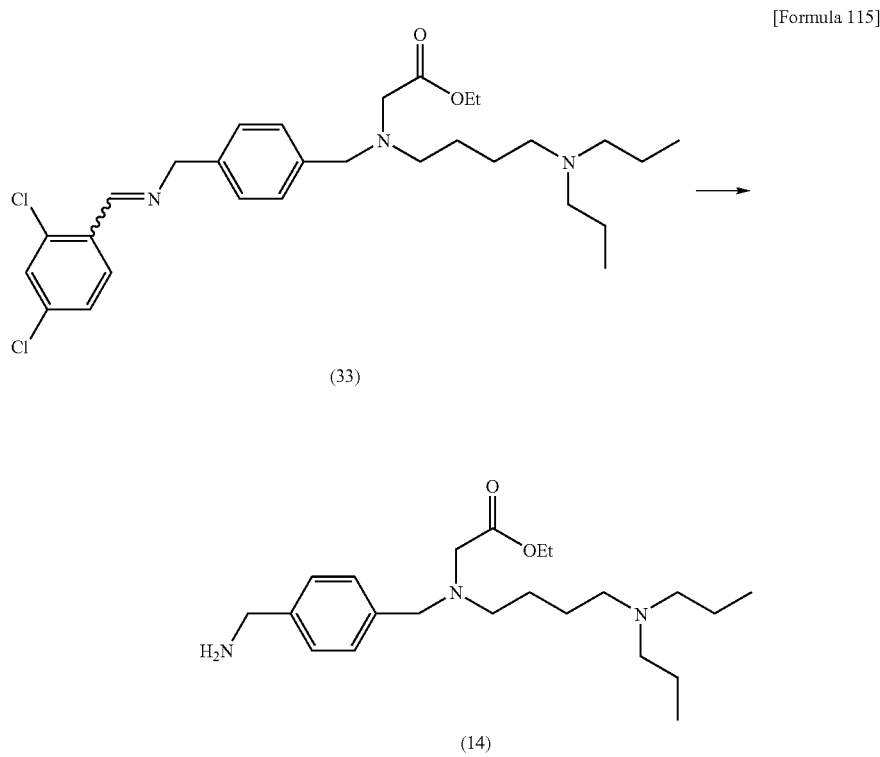

In a 50 ml recovery flask, 441.2 mg (0.825 mmol, 1.0 equivalent) of {[4-(2,4-dichlorobenzylidene)aminomethylbenzyl]-(4-dipropylaminobutyl)}amino}ethy 1 acetate (33) was dissolved in 4.4 ml of ethanol. The solution was cooled to 0° C. After the dropwise addition of 4.4 ml of a 2N hydrochloric acid aqueous solution over about five minutes, the mixture was stirred at 0° C. for 3.3 hours. The mixture was extracted five times with 25 ml of chloroform. The aqueous layer was slowly added with 50 ml of chloroform and 40 ml of a 3N sodium hydroxide aqueous solution to make the mixture basic. The mixture was The mixture was subjected to phase separation, and then extracted three times with 25 ml of chloroform. The extract was dried over anhydrous sodium sulfate, filtered, and concentrated, thereby obtaining 262.1 mg of [(4-aminomethylbenzyl)-(4-dipropylaminobutyl) amino]ethyl acetate (14) as a slightly yellow oily substance (yield: 84%, HPLC: 99%). [HPLC: 99% (HPLC measurement conditions A)]

EXAMPLE 50

Production of [(4-aminomethylbenzyl)-(4-dipropylaminobutyl)amino]ethyl acetate (14)

[Formula 116]

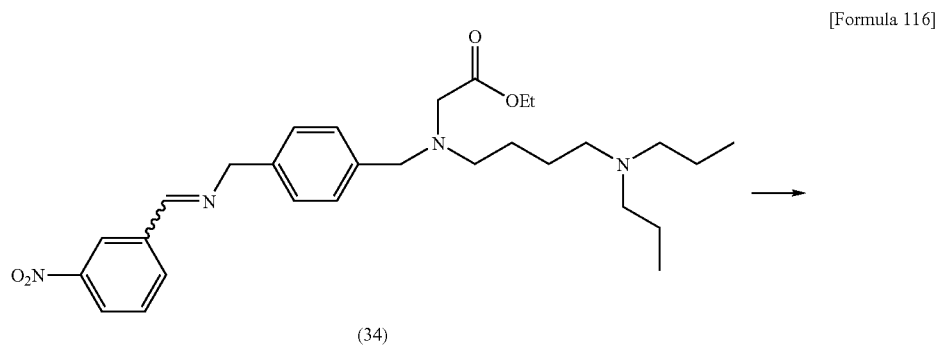

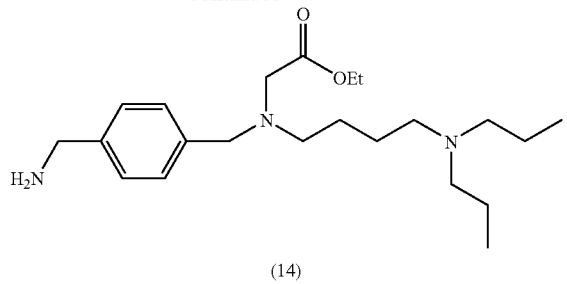

(14)

In a 50 ml recovery flask, 326.4 mg (0.639 mmol, 1.0 equivalent) of {(4-dipropylaminobutyl)-[4-(3-nitrobenzylidene)aminomethylbenzyl]amino}ethyl acetate (34) was dissolved in 3.3 ml of ethanol. The solution was cooled to 0° C. After the dropwise addition of 3.3 ml of a 2N hydrochloric acid aqueous solution over about five minutes, the mixture was reacted at 0° C. for three hours. After the addition of 3.3 ml of a 2N hydrochloric acid aqueous solution, the mixture was allowed to stand at 5° C. for 12 hours. The mixture was extracted five times with 25 ml of chloroform. The aqueous layer was added with 50 ml of chloroform and 40 ml of a 3N sodium hydroxide aqueous solution to make the mixture basic. The mixture was then subjected to phase separation and extracted three times with 25 ml of chloroform. The extract was dried over anhydrous sodium sulfate, filtered, and concentrated, thereby obtaining 2.09 g of [(4-aminomethylbenzyl)-(4-dipropylaminobutyl)amino]ethyl acetate (14) as a slightly yellow oily substance (yield: 79%). [HPLC: 96.0% (HPLC measurement conditions A)]

EXAMPLE 51

Production of (4-aminomethylbenzyl)-(4-dipropylaminobutyl)-n-hexylamine (40)

2 ml of water was charged in a 50 ml recovery flask, and cooled to 0° C. 733 mg (7.3 mmol, 10 equivalents) of concentrated sulfuric acid (97%) was slowly added to the flask. A solution prepared by dissolving 339 mg (0.73 mmol, 1.0 equivalent) of {(4-dipropylaminobutyl)-n-hexyl-[4-(5-methylfuran-2-ylmethylidene)aminomethylbenzyl]}amine (35) in 3 ml of ethanol was slowly added dropwise to the sulfuric acid aqueous solution. The mixture was stirred at 0° C. for three hours and at 25° C. for 15 hours. A solution prepared by dissolving 367 mg (3.6 mmol, 5 equivalents) of concentrated sulfuric acid (97%) in 2 ml of water was slowly added to the mixture. The mixture was then stirred at 25° C. for 24 hours.

After completion of the reaction, the reaction solution was extracted three times with 20 ml of chloroform. 50 ml of chloroform was added to the aqueous layer, and 15 ml of a 20% sodium hydroxide aqueous solution was slowly added to the mixture to make the mixture basic. The mixture was then subjected to phase separation, and extracted twice with 50 ml of chloroform. The extract was dried over anhydrous sodium sulfate, and concentrated, thereby obtaining 272 mg of (4-aminomethylbenzyl)-(4-dipropylaminobutyl)-n-hexylamine (40) as a yellow oily substance (yield: 100%). [HPLC: 78.7% (HPLC measurement conditions A)]

[Formula 117]

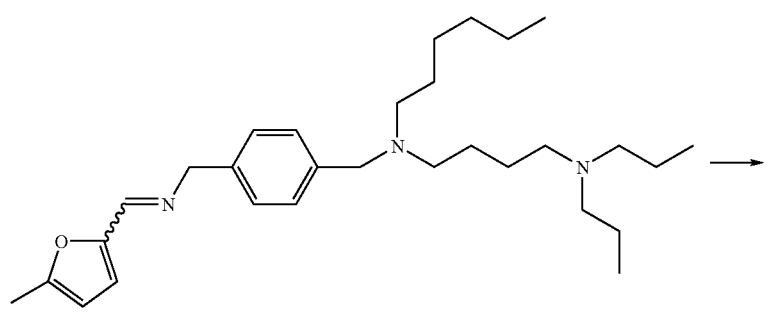

(35)

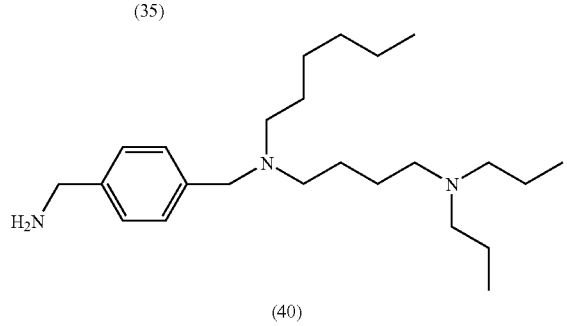

(40)

Property Values of (4-aminomethylbenzyl)-(4-dipropylaminobutyl)-n-hexylamine (40)

$^1$H-NMR (400 MHz, CDCl$_3$, ppm) δ: 7.28(d, 2H, J=8.15 Hz, ArCH$_2$NH$_2$), 7.23(d, 2H, J=8.18 Hz, ArCH$_2$NH$_2$), 3.85(s, 2H, ArCH$_2$NH$_2$), 3.52(s, 2H, ArCH$_2$NCH$_2$), 2.42-2.29(m, 10H, NCH$_2$CH$_2$×5), 1.49-1.36 (m, 10H, NCH$_2$CH$_2$×5), 1.32-1.20(m, 6H, —CH$_2$—×3), 0.87(dd, 3H, J=6.71, 7.10 Hz, N—(CH$_2$)$_5$—CH$_3$), 0.86(dd, 6H, J=7.34, 7.39 Hz, NCH$_2$CH$_2$CH$_3$×2)

$^{13}$C-NMR (100 MHz, CDCl$_3$, ppm) δ: 141.68, 138.84, 128.99, 126.78, 58.30, 56.29, 54.21, 53.81, 53.72, 46.32, 31.82, 27.15, 27.02, 25.07, 24.96, 22.67, 20.27, 14.07, 12.00

EXAMPLE 52

Production of 3-[(4-aminomethylbenzyl)-(4-dipropylaminobutyl)amino]methyl propionate (38)

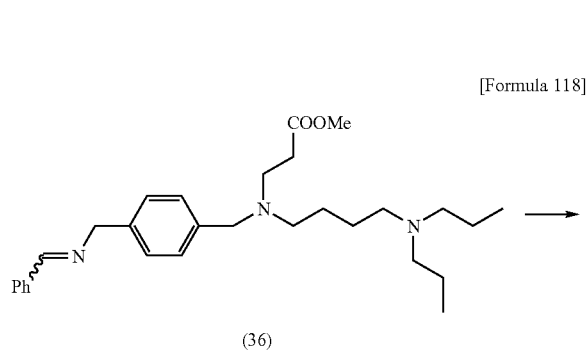

[Formula 118]

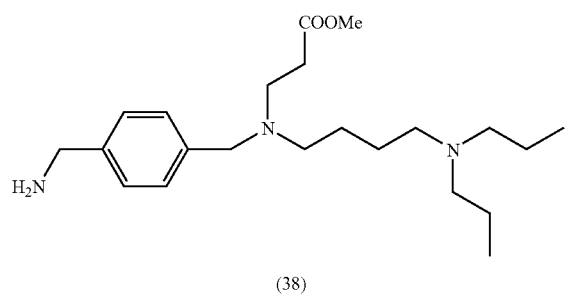

396 mg (0.85 mmol, 1.0 equivalent) of 3-{[4-(benzylidene)aminomethylbenzyl]-(4-dipropylaminobutyl)amino}methyl propionate (36) and 4 ml of methanol were charged in a 50 ml recovery flask and cooled to 0° C. After the addition of 9.2 ml (8.5 mmol, 10 equivalents) of 3N HCl, the mixture was stirred for five hours.

After completion of the reaction, the reaction solution was extracted three times with 20 ml of chloroform. After the addition of 50 ml of chloroform to the aqueous layer, 10 ml of a 20% sodium hydroxide aqueous solution was slowly added to the mixture to make the mixture basic. The mixture was then subjected to phase separation and extracted twice with 50 ml of chloroform. The extract was dried over anhydrous sodium sulfate, and concentrated, thereby obtaining 289 mg of 3-[(4-aminomethylbenzyl)-(4-dipropylaminobutyl)amino]methyl propionate (38) as a slightly yellow oily substance (yield: 90%). [HPLC: 91.7% (HPLC measurement conditions A)]

EXAMPLE 53

Production of [(4-aminomethylbenzyl)-(4-dipropylaminobutyl)amino]ethyl acetate (14)

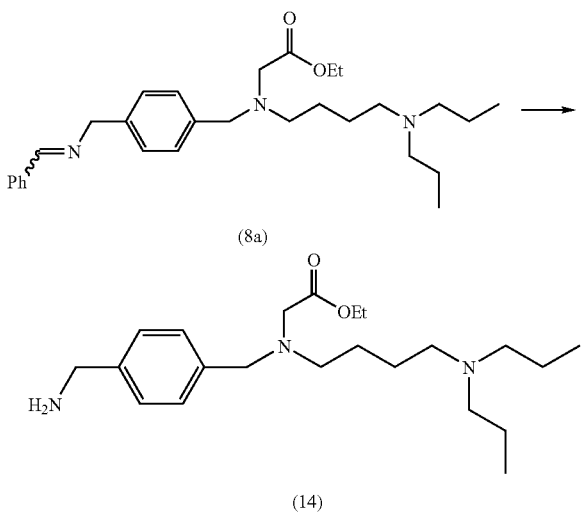

[Formula 119]

118.4 g (259 mmol, 1.0 equivalent) of {[4-(benzylidene)aminomethylbenzyl]-(4-dipropylaminobutyl)amino}ethyl acetate (8a) and 900 ml of ethanol were charged in a 3-liter four-necked flask and cooled to 0° C. The mixture was added dropwise with 870 ml (2.59 mol, 10 equivalents) of 3N hydrochloric acid over 2.5 hours and stirred at 0° C. for one hour and at 25° C. for 18 hours. About 5% of the raw material (8a) remained as a result of confirmation by HPLC. Therefore, the reaction solution was added with 110 ml of 2N hydrochloric acid at 25° C. After three hours, the content of the raw material (8a) was measured by HPLC, and it was confirmed that the content decreased to 1% or less.

The reaction solution was put in a separating funnel, and was extracted five times with 250 ml of toluene. After the addition of 500 ml of chloroform to the aqueous layer, 365 g of sodium carbonate was added to the mixture while stirring so that the mixture was adjusted to pH 9.0 or more, followed by extraction with 200 ml of chloroform. The aqueous layer was again extracted with 300 ml of chloroform. The chloroform layer was washed three times with 500 ml of a saturated sodium bicarbonate aqueous solution, then washed three times with 500 ml of 10% sodium carbonate, washed three times with 500 ml of a 1N sodium hydroxide aqueous solution, washed twice with 500 ml of a saturated sodium chloride aqueous solution, dried over anhydrous sodium sulfate, and concentrated, thereby obtaining 86.0 g of [(4-aminomethylbenzyl)-(4-dipropylaminobutyl)amino]ethyl acetate (14) as a yellow oily substance (yield: 88%, GC: 97.4%). [HPLC: 96.2% (HPLC measurement conditions A)]

EXAMPLE 54

Purification of [(4-aminomethylbenzyl)-(4-dipropylaminobutyl)amino]ethyl acetate (14) by recrystallization A solution prepared by dissolving 82.8 g (0.219 mol, 1.0 equivalent, GC: 97.4%, HPLC: 96.2% (HPLC measurement conditions A)) of [(4-aminomethylbenzyl)-(4-dipropylaminobutyl)amino]ethyl acetate (14) synthesized in Example 53 in 265 ml of ethanol was charged in a 1-liter recovery flask and cooled to 0° C. Then, 142 g (0.788 mol, 3.6 equivalents) of a 20.29% HCl-EtOH solution was added dropwise to the mixture. After one hour, the mixture was warmed to room temperature, and then stirred for 12 hours. After concentrating the reaction solution, the reaction solution was azeotropically distilled twice with 200 ml of n-hexane, thereby obtaining 115.5 g of a semi-solid product.

The product was dissolved in 725 m of t-butanol at 70° C. The solution was poured into a 2-liter conical beaker. After the addition of 250 ml of ethylene glycol dimethyl ether while stirring, a seed crystal was added at 25° C. The mixture was allowed to stand for 12 hours. The mixture was then cooled at 5° C. for two hours. The precipitated crystals were recovered by filtration, and washed with 100 ml of ethylene glycol dimethyl ether. The resulting crystals were dissolved in 500 ml of water. The mixture was adjusted to pH 9.0 or more by the addition of a 20% sodium hydroxide aqueous solution. The product was then extracted with 400 ml of chloroform, followed by 200 ml of chloroform. The chloroform layer was washed with 500 ml of a saturated sodium chloride aqueous solution and concentrated, thereby obtaining 74.3 g of [(4-aminomethylbenzyl)-(4-dipropylaminobutyl)amino]ethyl acetate (14) (yield: 89.7%, GC: 98.8%). [HPLC: 98.8% (HPLC measurement conditions A)]

EXAMPLE 55

Production of {(4-dipropylaminobutyl)-[4-(1H-imidazol-2-ylmethyl)aminomethylbenzyl]amino}ethyl acetate (41)

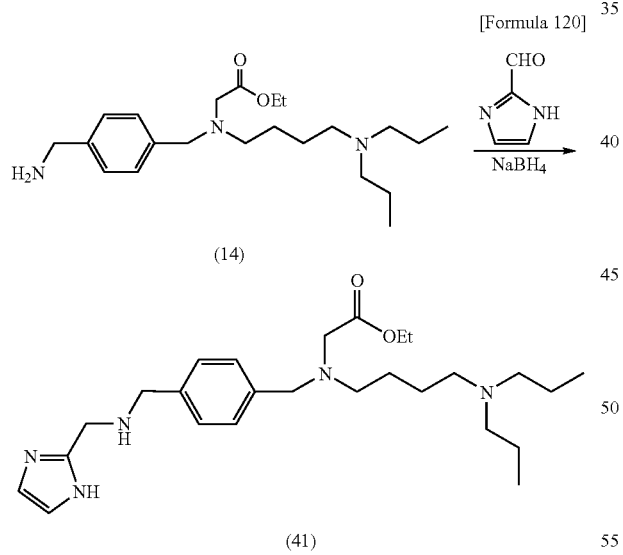

[Formula 120]

(14)

(41)

In a 1-liter four-necked flask, 28.55 g (75.6 mmol, 1.0 equivalent) of [(4-aminomethylbenzyl)-(4-dipropylaminobutyl)amino]ethyl acetate (14) was dissolved in 285.5 ml of ethanol under a nitrogen stream. 7.63 g (79.4 mmol, 1.05 equivalents) of 2-formylimidazole and 33.62 g (0.23 mol, 3.0 equivalents) of triethyl orthoformate were added to the solution while stirring under cooling with ice, and the mixture was stirred at room temperature for 44 hours.

The reaction solution was added dropwise to a solution prepared by dissolving 4.29 g (113 mmol, 1.5 equivalents) of sodium borohydride in 286 ml of ethanol under cooling with ice over 45 minutes so that the solution temperature was not 0° C. or more. The mixture was further stirred at 0° C. or less for 3.5 hours.

The reaction solution was added to 756 ml (10 equivalents) of 1 mol/l hydrochloric acid under cooling with ice. After that, the reaction solution was added with 756 ml of an aqueous solution of 96.1 g (12 equivalents) of sodium carbonate to adjust to pH 9, the mixture was extracted three times with 500 ml of toluene. Under cooling with ice the obtained organic layer was washed with 500 ml of a saturated sodium chloride aqueous solution, washed with 500 ml of distilled water, dried over anhydrous sodium sulfate, filtered, and concentrated, thereby obtaining 34.81 g of {(4-dipropylaminobutyl)-[4-(1H-imidazol-2-ylmethyl)aminomethylbenzyl]amino}ethyl acetate (41) as a light yellow oily substance (yield: 100%). [HPLC: 94.8% (HPLC measurement conditions D)]

Property values of {(4-dipropylaminobutyl)-[4-(1H-imidazol-2-ylmethyl)aminomethylbenzyl]amino}ethyl acetate (41)

$^1$H-NMR (400 MHz, CDCl$_3$, ppm) δ: 7.30(d, 2H, J=8.02 Hz, Ph), 7.23(d, 2H, J=8.08 Hz, Ph), 6.97(s, 2H, imidazole-), 4.15(q, 2H, J=7.14 Hz, —COOCH$_2$CH$_3$), 3.91(s, 2H, imidazole-CH$_2$), 3.78(s, 2H, ArCH$_2$NH), 3.75(s, 2H, ArCH$_2$NCH$_2$), 3.29(s, 2H, —NCH$_2$COOEt), 2.62(dd, 2H, J=6.72, 7.07 Hz, ArCH$_2$NCH$_2$CH$_2$), 2.40~2.30(m, 6H, NCH$_2$CH$_2$×3), 1.49~1.36(m, 8H, NCH$_2$CH$_2$×4), 1.26(dd, 3H, J=7.13, 7.15 Hz, —COOCH$_2$CH$_3$), 0.86(dd, 6H, J=7.31, 7.41 Hz, NCH$_2$CH$_2$CH$_3$×2)

$^{13}$C-NMR (100 MHz, CDCl$_3$, ppm) δ: 171.58, 147.21, 138.30, 138.26, 129.14, 128.09, 60.19, 57.95, 56.20, 54.27, 53.97, 53.65, 53.35, 46.57, 25.52, 24.49, 20.20, 14.30, 12.00

EXAMPLE 56

Production of {(4-dipropylaminobutyl)-[4-(1H-imidazol-2-ylmethylidene)aminomethylbenzyl]amino}ethyl acetate (37)

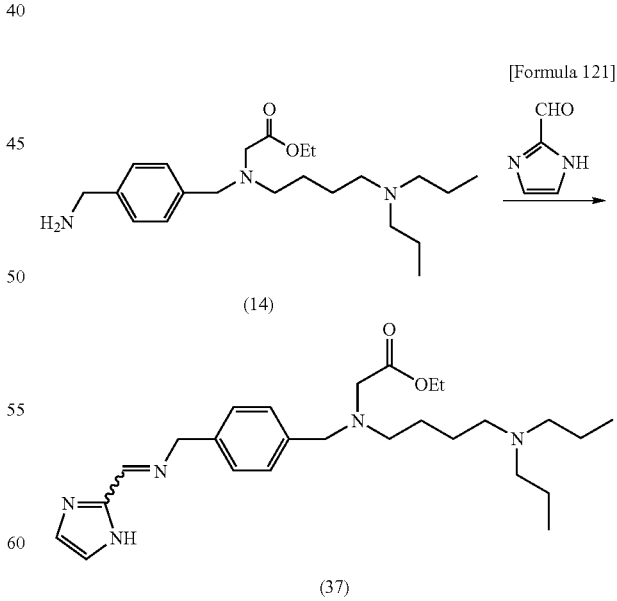

[Formula 121]

(14)

(37)

1.02 g (10.6 mmol, 1.05 equivalents) of 2-formylimidazole and 50 ml of methanol were charged in a 200 ml four-necked flask under a nitrogen stream and stirred. The mixture was added with 3.81 g (10.1 mmol, 1.0 equivalent) of [(4-aminomethylbenzyl)-(4-dipropylaminobutyl)amino]ethyl acetate (14) and 10.6 g of anhydrous sodium sulfate and then stirred at 26° C. for 24 hours.

After completion of the reaction, the reaction solution was poured into 50 ml of a saturated sodium bicarbonate aqueous solution, added with 100 ml of chloroform, and subjected to phase separation. The reaction solution was again extracted with 100 ml of chloroform, washed twice with 30 ml of a saturated sodium bicarbonate aqueous solution, washed twice with 30 ml of water, dried over anhydrous sodium sulfate, filtered, and concentrated, thereby obtaining 4.56 g of {(4-dipropylaminobutyl)-[4-(1H-imidazol-2-ylmethylidene) aminomethylbenzyl]amino}ethyl acetate (37) as a reddish brown oily substance (yield: 99%). [HPLC: 93.3% (HPLC measurement conditions C)]

EXAMPLE 57

Production of {(4-dipropylaminobutyl)-[4-(1H-imidazol-2-ylmethyl)aminomethylbenzyl]amino}ethyl acetate (41)

filtered, and concentrated, thereby obtaining 1.03 g of {(4-dipropylaminobutyl)-[4-(1H-imidazol-2-ylmethyl)aminomethylbenzyl]amino}ethyl acetate (41) as a yellow oily substance (yield: 89%). [HPLC: 89.4% (HPLC measurement conditions C)]

EXAMPLE 58

Production of Sulfate of {(4-dipropylaminobutyl)-[4-(1H-imidazol-2-ylmethyl)aminomethylbenzyl]amino}ethyl acetate (41)

(1) Production of Sulfate

In a 200 ml recovery flask, 1.32 mg (2.88 mmol, HPLC: 94.8% (HPLC measurement conditions D)) of {(4-dipropylaminobutyl)-[4-(1H-imidazol-2-ylmethyl)aminomethylbenzyl]amino}ethyl acetate (41) synthesized in Example 55 was dissolved in 30 ml of ethanol. A solution prepared by

[Formula 122]

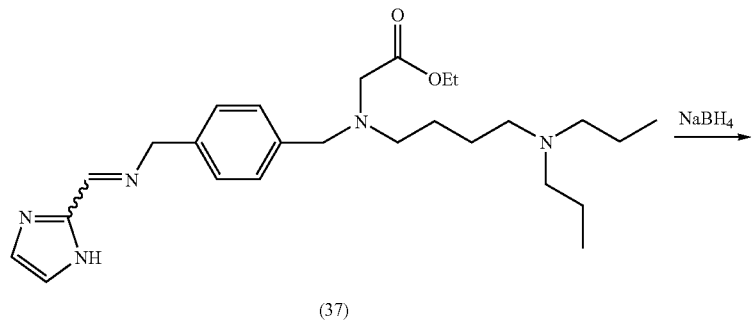

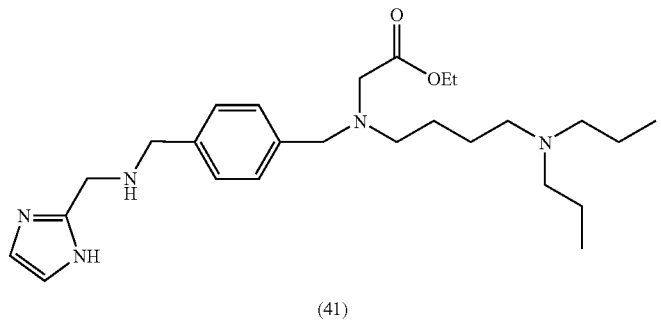

5 ml of ethanol and 155 mg (3.37 mmol, 1.5 equivalents) of sodium borohydride were added in a 200 ml three-necked flask under a nitrogen stream. The mixture was then cooled to 0° C. A solution prepared by dissolving 1.14 g (2.51 mmol, 1.0 equivalent) of {(4-dipropylaminobutyl)-[4-(1H-imidazol-2-ylmethylidene)aminomethylbenzyl]amino}ethyl acetate (37) in 6 ml of EtOH was added dropwise to the flask over about 10 minutes, after that the mixture was stirred at 0° C. for 3.5 hours.

The reaction solution was slowly added to 30 ml of 1N hydrochloric acid at 0° C. The mixture was added with 100 ml of toluene and 50 ml of a 1N sodium hydroxide aqueous solution. The mixture was subjected to phase separation and then extracted again with 100 ml of toluene. The organic layer was washed twice with 20 ml of a saturated sodium bicarbonate aqueous solution, dried over anhydrous sodium sulfate, dissolving 570 mg (5.64 mmol, 1.96 equivalents) of 97% sulfuric acid in 10 ml of ethanol was added dropwise at 25° C. over 10 minutes, and the mixture was heated to 60° C. A solution prepared by dissolving 222 mg (2.2 mmol, 0.76 equivalents) of 97% sulfuric acid in 7 ml of ethanol was further added dropwise to the mixture at 60° C. over 10 minutes. After that, seed crystals were added to the mixture at 60° C. The mixture was cooled to 25° C. over four hours, and stirred for 12 hours. The precipitated crystals were recovered by filtration, washed twice with 5 ml of ethanol, further washed with 5 ml of ethylene glycol dimethyl ether, and dried under vacuum at 40° C., thereby obtaining 1.73 g of sulfate of {(4-dipropylaminobutyl)-[4-(1H-imidazol-2-ylmethyl)aminomethylbenzyl]amino}ethyl acetate (41) as white crystals (yield: 80% (as sulfate)). [HPLC: 99.5% (HPLC measurement conditions D)]

Property Values of Sulfate of {(4-dipropylaminobutyl)-[4-(1H-imidazol-2-ylmethyl)aminomethylbenzyl]amino}ethyl acetate (41)

$^1$H-NMR (400 MHz, DMSO-$d_6$+$D_2O$, ppm) δ: 7.51(d, 2H, J=8.3 Hz, Ph-), 7.47(d, 2H, J=8.3 Hz, Ph-), 7.37(s, 2H, imidazole), 4.28(s, 2H, imidazole-$CH_2$), 4.21(s, 2H, Ar$CH_2$NH), 4.12(q, 2H, —$CO_2CH_2CH_3$), 4.06(bs, 2H, Ar$CH_2$N$CH_2$), 3.45(s, 2H, —N$CH_2CO_2$Et), 3.05-2.88(m, 8H, N$CH_2CH_2$×4), 1.66-1.58(m, 8H, N$CH_2CH_2$×4), 1.20(t, 3H, J=7.1 Hz, —$CO_2CH_2CH_3$), 0.92(t, 6H, J=7.1 Hz, N$CH_2CH_2CH_3$×2)

$^{13}$C-NMR (100 MHz, DMSO-$d_6$+$D_2O$, ppm) δ: 139.5, 130.4, 130.1, 121.8, 61.13, 57.16, 53.69, 51.68, 50.11, 41.79, 40.13, 39.92, 39.08, 38.88, 20.57, 16.74, 14.11, 10.90

(2) Production of Sulfate-Free Amine (41)

10.0 g of sulfate of {(4-dipropylaminobutyl)-[4-(1H-imidazol-2-ylmethyl)aminomethylbenzyl]amino}ethyl acetate (41) was suspended in 200 ml of chloroform. The suspension was added with 100 ml of distilled water and 100 ml of a 1 mol/l sodium hydroxide aqueous solution under cooling with ice to adjust to pH 10 or more. The mixture was extracted three times with 100 ml of chloroform. The obtained chloroform layer was washed with 300 ml of a saturated sodium chloride aqueous solution, dried over anhydrous sodium sulfate, filtered, concentrated under reduced pressure, azeotropically distilled with ethanol, and dried under vacuum, thereby obtaining 6.60 g of {(4-dipropylaminobutyl)-[4-(1H-imidazol-2-ylmethyl)aminomethylbenzyl]amino}ethyl acetate (41).

EXAMPLE 59

Production of {(4-dipropylaminobutyl)-[4-(1-methylimidazol-2-ylmethyl)aminomethylbenzyl]amino}ethyl acetate (42)

6.5 ml of ethanol and 121 mg (3.20 mmol, 1.2 equivalents) of sodium borohydride were charged in a 50 ml recovery flask under a nitrogen stream. The mixture was then cooled to 0° C. A solution prepared by dissolving 1.14 g (2.51 mmol, 1.0 equivalent) of {(4-dipropylaminobutyl)-[4-(1-methylimidazol-2-ylmethylidene)aminomethylbenzyl]amino}ethyl acetate (29) in 6.5 ml of ethanol was added dropwise to the mixture at −2 to 0° C. over about 10 minutes. After six hours, 121 mg (3.20 mmol, 1.2 equivalents) of sodium borohydride was added to the mixture. After nine hours, 121 mg (3.20 mmol, 1.2 equivalents) of sodium borohydride was further added to the mixture. The mixture was stirred at −2 to 0° C. for 11 hours.

The reaction solution was added to 30 ml of 1N hydrochloric acid at 0° C. The mixture was added with 50 ml of toluene and 50 ml of a 1N sodium hydroxide aqueous solution, then subjected to phase separation. The reaction solution was then extracted twice with 50 ml of toluene. The organic layer was washed twice with 30 ml of a saturated sodium bicarbonate aqueous solution, washed twice with 30 ml of water, dried over anhydrous sodium sulfate, filtered, and concentrated, thereby obtaining 731.2 mg of {(4-dipropylaminobutyl)-[4-(1-methylimidazol-2-ylmethyl)aminomethylbenzyl]amino}ethyl acetate (42) as a slightly yellow oily substance (yield: 58%). [HPLC: 87% (HPLC measurement conditions D)]

Property values of {(4-dipropylaminobutyl)-[4-(1-methylimidazol-2-ylmethyl)aminomethylbenzyl]amino}ethyl acetate (42)

$^1$H-NMR (400 MHz, CDCl$_3$, ppm) δ: 7.28 (m, 4H, Ph-), 6.93(s, 1H, Me-imidazole-), 6.81(s, 1H, Me-imidazole-), 4.15(q, 2H, J=7.1 Hz, —$COOCH_2CH_3$), 3.84(s, 2H, Ar$CH_2$NH$CH_2$-imidazole), 3.81(s, 2H, Ar$CH_2$NH$CH_2$-imidazole), 3.75(s, 2H, Ar$CH_2$N$CH_2$), 3.64(s, 3H, Me-imida-

[Formula 123]

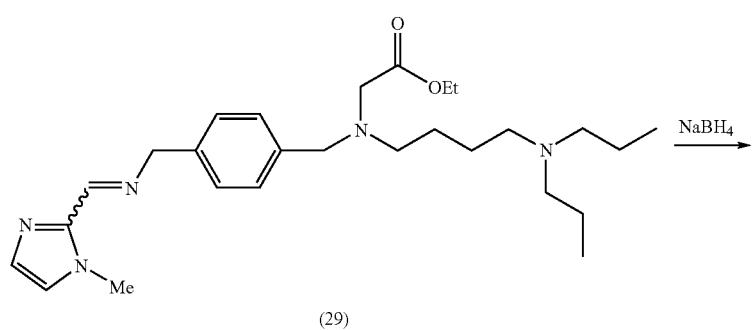

(29)

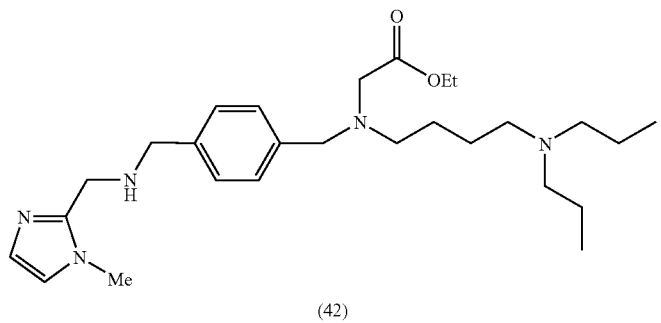

(42)

zole-), 3.28(s, 2H, —NCH$_2$COOEt), 2.63(dd, 2H, J=6.6, 6.3 Hz, ArCH$_2$NCH$_2$CH$_2$), 2.40~2.33(m, 6H, NCH$_2$CH$_2$×3), 1.46-1.40 (m, 8H, NCH$_2$CH$_2$×4), 1.26(t, 3H, J=7.1 Hz, —COOCH$_2$CH$_3$), 0.86(dd, 6H, J=7.3, 7.4 Hz, NCH$_2$CH$_2$CH$_3$×2)

$^{13}$C-NMR (100 MHz, CDCl$_3$, ppm) δ: 171.58, 138.62, 137.96, 129.00, 129.90, 127.19, 121.17, 60.15, 57.86, 56.23, 54.15, 54.07, 53.79. 53.28, 45.16, 32.70, 25.53, 24.71, 20.20, 14.30, 11.98

EXAMPLE 60

Production of {(4-dipropylaminobutyl)-[4-(1-methylimidazol-2-ylmethyl)aminomethylbenzyl]amino}ethyl acetate (42)

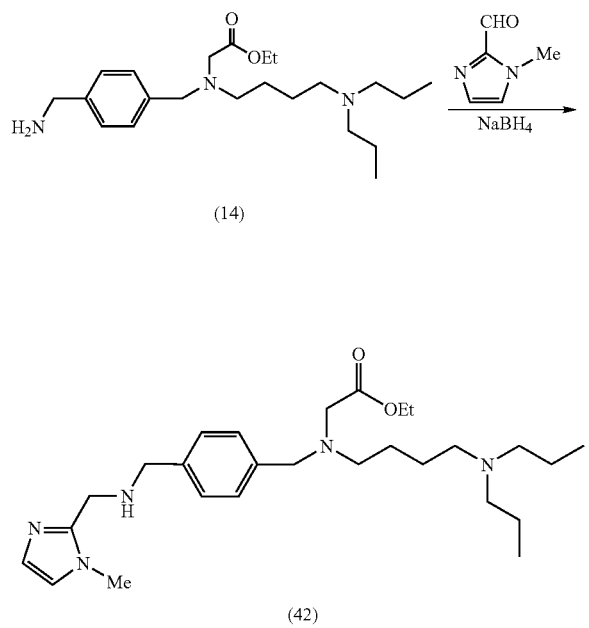

[Formula 124]

1.09 g (9.92 mmol, 1.0 equivalent) of 2-formyl-1-methylimidazole and 37 ml of ethanol was charged in a 200 ml four-necked flask under a nitrogen stream. The mixture was then stirred. The mixture was added with 3.75 g (9.92 mmol, 1.0 equivalent) of [(4-aminomethylbenzyl)-(4-dipropylaminobutyl)amino]ethyl acetate (14) and further 4.41 g (29.8 mmol, 3.0 equivalents) of triethyl orthoformate and then stirred at 20° C. for 39 hours.

The reaction solution was cooled to −20° C., and added with 8.74 g (99.2 mmol, 10 equivalents) of ethyl acetate and 490 mg (11 mmol, 1.2 equivalents) of sodium borohydride, and the mixture was stirred at −20° C. for six hours and at 20° C. for three days.

The reaction solution was added to 100 ml of water, and the mixture was extracted with 100 ml of toluene, washed three times with 50 ml of a saturated sodium bicarbonate aqueous solution, washed with 50 ml of water, dried over anhydrous sodium sulfate, filtered, and concentrated, thereby obtaining 4.63 g of {(4-dipropylaminobutyl)-[4-(1-methylimidazol-2-ylmethyl)aminomethylbenzyl]amino}ethyl acetate (42) as a yellow oily substance (yield: 99%). [HPLC: 84.5% (HPLC measurement conditions C)]

EXAMPLE 61

Production of {(4-dipropylaminobutyl)-[4-(1H-imidazol-2-ylmethylidene)aminomethylbenzyl]methyl}amine (43)

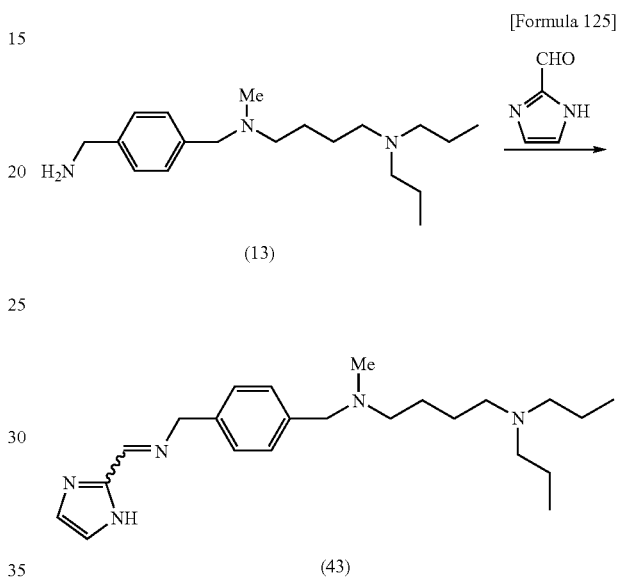

[Formula 125]

456 mg (1.49 mmol, 1.0 equivalent) of 4-[(4-dipropylaminobutyl)methylamino]methylbenzylamine (13) and 11 ml of ethanol were charged in a 50 ml recovery flask under a nitrogen stream. The mixture was then stirred. The mixture was added with 215 mg (2.24 mmol, 1.5 equivalents) of 2-formylimidazole and 507 mg (4.78 mmol, 3.2 equivalents) of trimethyl orthoformate at 20° C. while stirring, further stirred at 20° C. for 18 hours.

The reaction system was concentrated under reduced pressure. The residue was added with 30 ml of distilled water, and extracted twice with 30 ml of toluene. The combined organic layer was washed with 30 ml of a saturated sodium chloride aqueous solution, dried over anhydrous sodium sulfate, filtered, and concentrated under reduced pressure, thereby obtaining 560 mg of {(4-dipropylaminobutyl)-[4-(1H-imidazol-2-ylmethylidene)aminomethylbenzyl]methyl}amine (43) as a yellow oily substance (yield: 98%). [HPLC: 87.0% (HPLC measurement conditions C)]

Property values of {(4-dipropylaminobutyl)-[4-(1H-imidazol-2-ylmethylidene)aminomethylbenzyl]methyl}amine (43)

$^{1}$H-NMR (400 MHz, CDCl$_3$, ppm) δ: 8.32(s, 1H, HC=N), 7.29(d, 2H, J=8.07 Hz, Ar—), 7.23(d, 2H, J=8.09 Hz, Ar—), 7.07(bs, 2H, imidazole-), 4.76(s, 2H, ArCH$_2$N=CH), 3.46(s, 2H, ArCH$_2$NCH$_2$), 2.42~2.30(m, 8H, NCH$_2$CH$_2$×4), 2.18(s, 3H, —NMe), 1.50~1.38(m, 8H, NCH$_2$CH$_2$×4), 0.86(dd, 6H, J=7.34, 7.38 Hz, NCH$_2$CH$_2$CH$_3$×2)

EXAMPLE 62

Production of {(4-dipropylaminobutyl)-[4-(1H-imidazol-2-ylmethyl)aminomethylbenzyl]methyl}amine (44)

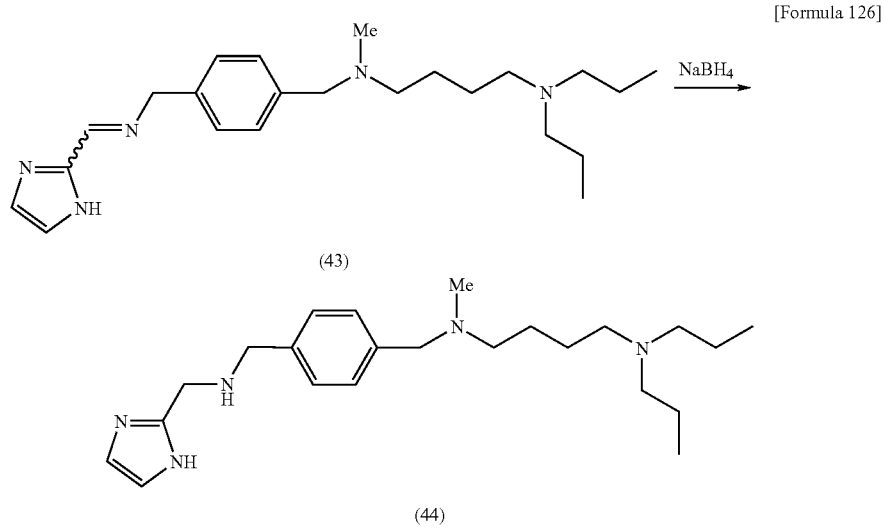

[Formula 126]

560 mg (1.46 mmol, 1.0 equivalent) of {(4-dipropylaminobutyl)-[4-(1H-imidazol-2-ylmethylidene)aminomethylbenzyl]methyl}amine (43) and 12 ml of methanol were charged in a 50 ml recovery flask under a nitrogen stream. The mixture was then stirred. 113 mg (2.92 mol, 2.0 equivalents) of sodium borohydride was added to the mixture at 0° C. The mixture was then stirred at 0° C. for one hour and at 20° C. for one hour.

The reaction system was concentrated under reduced pressure. The residue was added with 30 ml of distilled water, and the mixture was extracted twice with 30 ml of toluene. The combined organic layer was added with 10 ml of a 3% hydrochloric acid aqueous solution, the mixture was subjected to back extraction. The aqueous layer was return to alkaline by adding 15 ml of a 1N sodium hydroxide aqueous solution, and the mixture was extracted twice with 30 ml of toluene. The organic layer was washed with 30 ml of a saturated sodium chloride aqueous solution, dried over anhydrous sodium sulfate, filtered, and concentrated under reduced pressure, thereby obtaining 546 mg of {(4-dipropylaminobutyl)-[4-(1H-imidazol-2-ylmethyl)aminomethylbenzyl]methyl}amine (44) as a light yellow oily substance (yield: 97%). [HPLC: 95.5% (HPLC measurement conditions C)]

Property Values of {(4-dipropylaminobutyl)-[4-(1H-imidazol-2-ylmethyl)aminomethylbenzyl]methyl}amine (44)

$^1$H-NMR (400 MHz, CDCl$_3$, ppm) δ: 7.27(d, 2H, J=8.23 Hz, Ar—), 7.23(d, 2H, J=8.30 Hz, Ar—), 6.97(s, 2H, imidazole-), 3.91(s, 2H, ArCH$_2$NCH$_2$-imidazole), 3.78(s, 2H, ArCH$_2$NCH$_2$-imidazole), 3.45(s, 2H, ArCH$_2$NCH$_2$), 2.42~2.31(m, 8H, NCH$_2$CH$_2$×4), 2.17(s, 3H, —NMe), 1.50~1.36(m, 8H, NCH$_2$CH$_2$×4), 0.86(dd, 6H, J=7.34, 7.38 Hz, NCH$_2$CH$_2$CH$_3$×2)

EXAMPLE 63

Production of {(4-dipropylaminobutyl)-[4-(1H-imidazol-2-ylmethyl)aminomethylbenzyl]methyl}amine (44)

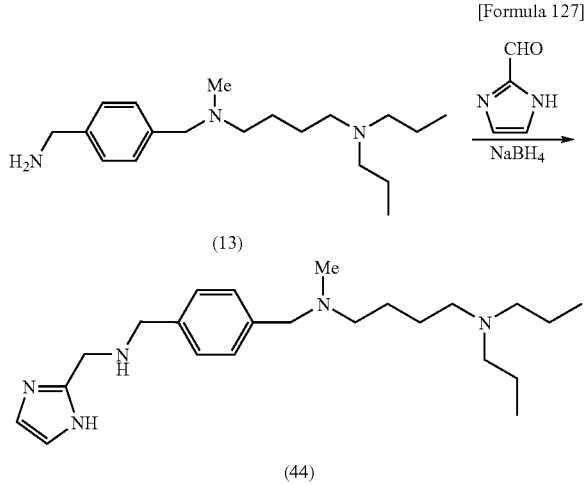

[Formula 127]

534 mg (1.75 mmol, 1.0 equivalent) of 4-[(4-dipropylaminobutyl)methylamino]methylbenzylamine (13) and 13 ml of ethanol were charged in a 50 ml recovery flask under a nitrogen stream. The mixture was then stirred. The mixture was added with 185 mg (1.93 mmol, 1.1 equivalents) of 2-formylimidazole and 594 mg (5.6 mmol, 3.2 equivalents) of trimethyl orthoformate, and stirred at 20° C. for 22 hours. 132 mg (3.5 mmol, 2.0 equivalents) of sodium borohydride was added to the mixture at 0° C. The mixture was then stirred at 0° C. for one hour and at room-temperature for one hour.

The reaction system was concentrated under reduced pressure. The residue was added with 30 ml of distilled water, and the mixture was extracted twice with 30 ml of toluene. The combined organic layer was added with 10 ml of a 3% hydrochloric acid aqueous solution, the mixture was subjected to back extraction. The aqueous layer was return to alkaline by adding 15 ml of a 1N sodium hydroxide aqueous solution, and the mixture was extracted twice with 30 ml of toluene. The organic layer was washed with 30 ml of a saturated sodium chloride aqueous solution, dried over anhydrous sodium sulfate, filtered, and concentrated under reduced pressure, thereby obtaining 670 mg of {(4-dipropylaminobutyl)-[4-(1H-imidazol-2-ylmethyl)aminomethylbenzyl]methyl}amine (44) as a light yellow oily substance (yield: 99%). [HPLC: 94.6% (HPLC measurement conditions C)]

EXAMPLE 64

Production of {(4-dipropylaminobutyl)-[4-(1H-imidazol-2-ylmethyl)-(1-methylimidazol-2-ylmethyl)aminomethylbenzyl]amino}ethyl acetate (45)

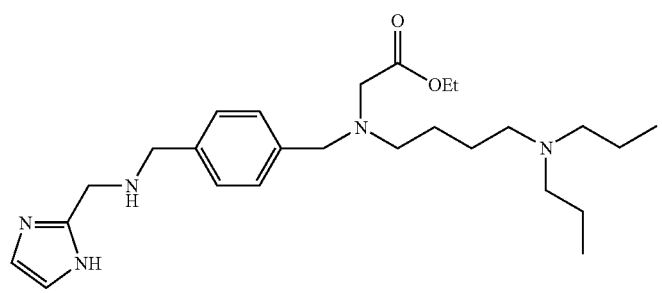

(41)

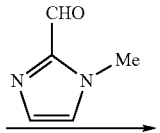

[Formula 128]

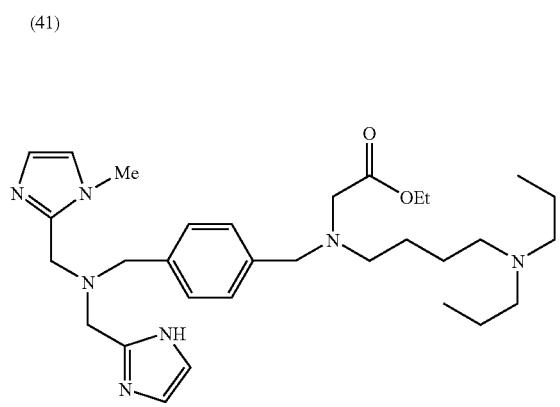

(45)

Under a nitrogen stream 6.60 mg (14.4 mmol) of {(4-dipropylaminobutyl)-[4-(1H-imidazol-2-ylmethyl)aminomethylbenzyl]amine}ethyl acetate (41) and 132 ml of ethanol were charged in a 300 ml four-necked flask, further 1.91 g (17.3 mmol, 1.2 equivalents) of 2-formyl-1-methylimidazole and 7.34 g (34.6 mmol, 2.4 equivalents) of sodium triacetoxyborohydride were added to the mixture while stirring under cooling with ice, and the mixture was stirred at 25° C. for 17 hours.

The reaction solution was added to 250 ml of a saturated sodium bicarbonate aqueous solution cooled with ice, and extracted three times with 250 ml of toluene. The obtained organic layer was washed with 250 ml of a saturated sodium chloride aqueous solution, washed with 250 ml of water, dried over anhydrous sodium sulfate, filtered, concentrated under reduced pressure, azeotropically distilled with ethanol, and dried under vacuum, thereby obtaining 7.12 g of {(4-dipropylaminobutyl)-[4-(1H-imidazol-2-ylmethyl)-(1-methylimidazol-2-ylmethyl)aminomethylbenzyl]amino}ethyl acetate (45) as a light yellow oily substance (yield: 89.4%). [HPLC: 99.4% (HPLC measurement conditions D)]

Property Values of {(4-dipropylaminobutyl)-[4-(1H-imidazol-2-ylmethyl)-(1-methylimidazol-2-ylmethyl)aminomethylbenzyl]amino}ethyl acetate (45)

$^1$H-NMR (400 MHz, CDCl$_3$, ppm) δ: 7.34(d, 2H, J=8.20 Hz, Ph), 7.30(d, 2H, J=8.22 Hz, Ph), 7.09(s, 2H, imidazole-), 6.99(d, 1H, J=1.28 Hz, Me-imidazole-), 6.87(d, 1H, J=1.26 Hz, Me-imidazole-), 4.15(q, 2H, J=7.14 Hz, —COOCH$_2$CH$_3$), 3.76(s, 2H, ArCH$_2$N), 3.67(s, 2H, ArCH$_2$N), 3.62(s, 2H, ArCH$_2$N), 3.55(s, 3H, Me-imidazole-), 3.47(s, 2H, ArCH$_2$N), 3.28(s, 2H, —NCH$_2$COOEt), 2.63(dd, 2H, J=6.77, 7.27 Hz, PhCH$_2$NCH$_2$CH$_2$), 2.40~2.30 (m, 6H, NCH$_2$CH$_2$×3), 1.49~1.36(m, 8H, NCH$_2$CH$_2$×4), 1.26(t, 3H, J=7.14 Hz, —COOCH$_2$CH$_3$), 0.85(dd, 6H, J=7.33, 7.40 Hz, NCH$_2$CH$_2$CH$_3$×2)

$^{13}$C-NMR (100 MHz, CDCl$_3$, ppm) δ: 171.56, 145.62, 143.09, 138.27, 137.57, 129.05, 128.94, 127.91, 126.82, 121.61, 116.22, 60.15, 58.86, 57.90, 56.26, 54.19, 54.10, 53.86, 48.89, 47.01, 32.71, 25.53, 24.81, 20.25, 14.30, 11.99

EXAMPLE 65

Production of {(4-dipropylaminobutyl)-[4-(1H-imidazol-2-ylmethyl)-(1-methylimidazol-2-ylmethyl)aminomethylbenzyl]methyl}amine (46)

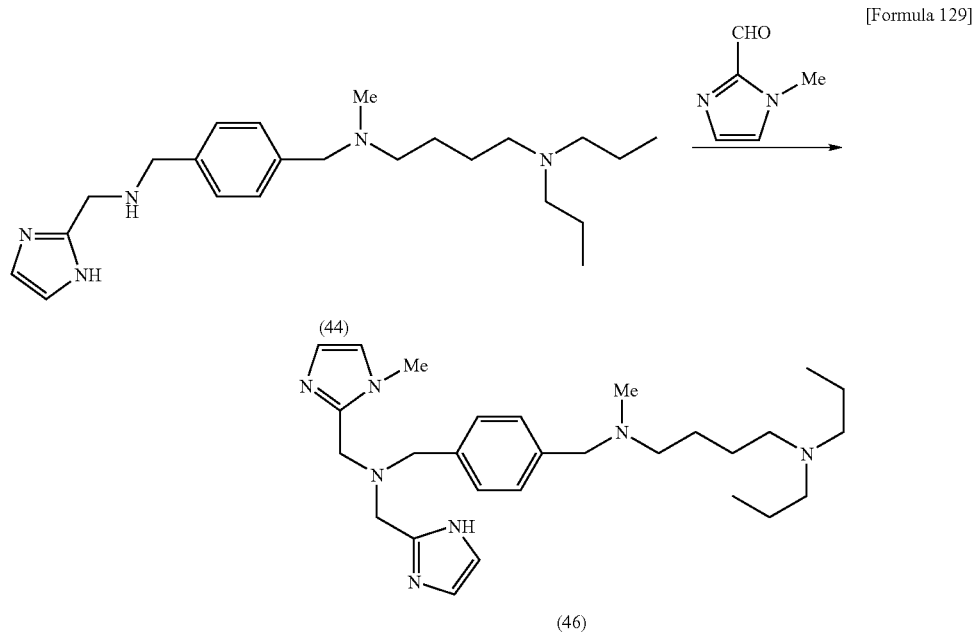

[Formula 129]

511 mg (1.33 mmol, 1.0 equivalent) of {(4-dipropylaminobutyl)-[4-(1H-imidazol-2-ylmethyl)aminomethylbenzyl]methyl}amine (44), 8 ml of ethanol, and 219 mg (1.99 mmol, 1.5 equivalents) of 2-formyl-1-methylimidazole were charged in a 50 ml recovery flask under a nitrogen stream. The mixture was stirred and then cooled to −10° C. 843 mg (3.98 mmol, 3.0 equivalents) of sodium triacetoxyborohydride was added to the mixture at −10° C., the mixture was then warmed to 20° C. over 30 minutes and stirred for 19 hours.

The reaction solution was added with 12 ml of a saturated sodium bicarbonate aqueous solution, and the mixture was concentrated under reduced pressure. The residue was added with 50 ml of distilled water, the mixture was extracted twice with 50 ml of toluene. The organic layer was washed with 40 ml of a saturated sodium chloride aqueous solution, dried over anhydrous sodium sulfate, filtered, and concentrated under reduced pressure, thereby obtaining 621 mg of {(4-dipropylaminobutyl)-[4-(1H-imidazol-2-ylmethyl)-(1-methylimidazol-2-ylmethyl)aminomethylbenzyl]methyl}amine (46) as a light yellow oily substance (yield: 98%). [HPLC: 98.9% (HPLC measurement conditions C)]

Property values of {(4-dipropylaminobutyl)-[4-(1H-imidazol-2-ylmethyl)-(1-methylimidazol-2-ylmethyl)aminomethylbenzyl]methyl}amine (46)

$^1$H-NMR (400 MHz, CDCl$_3$, ppm) δ: 7.34(d, 2H, J=8.06 Hz, Ph), 7.27(d, 2H, J=8.06 Hz, Ph), 7.09(bs, 2H, imidazole-), 6.99(d, 1H, J=1.27 Hz, Me-imidazole-), 6.86(d, 1H, J=1.24 Hz, Me-imidazole-), 3.67(s, 2H, ArCH$_2$N), 3.63(s, 2H, ArCH$_2$N), 3.53(s, 3H, Me-imidazole-), 3.47(s, 2H, ArCH$_2$N), 3.46(s, 2H, ArCH$_2$N), 2.43~2.30(m, 8H, NCH$_2$CH$_2$×4), 2.16(s, 3H, Me-N—), 1.55~1.38(m, 8H, NCH$_2$CH$_2$×4), 0.86(dd, 6H, J=7.34, 7.38 Hz, NCH$_2$CH$_2$CH$_3$×2)

$^{13}$C-NMR (100 MHz, CDCl$_3$, ppm) δ: 145.99, 143.55, 138.76, 137.76, 129.44, 129.41, 128.20, 127.19, 121.98, 62.39, 59.25, 57.92, 56.63, 54.51, 49.37, 47.35, 42.57, 33.08, 25.79, 25.33, 20.59, 12.38

The compound numbers used in the above examples are given in the following table for reference.

TABLE 1

(1)

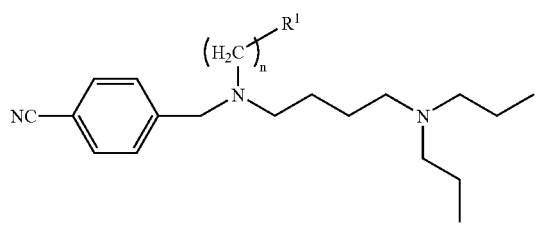

TABLE 1-continued
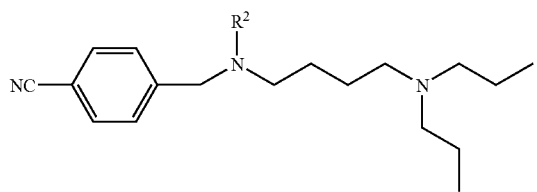
(2)
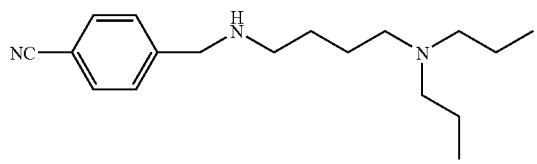
(2a)
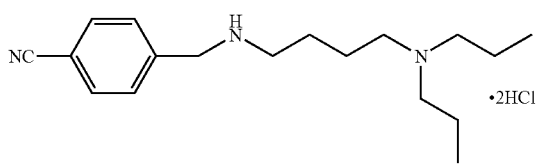
(2aa)
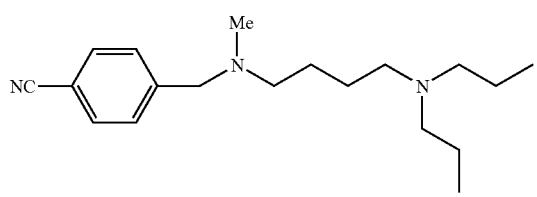
(2b)
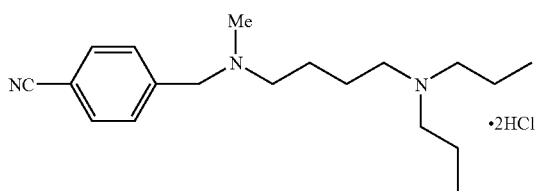
(2ba)
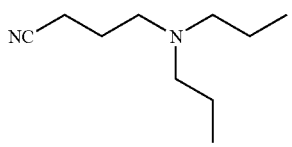
(3)
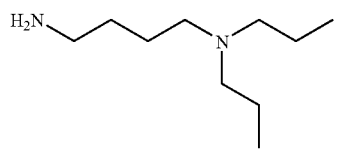
(4)
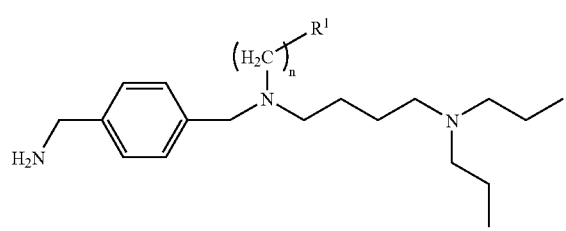
(5)

TABLE 1-continued
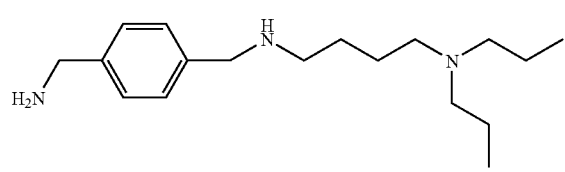
(5a)
R³—CHO (6)
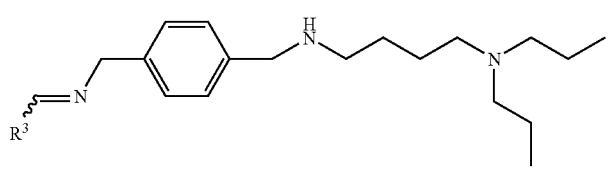
(7)
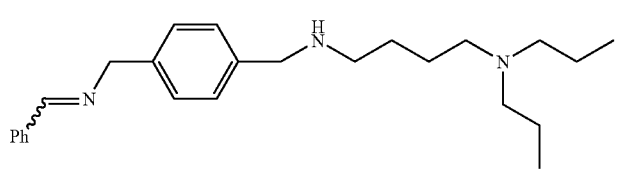
(7a)
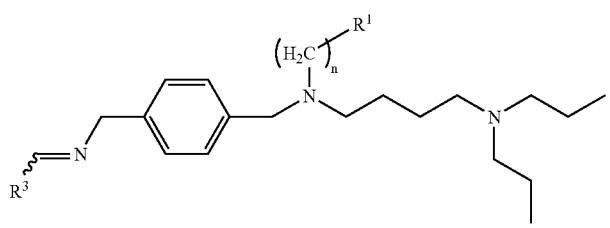
(8)
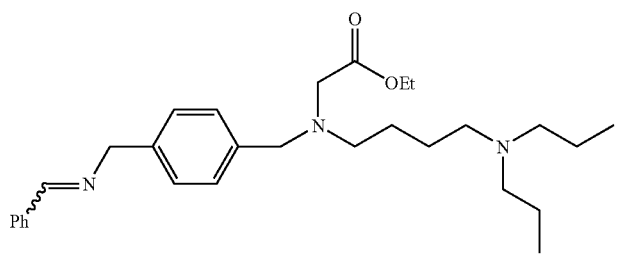
(8a)
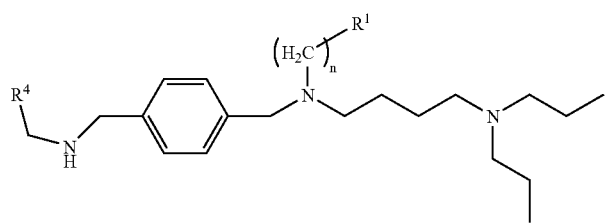
(9)

TABLE 1-continued
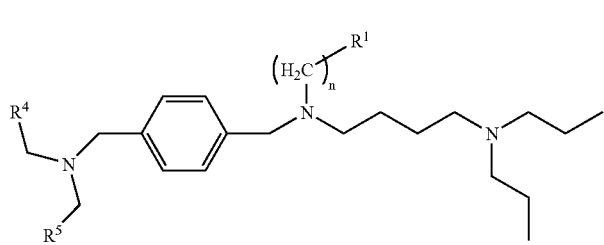
(10)
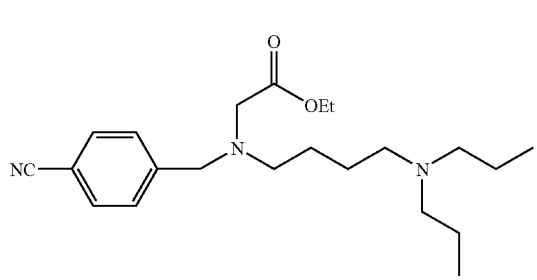
(11)
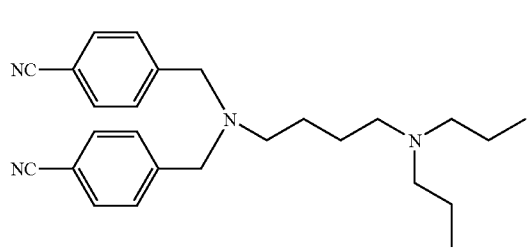
(12)
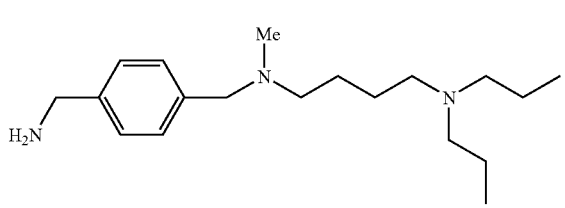
(13)
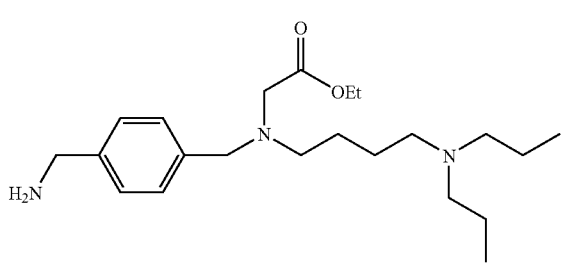
(14)
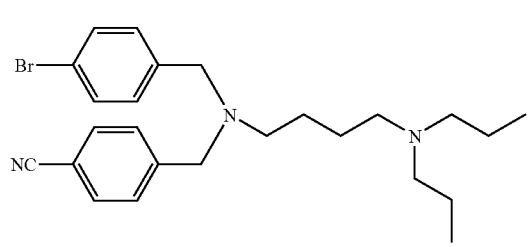
(15)

TABLE 1-continued
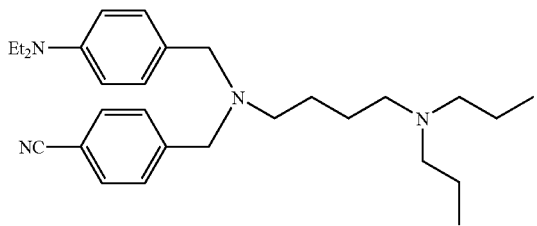
(16)
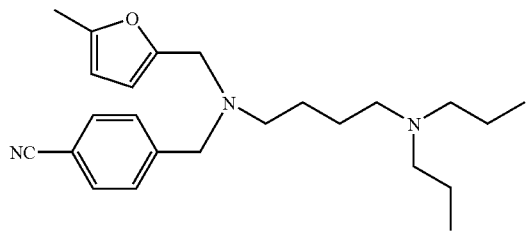
(17)
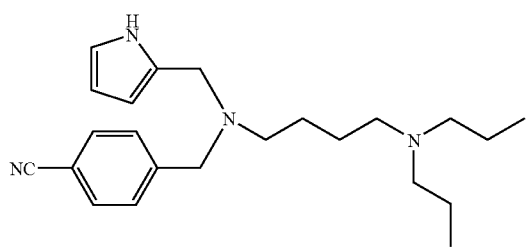
(18)
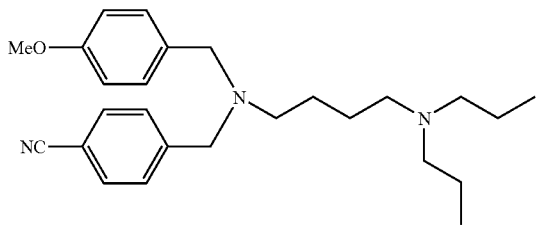
(19)
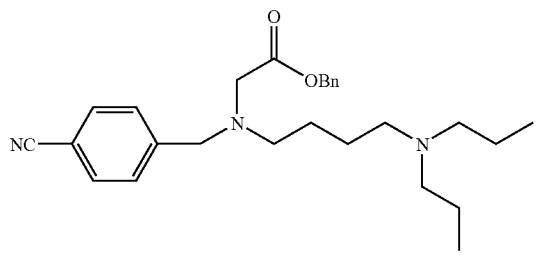
(20)
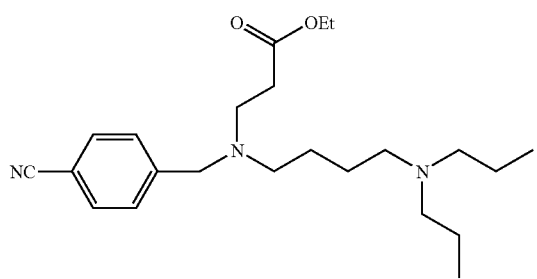
(21)

TABLE 1-continued
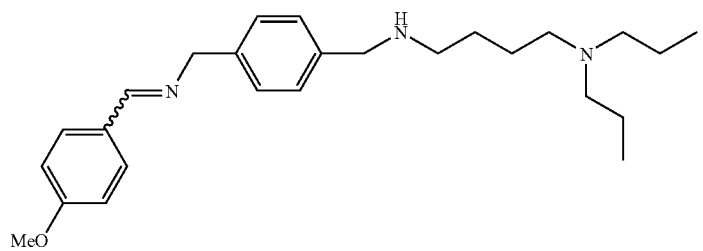
(22)
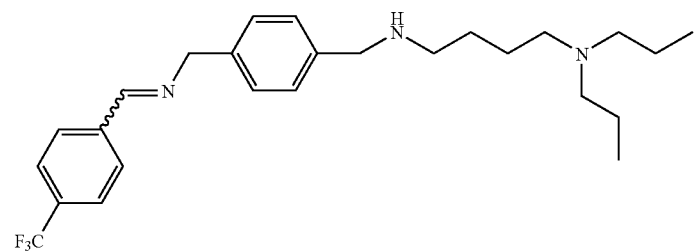
(23)
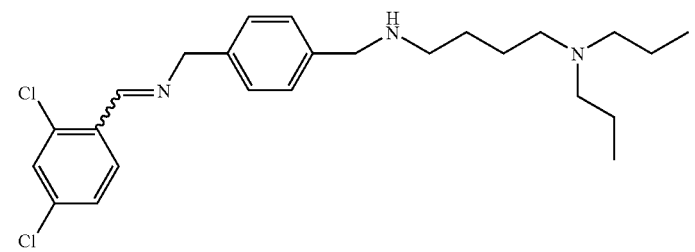
(24)
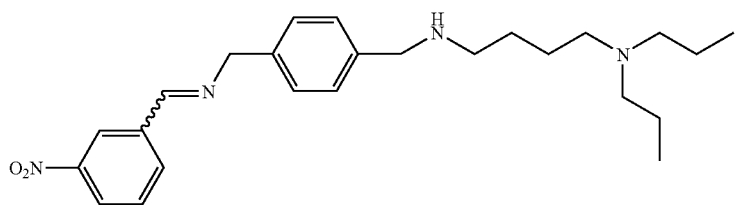
(25)
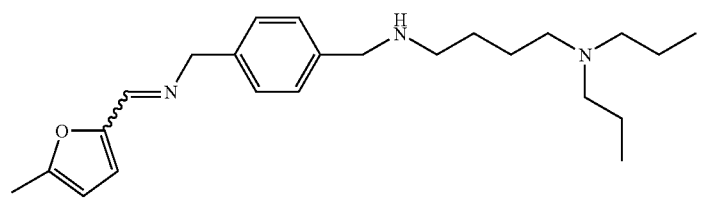
(26)
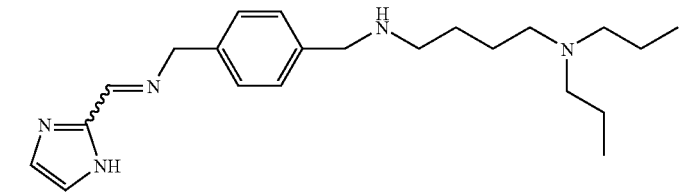
(27)

| | |
|---|---|
| 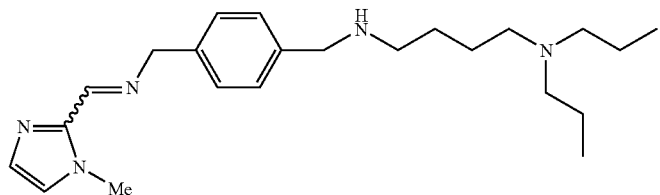 | (28) |
| 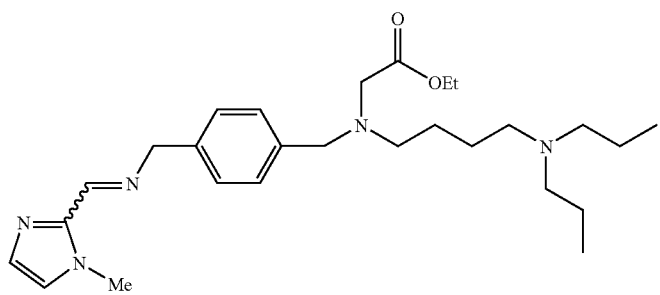 | (29) |
| 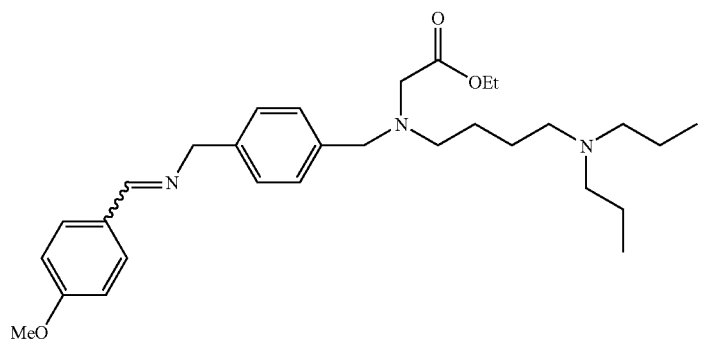 | (30) |
| 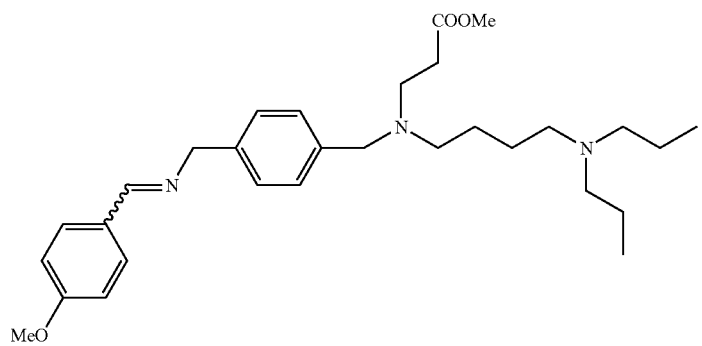 | (31) |

TABLE 1-continued (32), (33), (34), (35)

TABLE 1-continued
(36)
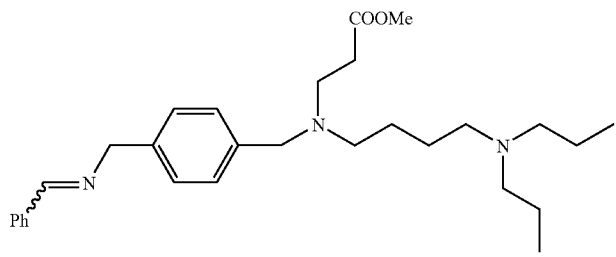
(37)
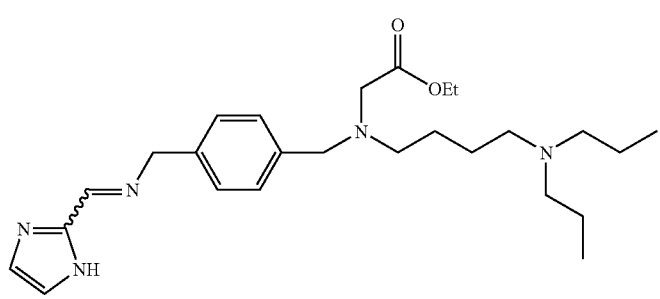
(38)
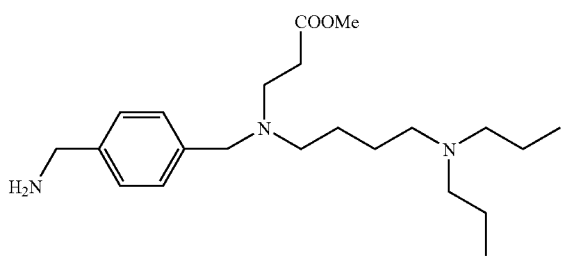
(39)
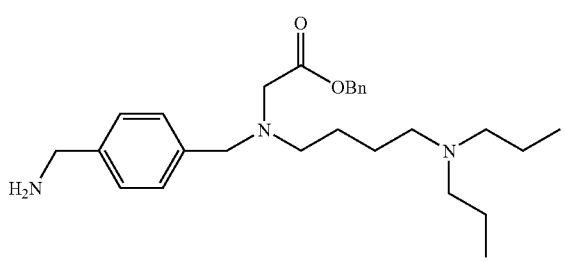
(40)
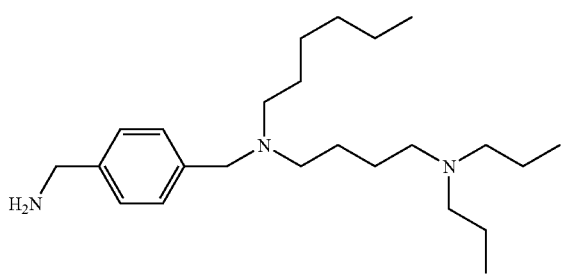

TABLE 1-continued
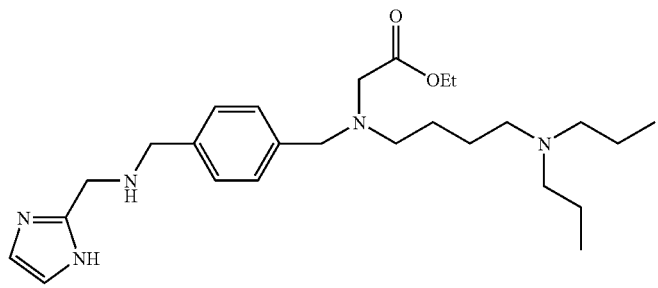
(41)
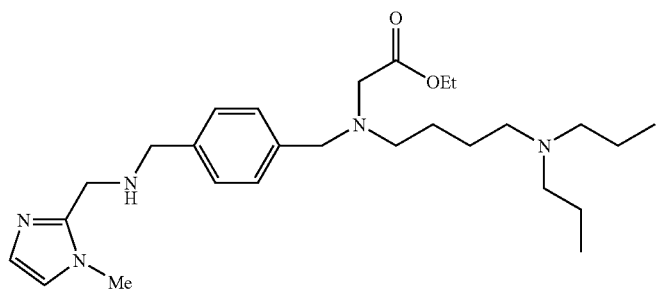
(42)
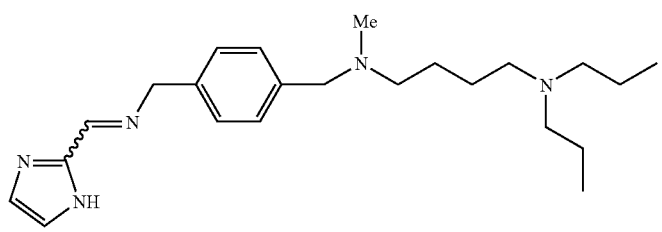
(43)
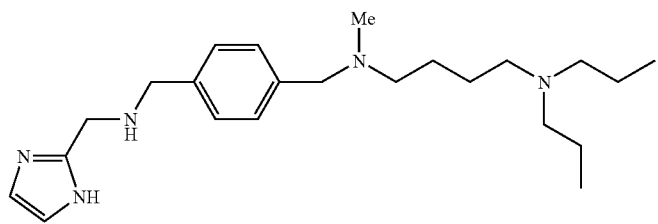
(44)
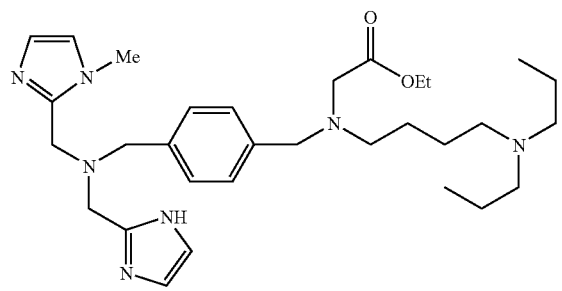
(45)

TABLE 1-continued
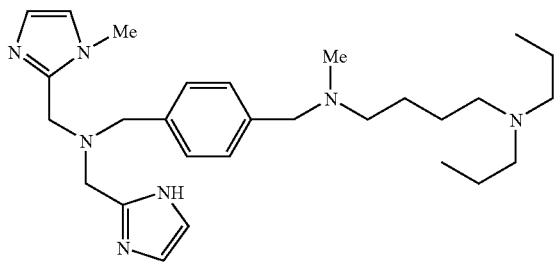
(46)
Formulation examples and test examples are given below. Note that the carrier (diluent) and the auxiliary agent, the mixing ratio, and the active component may be changed in a wide range. Examples using the compounds (2a), (2b), (15), (16), (17), (18), (19) and (20), and the hydrochlorides (2aa) and (2ba) are given below.
[Formula 130]
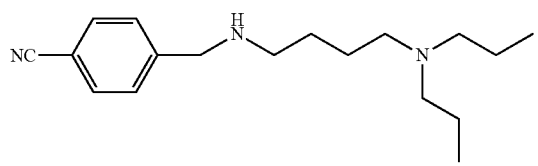
(2a)
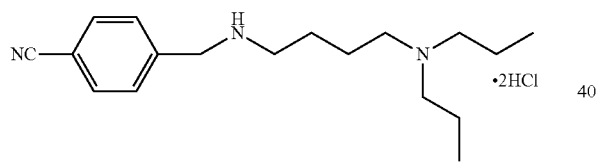
(2aa)
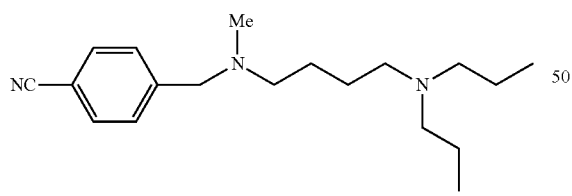
(2b)
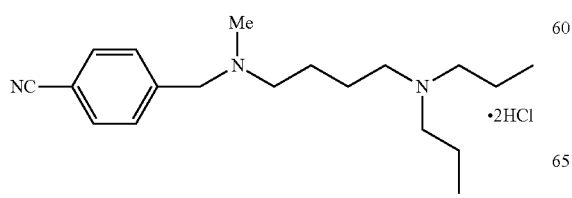
(2ba)
-continued
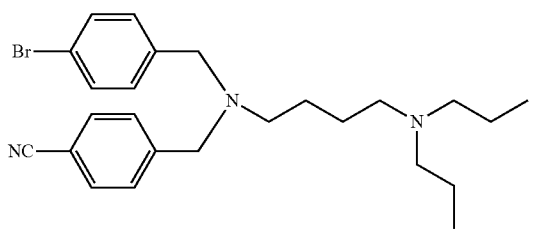
(15)
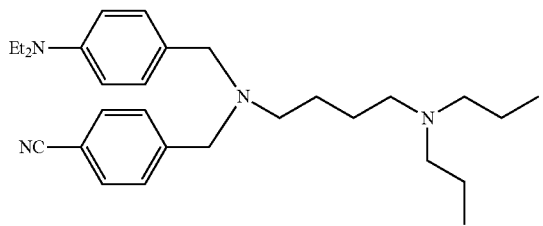
(16)
(16)
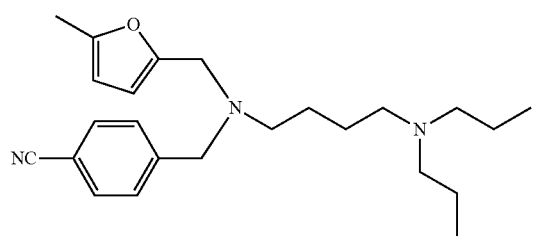
(17)
(17)
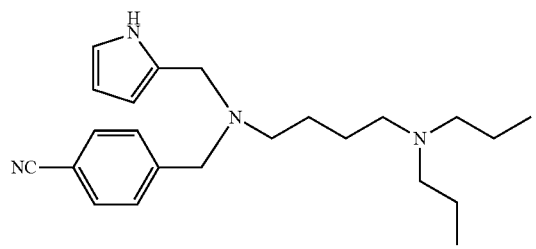
(18)

-continued

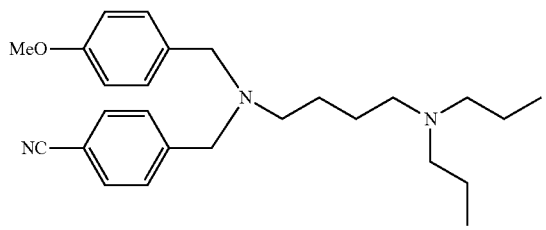

(19)

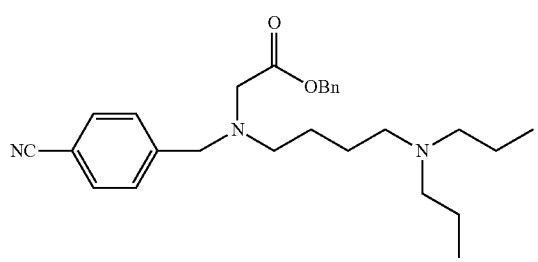

(20)

FORMULATION EXAMPLE 1

Powder 3 parts by weight of the compound (2a), 40 parts by weight of clay, and 57 parts by weight of talc were ground, mixed, and used as a dusting powder.

FORMULATION EXAMPLE 2

Water Dispersible Powder 50 parts by weight of the compound (2b), 5 parts by weight of lignin sulfonate, 3 parts by weight of an alkylsulfonate, and 42 parts by weight of diatomaceous earth were ground, mixed, diluted with water and used as a water dispersible powder.

FORMULATION EXAMPLE 3

Granules 5 parts by weight of the compound (2aa); 43 parts by weight of bentonite, 45 parts by weight of clay, and 7 parts by weight of lignin sulfonate were uniformly mixed. After the addition of water, the mixture was kneaded, granulated using an extruder, and dried to prepare granules.

FORMULATION EXAMPLE 4

Emulsion 20 parts by weight of the compound (2ba), 10 parts by weight of a polyoxyethylene alkyl aryl ether, 3 parts by weight of polyoxyethylene sorbitan monolaurate, and 67 parts by weight of xylene were uniformly mixed and dissolved each other to prepare an emulsion.

TEST EXAMPLE 1

Protection Test of *Pseudoperonospora cubensis*

Water dispersible powders were prepared in the same manner as in Formulation Example 2 using the compound (2a), (2aa), (2b), (2ba), (15), (16), (17), (18), (19), or (20). The each water dispersible powder was diluted with water to a predetermined concentration (1000 mg/l) and suspended. The diluted suspension was sprayed onto cucumber cotyledons (var. Sagami-Hanjiro) grown in a rectangular plastic pot (6.4 cm×6.4 cm) at 100 1/10 a. After air-drying the sprayed leaves one day, a *Pseudoperonospora cubensis* spore suspension was sprayed onto the leaves to inoculate, and the leaves were maintained at 25° C. under high humidity conditions. After six days from the inoculation, the incidence of *Pseudoperonospora cubensis* was investigated according to the following criteria. The protective value is calculated according to the following equation 1. The results are shown in Table 1.

(Criteria)

| Incidence | Symptom area ratio |
|---|---|
| 0 | Not infected |
| 0.5 | Symptom area ratio: less than 10% |
| 1 | Symptom area ratio: 10% or more and less than 20% |
| 2 | Symptom area ratio: 20% or more and less than 40% |
| 3 | Symptom area ratio: 40% or more and less than 60% |
| 4 | Symptom area ratio: 60% or more and less than 80% |
| 5 | Symptom area ratio: 80% or more |

Protective value(%)=(1−average incidence in sprayed area/average incidence in non-sprayed area)×100  [Equation 1]

TABLE 2

| Test compounds (Compounds in table 2) | Spraying concentration (ppm) | Protective value (%) |
|---|---|---|
| (2a) | 1000 | 100 |
| (2aa) | 1000 | 100 |
| (2b) | 1000 | 100 |
| (2ba) | 1000 | 100 |
| (15) | 1000 | 100 |
| (16) | 1000 | 100 |
| (17) | 1000 | 100 |
| (18) | 1000 | 100 |
| (19) | 1000 | 90 |
| (20) | 1000 | 100 |
| No treatment | — | 0 |

INDUSTRIAL APPLICABILITY

According to the present invention, the benzylamine derivative represented by the general formula (5) and the secondary amine derivative represented by the general formula (9) can be efficiently and advantageously produced using the benzonitrile derivative represented by the general formula (1) as an intermediate. Furthermore, according to the present invention, the benzonitrile derivative represented by the above general formulas (1) and (2) and salts thereof can be utilized as active components of bactericides.

What is claimed is:

1. A method of producing a benzonitrile derivative represented by the following general formula (1),

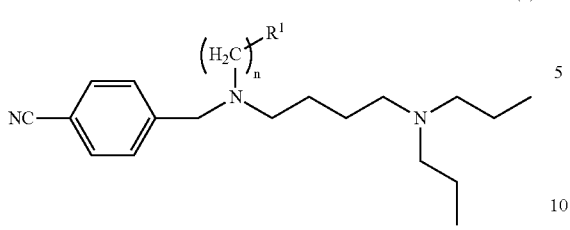

(1)

using 4-dipropylaminobutyronitrile (3) as a raw material, the method comprising;

subjecting the 4-dipropylaminobutyronitrile (3) to a reduction reaction to produce 4-dipropylaminobutylamine (4), and

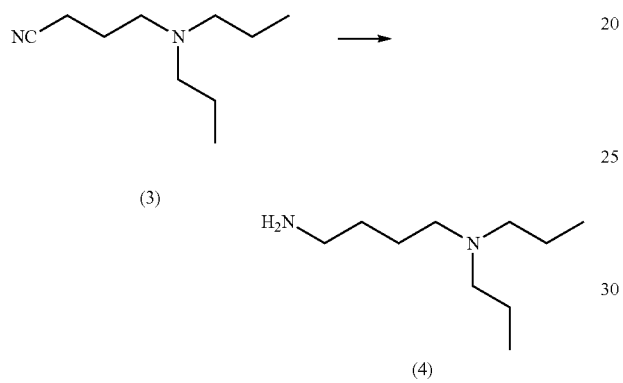

subjecting the primary amino group of the 4-dipropylaminobutylamine (4) to an alkylation reaction and a reductive alkylation reaction to produce the benzonitrile derivative represented by the general formula (1),

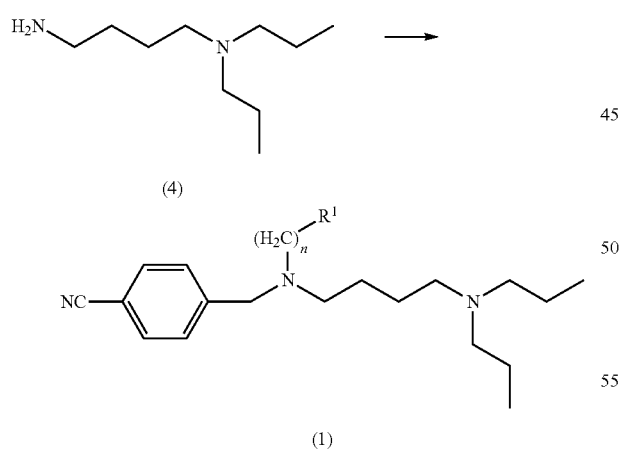

wherein n represents an integer from 0 to 3; and $R^1$ represents hydrogen; a linear or branched alkyl group having 1 to 6 carbon atoms; a halogen atom; a nitro group; a cyano group; a carboxyl group; an amide group; a sulfonyl group; a hydroxyl group; a linear or branched alkoxy group having 1 to 6 carbon atoms; a linear or branched alkylcarbonyl group having 1 to 6 carbon atoms; a linear or branched alkoxycarbonyl group having 1 to 6 carbon atoms; a phenyl group; a phenyl group of which the aromatic ring is substituted by one or more of a halogen atom, a nitro group, a cyano group, a carboxyl group, an amide group, a sulfonyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a benzoyl group; a benzoyl group of which the aromatic ring is substituted by one or more of a halogen atom, a nitro group, a cyano group, a carboxyl group, an amide group, a sulfonyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a benzyloxycarbonyl group, a pyridyl group, a furyl group, an imidazolyl group, a triazolyl group, a tetrazolyl group, a naphthyl group, or a tetrahydrofuryl group, provided that, when n=0, $R^1$ represents hydrogen or a linear or branched alkyl group having 1 to 6 carbon atoms.

2. A method of producing a benzonitrile derivative represented by the following general formula (1),

[Formula 22]

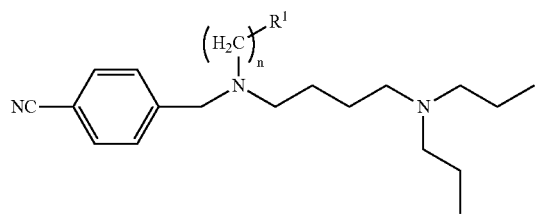

(1)

the method comprising:
(1) subjecting 4-dipropylaminobutyronitrile (3) to a reduction reaction to produce 4-dipropylaminobutylamine (4),

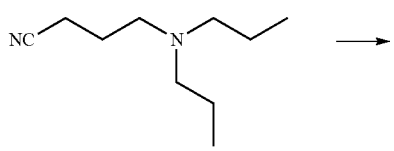

(3)

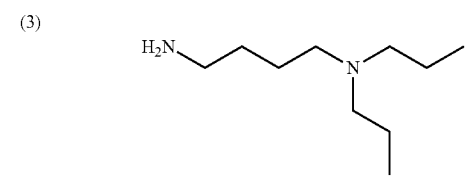

(4)

(2) subjecting the 4-dipropylaminobutylamine (4) to a reductive alkylation reaction using 4-cyanobenzaldehyde to produce 4-[(4-dipropylaminobutyl)amino]methylbenzonitrile (2a), and

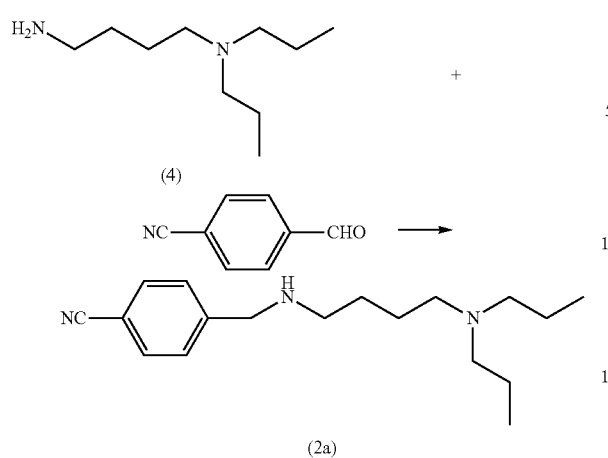

(3) subjecting the 4-[(4-dipropylaminobutyl)amino]methylbenzonitrile (2a) to an alkylation reaction,

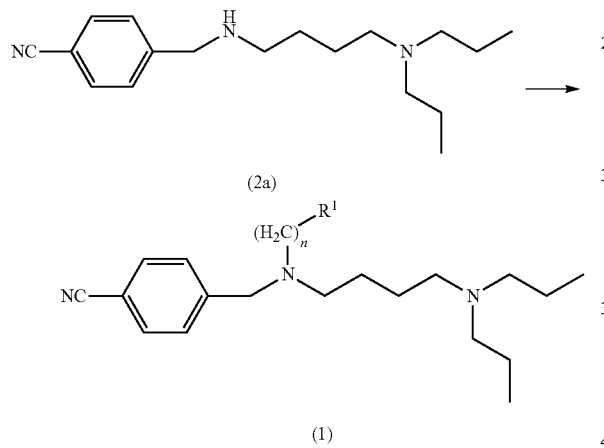

wherein n represents an integer from 0 to 3; and $R^1$ represents hydrogen; a linear or branched alkyl group having 1 to 6 carbon atoms; a halogen atom; a nitro group; a cyano group; a carboxyl group; an amide group; a sulfonyl group; a hydroxyl group; a linear or branched alkoxy group having 1 to 6 carbon atoms; a linear or branched alkylcarbonyl group having 1 to 6 carbon atoms; a linear or branched alkoxycarbonyl group having 1 to 6 carbon atoms; a phenyl group; a phenyl group of which the aromatic ring is substituted by one or more of a halogen atom, a nitro group, a cyano group, a carboxyl group, an amide group, a sulfonyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a benzoyl group; a benzoyl group of which the aromatic ring is substituted by one or more of a halogen atom, a nitro group, a cyano group, a carboxyl group, an amide group, a sulfonyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a benzyloxycarbonyl group, a pyridyl group, a furyl group, an imidazolyl group, a triazolyl group, a tetrazolyl group, a naphthyl group, or a tetrahydrofuryl group, provided that, when n=0, $R^1$ represents hydrogen or a linear or branched alkyl group having 1 to 6 carbon atoms.

3. A method of producing 4-[(4-dipropylaminobutyl)amino]imethylbenzonitrile (2a), the method comprising;
subjecting 4-dipropylaminobutyronitrile (3) to a reduction reaction to produce 4-dipropylaminobutylamine (4), and
subjecting the obtained 4-dipropylaminobutylamine (4) to a reductive alkylation reaction using 4-cyanobenzaldehyde

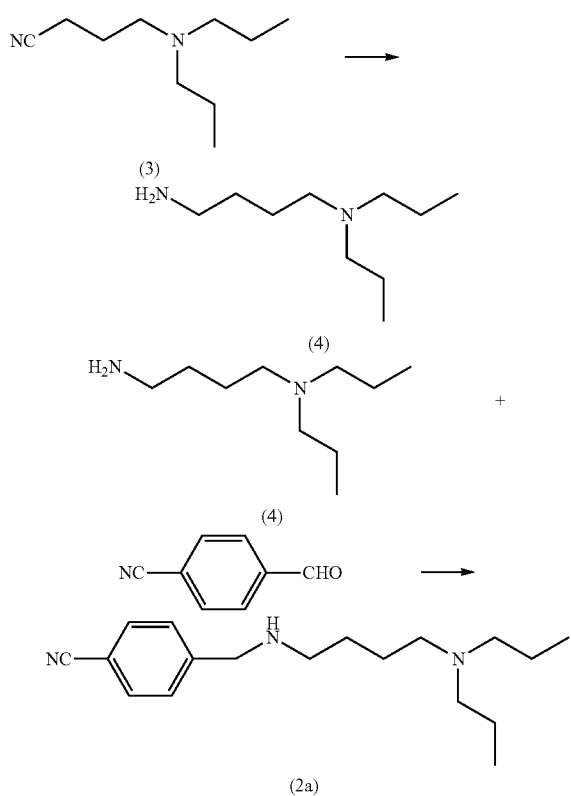

4. A method of producing 4-[(4-dipropylaminobutyl)methylamino]methylbenzonitrile (2b), the method comprising:
subjecting 4-[(4-dipropylaminobutyl)amino]methylbenzonitrile (2a) to methylation,

[Formula 11]

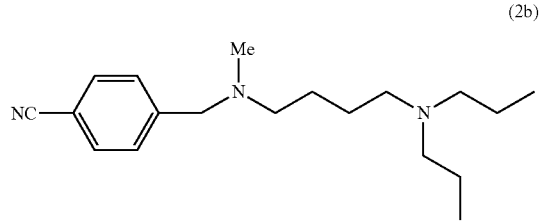

wherein the methylation is carried out using a formaldehyde aqueous solution and formic acid.

5. A method of purifying a benzonitrile derivative represented by the following general formula (1), the method comprising forming a salt by causing a crude compound of the benzonitrile derivative represented by the general formula (1) to react with one or more inorganic and organic acids, and recrystallizing the salt,

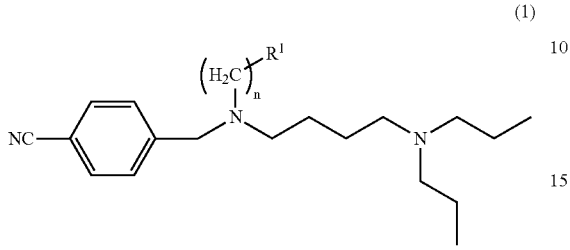

wherein n represents an integer from 0 to 3; and $R^1$ represents hydrogen; a linear or branched alkyl group having 1 to 6 carbon atoms; a halogen atom; a nitro group; a cyano group; a carboxyl group; an amide group; a sulfonyl group; a hydroxyl group; a linear or branched alkoxy group having 1 to 6 carbon atoms; a linear or branched alkylcarbonyl group having 1 to 6 carbon atoms; a linear or branched alkoxycarbonyl group having 1 to 6 carbon atoms; a phenyl group; a phenyl group of which the aromatic ring is substituted by one or more of a halogen atom, a nitro group, a cyano group, a carboxyl group, an amide group, a sulfonyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a benzoyl group; a benzoyl group of which the aromatic ring is substituted by one or more of a halogen atom, a nitro group, a cyano group, a carboxyl group, an amide group, a sulfonyl group, a phenyl group, a linear or branched alkyl group having 1 to 6 carbon atoms, a linear or branched alkoxy group having 1 to 6 carbon atoms, a linear or branched alkylcarbonyl group having 1 to 6 carbon atoms, a linear or branched alkoxycarbonyl group having 1 to 6 carbon atoms, and a hydroxyl group; a benzyloxycarbonyl group, a pyridyl group, a furyl group, an imidazolyl group, a triazolyl group, a tetrazolyl group, a naphthyl group, or a tetrahydrofuryl group, provided that, when n=0, $R^1$ represents hydrogen or a linear or branched alkyl group having 1 to 6 carbon atoms.

6. The method according to claim 4, wherein the methylation reaction is carried out using an alkylating agent such as an alkyl halide.

7. The method according to claim 4, wherein the methylation reaction is a reductive alkylation reaction using an aldehyde derivative.

* * * * *